(12) United States Patent
Slassi et al.

(10) Patent No.: US 7,935,703 B2
(45) Date of Patent: May 3, 2011

(54) PIPERAZINES AND PIPERIDINES AS MGLUR5 POTENTIATORS

(75) Inventors: Abdelmalik Slassi, Mississauga (CA); Methvin Isaac, Brampton (CA); Jalaj Arora, Milton (CA); Dean Brown, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 172 days.

(21) Appl. No.: 12/160,959

(22) PCT Filed: Jan. 5, 2007

(86) PCT No.: PCT/US2007/000231
§ 371 (c)(1),
(2), (4) Date: Sep. 16, 2008

(87) PCT Pub. No.: WO2007/087135
PCT Pub. Date: Aug. 2, 2007

(65) Prior Publication Data
US 2009/0023711 A1    Jan. 22, 2009

Related U.S. Application Data

(60) Provisional application No. 60/758,992, filed on Jan. 17, 2006.

(51) Int. Cl.
| | |
|---|---|
| *A61K 31/497* | (2006.01) |
| *A61K 31/4965* | (2006.01) |
| *A61K 31/445* | (2006.01) |
| *A01N 43/40* | (2006.01) |
| *C07D 211/60* | (2006.01) |
| *C07D 403/00* | (2006.01) |
| *C07D 241/04* | (2006.01) |
| *C07D 295/00* | (2006.01) |
| *C07D 401/00* | (2006.01) |

(52) U.S. Cl. ......... 514/252.13; 514/252.14; 514/254.02; 514/253.01; 514/254.05; 514/315; 514/255.01; 544/366; 544/391; 544/359; 544/360; 544/369; 544/379; 546/228

(58) Field of Classification Search .......... 514/252.14, 514/252.13, 254.02, 253.01, 315, 254.05, 514/255.01; 544/36, 391, 359, 360, 369, 379; 546/228; 540/575
See application file for complete search history.

(56) References Cited

U.S. PATENT DOCUMENTS
4,617,309 A    10/1986   Böttcher et al.

FOREIGN PATENT DOCUMENTS

| EP | 0105397 A1 | | 4/1984 |
|---|---|---|---|
| JP | 2001261657 | * | 3/2000 |
| WO | WO-03/093236 A1 | | 11/2003 |
| WO | WO-2004/089470 A2 | | 10/2004 |
| WO | WO 2004089415 | * | 10/2004 |
| WO | WO 2004089470 | * | 10/2004 |
| WO | WO-2005/030128 A2 | | 4/2005 |
| WO | WO-2006/002349 A1 | | 1/2006 |
| WO | WO 2006002349 | * | 1/2006 |

OTHER PUBLICATIONS

Pietraszek, et al., mGLuR5, but not mGluR1, Antagonistic Modifies MK-801-induced Locomotor Activity and Deficit of Prepulse Inhibition, Neuropharmacology, 49, 73-85 (2005).*

* cited by examiner

*Primary Examiner* — James O Wilson
*Assistant Examiner* — Erich A Leeser
(74) *Attorney, Agent, or Firm* — Connolly Bove Lodge & Hutz, LLP

(57) ABSTRACT

Compounds of Formula I or pharmaceutically acceptable salts or solvates thereof:

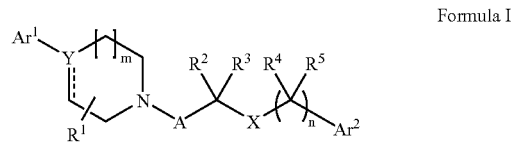

Formula I wherein $Ar^1$, $Ar^2$, A, X, Y, m, n and $R^1$, $R^2$, $R^3$, $R^4$ and $R^5$ are as described in the specification, processes for their preparation, pharmaceutical formulations comprising them and their use in therapy, particularly in the therapy of neurological and psychiatric disorders associated with glutamate dysfunction.

2 Claims, No Drawings

PIPERAZINES AND PIPERIDINES AS MGLUR5 POTENTIATORS

This application is a national stage application (under 35 U.S.C. §371) of PCT/US2007/000231, filed Jan. 5, 2007, which claims benefit of U.S. Provisional Application 60/758,992, filed Jan. 17, 2006.

FIELD OF THE INVENTION

The present invention relates to a new class of compounds, to pharmaceutical formulations containing said compounds and to the use of said compounds in therapy. The invention further relates to the process for the preparation of said compounds and to new intermediates prepared therein.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage-and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Molecular cloning has identified eight distinct mGluR subtypes, termed mGluR1 through mGluR8. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

Neurological, Psychiatric and Pain Disorders.

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1 (1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated, Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13: 1031 (1994), Pin et al., *Neuropharmacology* 34: 1, Knopfel et al., *J. Med. Chem.* 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Further, it has also been shown that mGluR5 antagonists are useful for the treatment of addictions or cravings (for drugs, tobacco, alcohol, any appetizing macronutrients or non-essential food items).

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Medical Use

The group I receptor, mGluR5, has been implicated in a number of central nervous system disease states, including pain (Salt and Binns, 2000; Bhave, et al., 2001), anxiety (Spooren, et al., 2000; Tatarczynska, et al., 2001), addiction to cocaine (Chiamulera, et al., 2001) and schizophrenia (Chavez-Noriega, et al., 2002). The N-methyl-D-aspartate (NMDA) receptor, an ionotropic glutamate receptor, has also been implicated in physiological and pathological processes. Of specific interest, blockade of NMDA receptors produces a transient state of psychosis and schizophrenia-like cognitive deficits (Krystal, et al., Arch Gen Psychiatry, 51: 199-214, 1994; Lahti, et al., Neuropsychopharmacol., 13: 9-19, 1995; Newcomer, et al., Neuropsychopharmacol., 20:106-118, 1999). Pharmacological manipulation of NMDA receptor function may be critical for the treatment of many neurological and psychiatric disorders such as epilepsy, Alzheimer's disease, drug dependence and schizophrenia (Kemp and McKernan, 2002). A functional interaction between NMDA receptors and mGluR5 has been demonstrated at a cellular level and at a behavioral level. Thus, activation of Group I mGluRs by DHPG enhanced NMDA-receptor mediated responses in mouse CA1 pyramidal neurones (Mannaioni, et al., J. Neurosci., 21:5925-5934, 2001). This effect was inhibited by MPEP, demonstrating that NMDA receptor function was enhanced through activation of mGluR5 (Mannaioni, et al., J. Neurosci., 21:5925-5934, 2001). Modulation of mGluR5 also altered the cognitive and behavioral abnormalities associated with NMDA receptor deficiency (Homayoun, et al., Neuropsychopharmacol., 29: 1259-1269, 2004). Together these data suggest that potentiation of mGluR5 could be beneficial in the treatment of disorders such as schizophrenia.

Non-Medical Use

In addition to their use in therapeutic medicine, the compounds of Formula I, as well as salts and hydrates of such compounds, are useful as pharmacological tools in the development and standardization of in vitro and in vivo test systems for the evaluation of the effects of potentiators of mGluR related activity in laboratory animals such as cats, dogs, rabbits, monkeys, rats and mice, as part of the search for new therapeutic agents.

SUMMARY OF THE INVENTION

It has been discovered that the compounds of the present invention are potentiators of mGluR5 receptor function and are, therefore, useful in the treatment of neurological and psychiatric disorders associated with glutamate dysfunction.

One embodiment of the invention relates to compounds of Formula I or a pharmaceutically acceptable salt or solvate thereof:

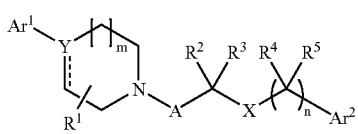

Formula I wherein:
$Ar^1$ is selected from the group consisting of phenyl and pyridyl, which may be substituted with up to 4 substituents independently selected from the group consisting of alkyl, halo, haloalkyl and CN;
$Ar^2$ is selected from the group consisting of phenyl and heteroaryl, which may be substituted with up to 4 substituents independently selected from the group consisting of alkyl, halo and haloalkyl;

A is selected from the group consisting of C(O), C(S) and $S(O)_2$;
X is selected from the group consisting of O and S;
Y is selected from the group consisting of C and N;
m is selected from the group consisting of 1 and 2;
n is selected from the group consisting of 1 and 2;
$R^1$ is selected from the group consisting of H and alkyl,
$R^2$, $R^3$, $R^4$ and $R^5$ are independently selected from the group consisting of H and alkyl; with the proviso that the compound is not 1-[(benzyloxy)acetyl]-4-(4-chlorophenyl)piperazine, 1-[(benzyloxy)acetyl]-4-(2-methoxyphenyl)piperazine, 1-[(benzyloxy)acetyl]-4-(4-methoxyphenyl)piperazine, 1-[(benzyloxy)acetyl]-4-(3-chlorophenyl)piperazine, or 2-Benzyloxy-1-[4-(3-methyl-pyridin-2-yl)-piperazin-1-yl]-ethanone.

Another embodiment of the invention is a pharmaceutical composition comprising as active ingredient a therapeutically effective amount of the compound according to Formula I and one or more pharmaceutically acceptable diluents, excipients and/or inert carriers.

Other embodiments of the invention, as described in more detail below, relate to a compound according to Formula I for use in therapy, in the treatment of mGluR 5 mediated disorders, and in the manufacture of a medicament for the treatment of mGluR5 mediated disorders.

Still other embodiments relate to a method of treatment of mGluR5-mediated disorders, comprising administering to a mammal a therapeutically effective amount of the compound according to Formula I.

DETAILED DESCRIPTION OF THE PREFERRED EMBODIMENTS

The present invention is based upon the discovery of compounds which are potentiators of metabotropic glutamate receptor function. More particularly, the compounds of the present invention exhibit activity as potentiators of mGluR5 receptor function and, therefore, are useful in therapy, in particular for the treatment of neurological and psychiatric disorders,

DEFINITIONS

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "alkyl" as used herein means a straight-or branched-chain hydrocarbon radical having from one to six carbon atoms, and includes methyl, ethyl, propyl, isopropyl, t-butyl and the like.

The term "alkoxy" as used herein means a straight-or branched-chain alkoxy radical having from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "haloalkyl" as used herein means an alkyl group in which at least one H atom has been replaced by a halo atom, and includes groups such as $CF_3$, $CH_2Br$ and the like.

The term "alkylene" as used herein means a difunctional branched or unbranched saturated hydrocarbon radical having one to six carbon atoms, and includes methylene, ethylene, n-propylene, n-butylene and the like.

The term "aryl" as used herein means an aromatic group having five to twelve atoms, and includes phenyl, naphthyl and the like.

The term "heteroaryl" means an aromatic group having from 5 to 8 atoms which includes at least one heteroatom selected from the group consisting of N, S and O, and includes pyridyl, furyl, thienyl, thiazolyl, pyrazinyl, pyrimidinyl, oxazolyl and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di-and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono-or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound of Formula I which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds

Compounds of the invention conform generally to Formula I:

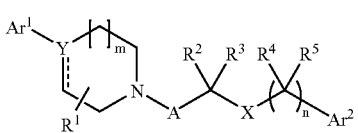

Formula I wherein:

$Ar^1$ is selected from the group consisting of phenyl and pyridyl, which may be substituted with up to 4 substituents independently selected from the group consisting of alkyl, halo, haloalkyl and CN;

$Ar^2$ is selected from the group consisting of phenyl and heteroaryl, which may be substituted with up to 4 substituents independently selected from the group consisting of alkyl, halo and haloalkyl;

A is selected from the group consisting of C(O), C(S) and $S(O)_2$;

X is selected from the group consisting of O and S;

Y is selected from the group consisting of C and N;

m is selected from the group consisting of 1 and 2;

n is selected from the group consisting of 1 and 2;

$R^1$ is selected from the group consisting of H and alkyl, $R^2$, $R^3$, $R^4$ and $R^5$ are independently selected from the group consisting of H and alkyl; with the proviso that the compound is not 1-[(benzyloxy)acetyl]-4-(4-chlorophenyl)piperazine, 1-[(benzyloxy)acetyl]-4-(2-methoxyphenyl)piperazine, 1-[(benzyloxy)acetyl]-4-(4-methoxyphenyl)piperazine, 1-[(benzyloxy)acetyl]-4-(3-chlorophenyl)piperazine, or 2-Benzyloxy-1-[4-(3-methyl-pyridin-2-yl)-piperazin-1-yl]-ethanone.

In particular embodiments of the invention $Ar^1$ is a phenyl group. In other embodiments $Ar^2$ is selected from the group consisting of phenyl, thienyl, thiazolyl and pyridyl. In still others $Ar^2$ is selected from the group consisting of thienyl and pyridyl.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate or chemical or enzymatic resolution methodology, by synthesis from optically active starting materials or by asymmetric synthesis based on the procedures described thereafter.

It will also be understood by those of skill in the art that certain compounds of the present invention may exist in solvated, for example hydrated, as well as unsolvated forms. It will further be understood that the present invention encompasses all such solvated forms of the compounds of Formula I.

Within the scope of the invention are also salts of the compounds of Formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of Formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the compounds 1 to 89 as illustrated in the following table, their pharmaceutically acceptable salts, hydrates, solvates, optical isomers, and combinations thereof:

| No. | Structure | Name |
|---|---|---|
| 1 | 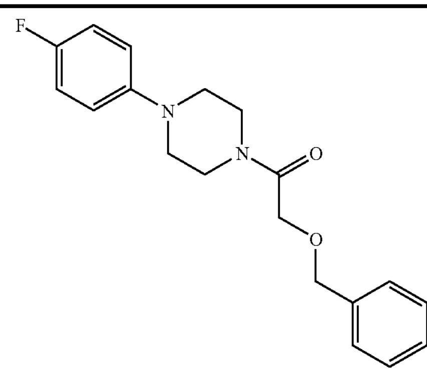 | 2-Benzyloxy-1-[4-(4-fluorophenyl)-piperazin-1-yl]-ethanone |
| 2 | 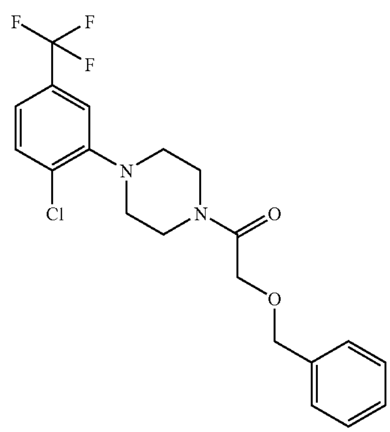 | 2-Benzyloxy-1-[4-(2-chloro-5-trifluoro methyl-phenyl)-piperazin-1-yl]-ethanone |
| 3 | 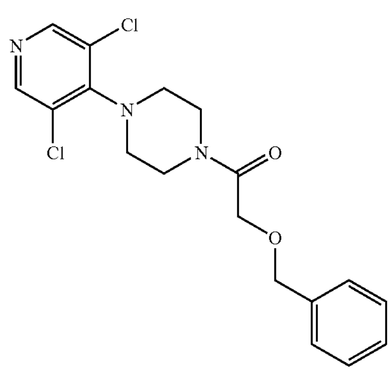 | 2-Benzyloxy-1-[4-(3,5-dichloro-pyridin-4-yl)-piperazin-1-yl]-ethanone |

-continued

| No. | Structure | Name |
|-----|-----------|------|
| 4 | 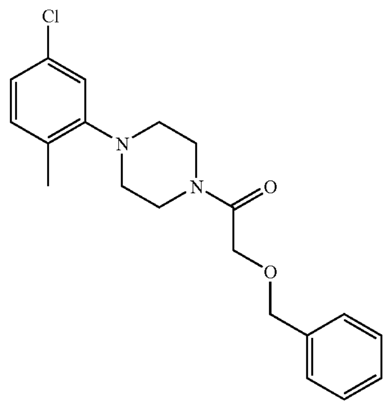 | 2-Benzyloxy-1-(4-(5-chloro-2-methyl-phenyl)-piperazin-1-yl]-ethanone |
| 5 | 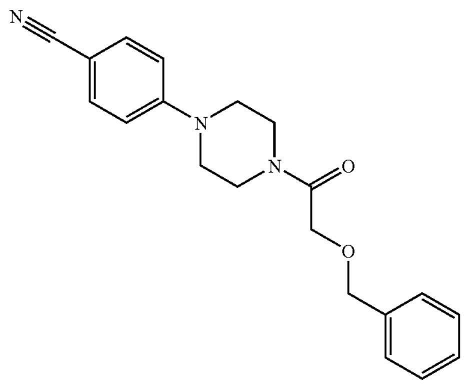 | 4-[4-(2-Benzyloxyacetyl)-piperazin-1-yl]-benzonitrile |
| 6 | 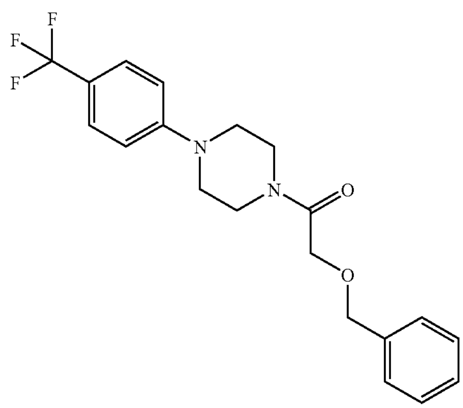 | 2-Benzyloxy-1-[4-(4-trifluoromethyl-phenyl)-piperazin-1-yl]-ethanone |
| 7 | 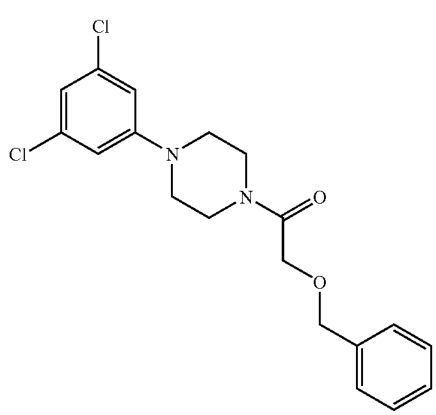 | 2-Benzyloxy-1-[4-(3,5-dichloromethyl phenyl)-piperazin-1-yl]-ethanone |

-continued
| No. | Structure | Name |
|---|---|---|
| 8 | 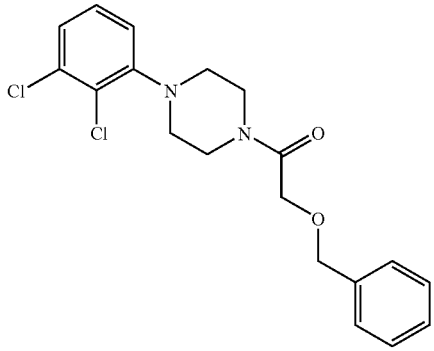 | 2-Benzyloxy-1-[4-(2,3-dichlorophenyl)-piperazin-1-yl]-ethanone |
| 9 | 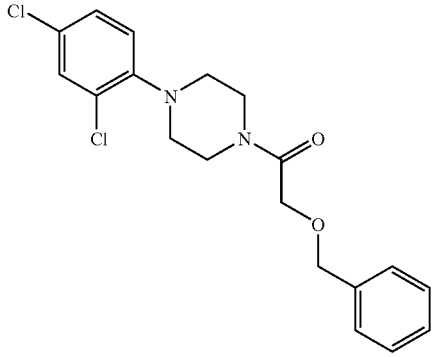 | 2-Benzyloxy-1-[4-(2,4-dichlorophenyl)-piperazin-1-yl]-ethanone |
| 10 | 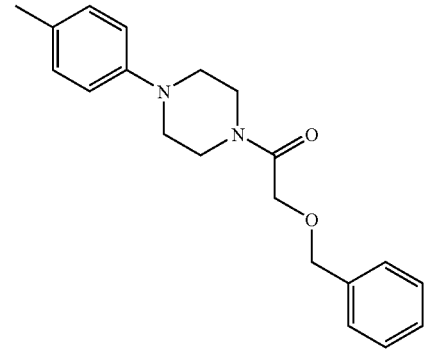 | 2-Benzyloxy-1-(4-p-tolyl-piperazin-1-yl)-ethanone |
| 11 | 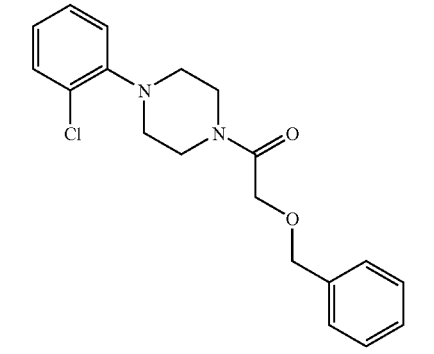 | 2-Benzyloxy-1-[4-(2-chlorophenyl)-piperazin-1-yl]-ethanone |

-continued

| No. | Structure | Name |
|---|---|---|
| 12 | 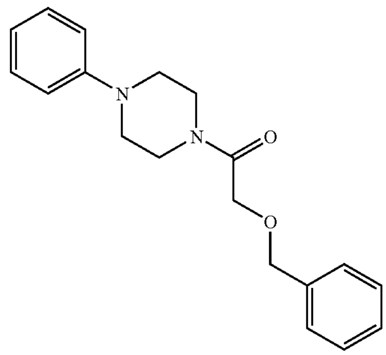 | 2-Benzyloxy-1-(4-phenyl-piperazin-1-yl)-ethanone |
| 13 | 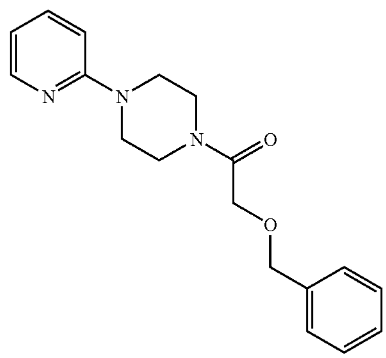 | 2-Benzyloxy-1-(4-pyridin-2-yl-piperazin-1-yl)-ethanone |
| 14 | 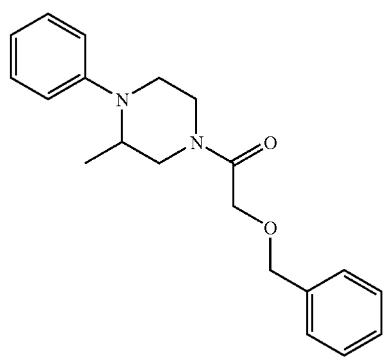 | 2-Benzyloxy-1-(3-methyl-4phenyl-piperazin-1-yl)-ethanone |
| 15 | 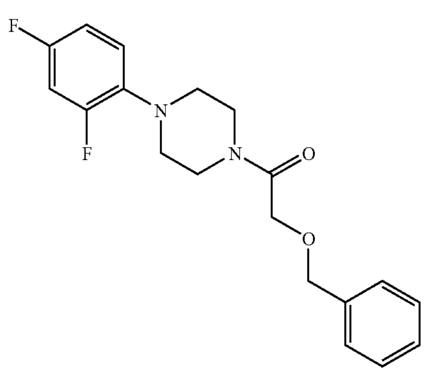 | 2-Benzyloxy-1-[4-(2,4-difluoro-phenyl)-piperazin-1-yl]-ethanone |

| No. | Structure | Name |
|---|---|---|
| 16 | 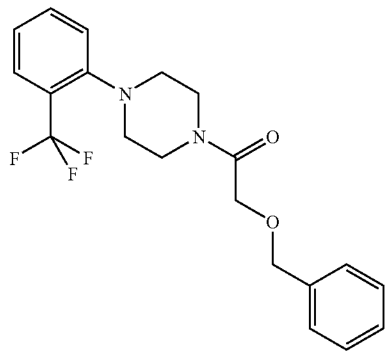 | 2-Benzyloxy-1-[4-(2-trifluoromethyl-phenyl)-piperazin-1-yl]-ethanone |
| 17 | 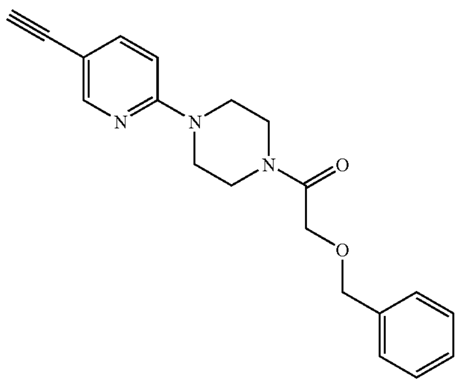 | 2-Benzyloxy-1-[4-(5-ethynyl-pyridin-2-yl)-piperazin-1-yl]-ethanone |
| 18 | 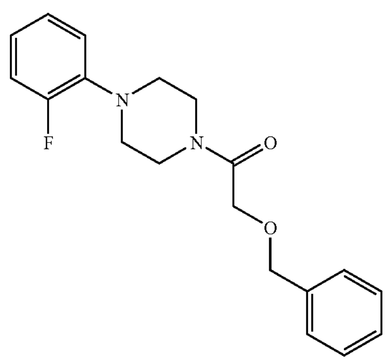 | 2-Benzyloxy-1-[4-(2-fluorophenyl)-piperazin-1-yl]-ethanone |
| 19 | 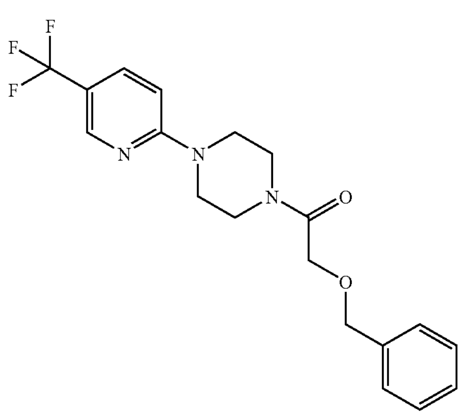 | 2-Benzyloxy-1-[4-(5-trifluoromethyl-pyridin-2-yl)-piperazin-1-yl]-ethanone |

-continued

| No. | Structure | Name |
|---|---|---|
| 20 | 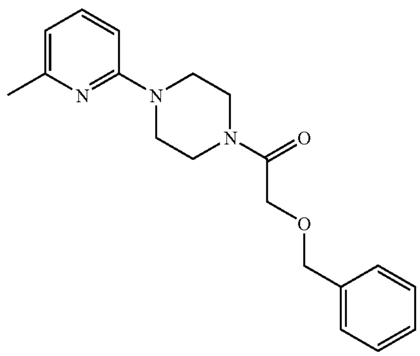 | 2-Benzyloxy-1-[4-(6-methyl-pyridin-2-yl)-piperazin-1-yl]-ethanone |
| 21 | 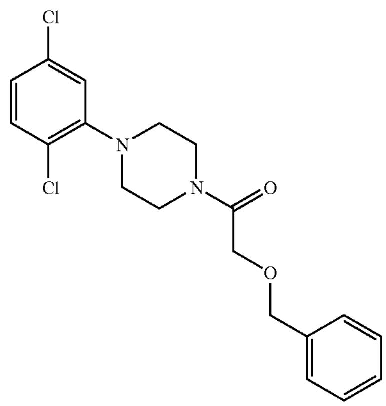 | 2-Benzyloxy-1-[4-(2,5-dichlorophenyl)-piperazin-1-yl]-ethanone |
| 22 | 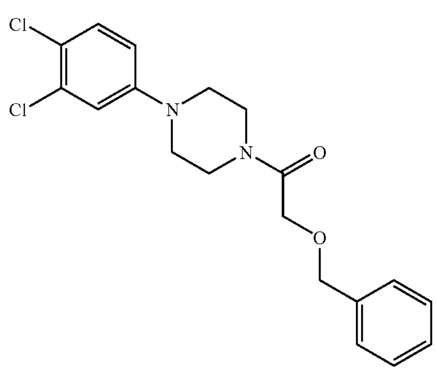 | 2-Benzyloxy-1-[4-(3,4-dichloro-phenyl)-piperazin-1-yl]-ethanone |
| 23 | 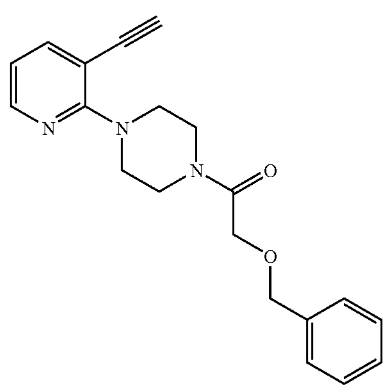 | 2-[4-(2-Benzyloxy-acetyl)-piperazin-1-yl]-nicotinonitrile |

-continued

| No. | Structure | Name |
| --- | --- | --- |
| 24 | 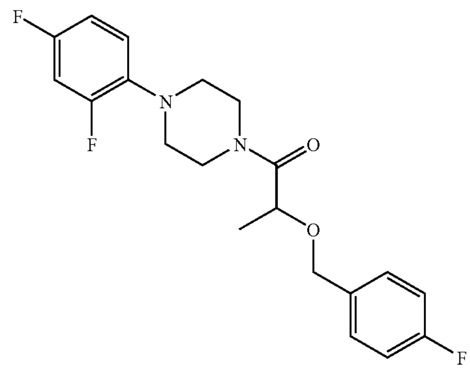 | 1-[4-(2,4-difluoro-phenyl)-piperazin-1-yl]-2-(4-fluoro-benzyloxy)-propan-1-one |
| 25 | 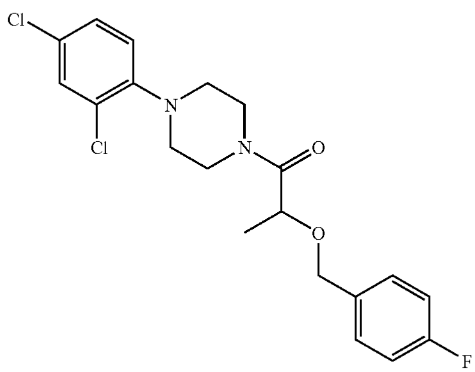 | 1-[4-(2,4-dichloro-phenyl)-piperazin-1-yl]-2-(4-fluoro-benzyloxy)-propan-1-one |
| 26 | 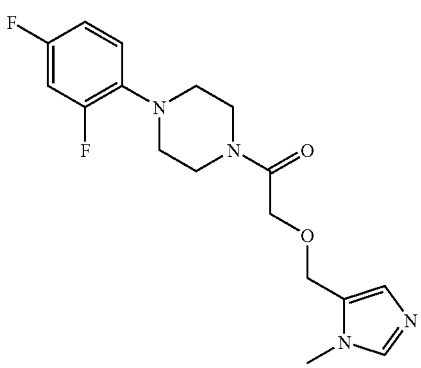 | 1-[4-(2,4-difluoro-phenyl)-piperazin-1-yl]-2-(3-methyl-3H-imidazol-4-ylmethoxy)-propan-1-one |
| 27 | 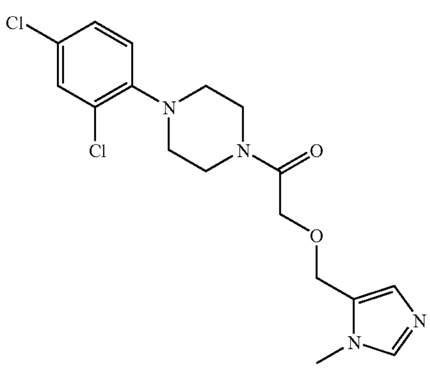 | 1-(4-(2,4-chloro-phenyl)-piperazin-1-yl]-2-(3-methyl-3H-imidazol-4-ylmethoxy)-propan-1-one |

-continued

| No. | Structure | Name |
|---|---|---|
| 28 | 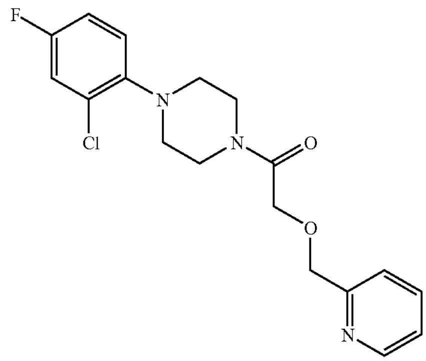 | 1-[4-(2-Chloro-4-fluoro-phenyl)-piperazin-1-yl]-2-(pyridin-2-ylmethyloxy)-ethanone |
| 29 | 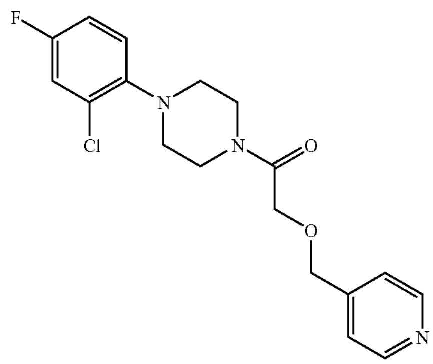 | 1-[4-(2-Chloro-4-fluoro-phenyl)-piperazin-1-yl]-2-(pyridin-4-ylmethyloxy)-ethanone |
| 30 | 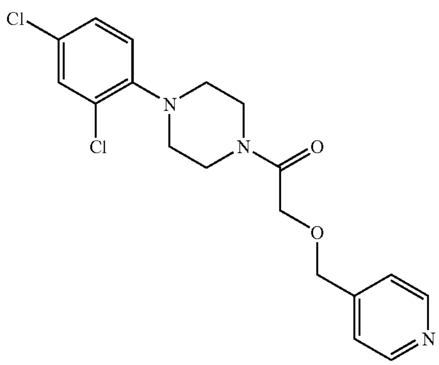 | 1-[4-(2,4-Dichloro-phenyl)-piperazin-1-yl]-2-(pyridin-4-ylmethyloxy)-ethanone |
| 31 | 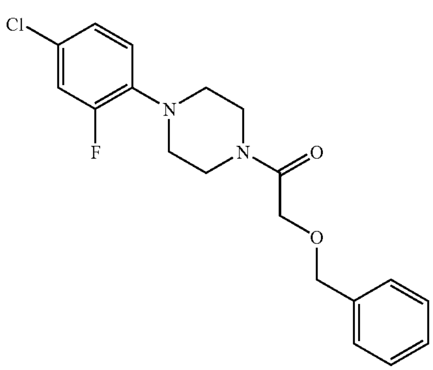 | 2-Benzyloxy-1-[4-(4-Fluoro-2-chloro-phenyl)-piperazin-1-yl]-ethanone |

-continued

| No. | Structure | Name |
|---|---|---|
| 32 | 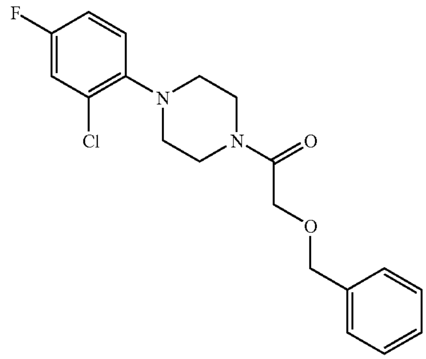 | 2-Benzyloxy-1-[4-(2-Chloro-4-fluoro-phenyl)-piperazin-1-yl]-ethanone |
| 33 | 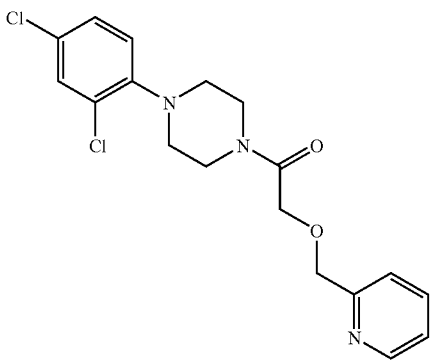 | 1-[4-(2,4-dichloro-phenyl)-piperazin-1-yl]-2-(pyridin-2-ylmethoxy)-ethanone |
| 34 | 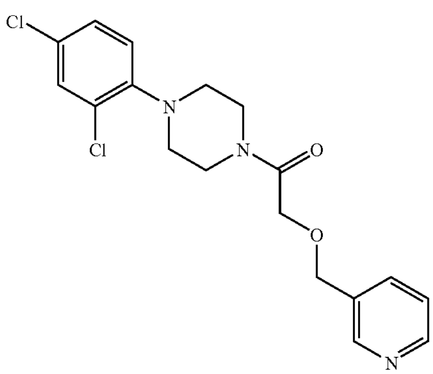 | 1-[4-(2,4-dichloro-phenyl)-piperazin-1-yl]-2-(pyridin-3-ylmethoxy)-ethanone |
| 35 | 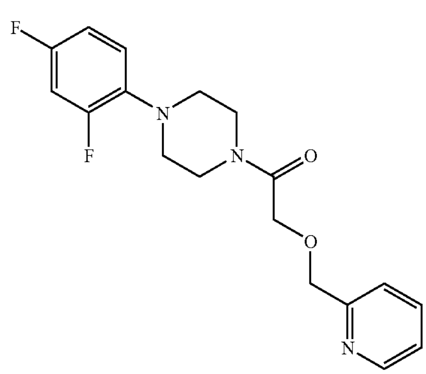 | 1-[4-(2,4-Difluoro-phenyl)-piperazin-1-yl]-2-(pyridin-2-ylmethoxy)-ethanone |

| No. | Structure | Name |
|---|---|---|
| 36 | 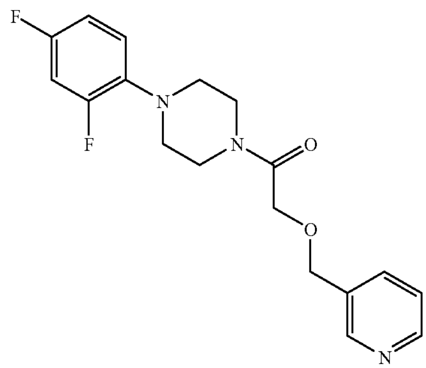 | 1-[4-(2,4-Difluoro-phenyl)-piperazin-1-yl]-2-(pyridin-3-ylmethoxy)-ethanone |
| 37 | 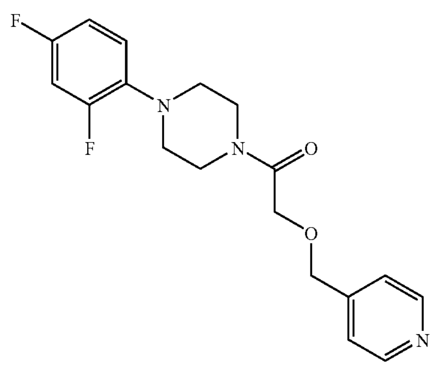 | 1-[4-(2,4-dichloro-phenyl)-piperazin-1-yl]-2-(pyridin-4-ylmethoxy)-ethanone |
| 38 | 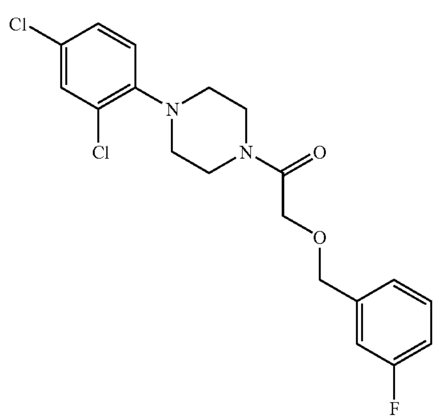 | 1-[4-(2,4-Dichloro-phenyl)-piperazin-1-yl]-2-(3-fluoro-benzyloxy)-ethanone |
| 39 | 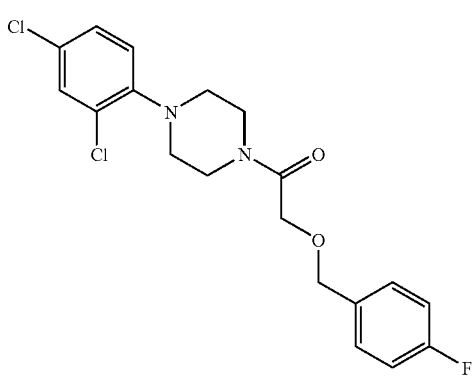 | 1-[4-(2,4-Dichloro-phenyl)-piperazin-1-yl]-2-(4-fluoro-benzyloxy)-ethanone |

-continued

| No. | Structure | Name |
|---|---|---|
| 40 | 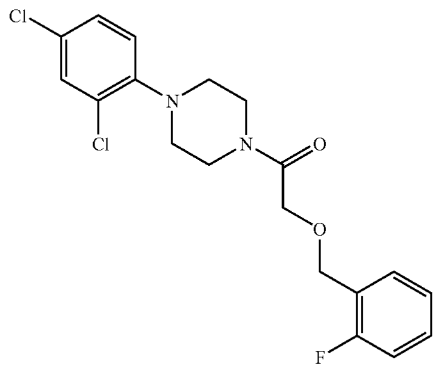 | 1-[4-(2,4-Dichloro-phenyl)-piperazin-1-yl]-2-(2-fluoro-benzyloxy)-ethanone |
| 41 | 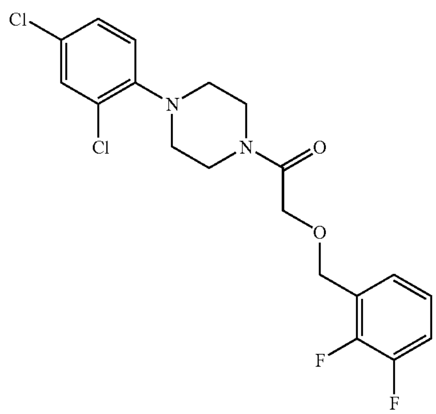 | 1-[4-(2,4-Dichloro-phenyl)-piperazin-1-yl]-2-(2,3-difluoro-benzyloxy)-ethanone |
| 42 | 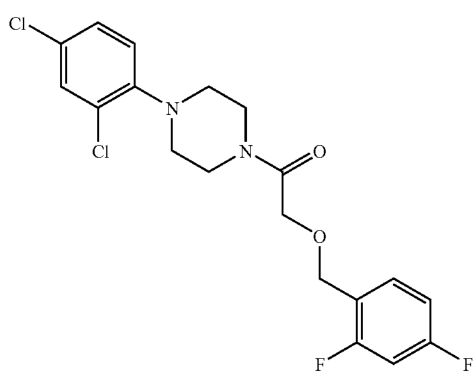 | 1-[4-(2,4-Dichloro-phenyl)-piperazin-1-yl]-2-(2,4-difluoro-benzyloxy)-ethanone |
| 43 | 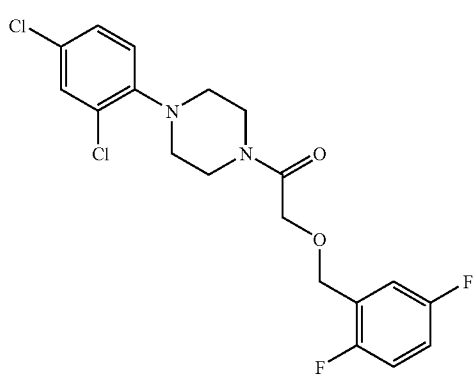 | 1-[4-(2,4-Dichloro-phenyl)-piperazin-1-yl]-2-(2,5-difluoro-benzyloxy)-ethanone |

| No. | Structure | Name |
|---|---|---|
| 44 | 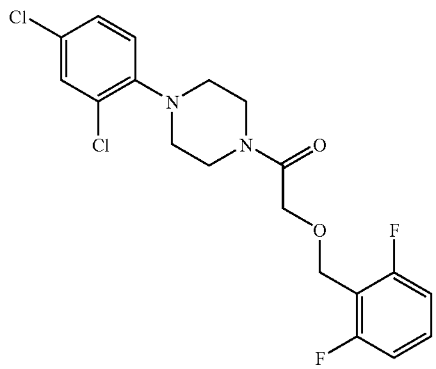 | 1-[4-(2,4-Dichloro-phenyl)-piperazin-1-yl]-2-(2,6-difluoro-benzyloxy)-ethanone |
| 45 | 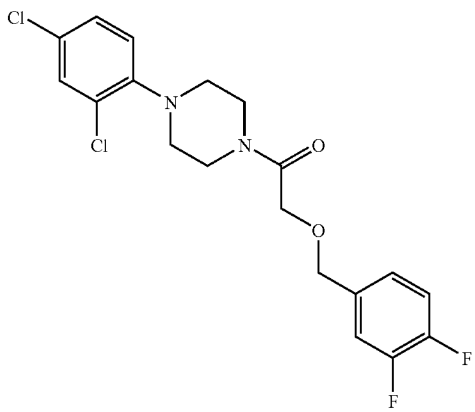 | 1-[4-(2,4-Dichloro-phenyl)-piperazin-1-yl]-2-(3,4-difluoro-benzyloxy)-ethanone |
| 46 | 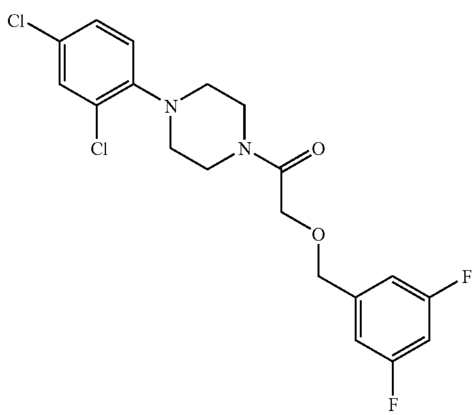 | 1-[4-(2,4-Dichloro-phenyl)-piperazin-1-yl]-2-(3,5-difluoro-benzyloxy)-ethanone |
| 47 | 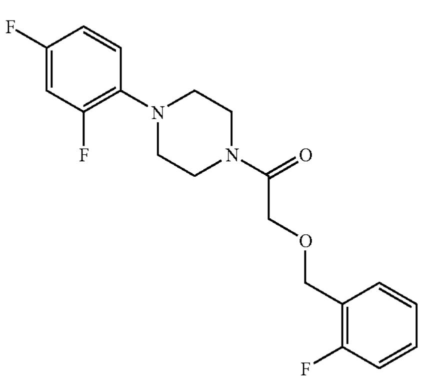 | 1-[4-(2,4-Difluoro-phenyl)-piperazin-1-yl]-2-(2-fluoro-benzyloxy)-ethanone |

-continued

| No. | Structure | Name |
|---|---|---|
| 48 | 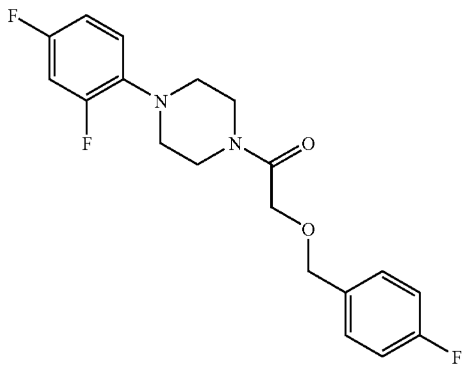 | 1-[4-(2,4-Difluoro-phenyl)-piperazin-1-yl]-2-(4-fluoro-benzyloxy)-ethanone |
| 49 | 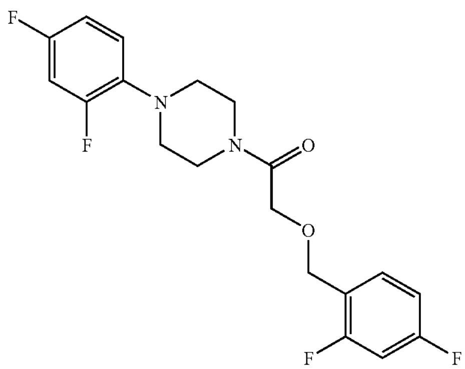 | 2-(2,4-Difluoro-benzyloxy)-1-[4-(2,4-difluoro-phenyl)-piperazin-1-yl]-ethanone |
| 50 | 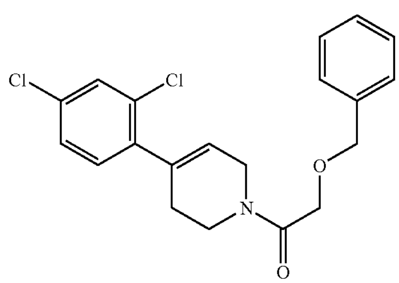 | 2-Benzyloxy-1-[4-(2,4-dichloro-phenyl)-3,6-dihydro-2H-pyridin-1-yl]-ethanone |
| 51 | 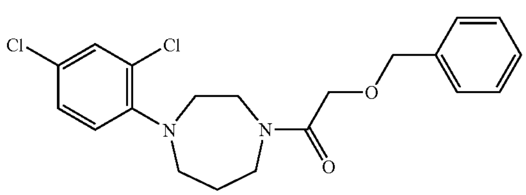 | 2-Benzyloxy-1-[4-(2,4-dichloro-phenyl)-[1,4]diazepan-1-yl]-ethanone |
| 52 | 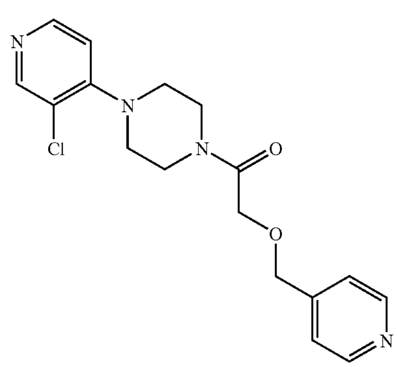 | 1-[4-(3-Chloro-pyridin-4-yl)-piperazin-1-yl]-2-(pyridin-4-ylmethoxy)-ethanone |

-continued

| No. | Structure | Name |
|---|---|---|
| 53 | 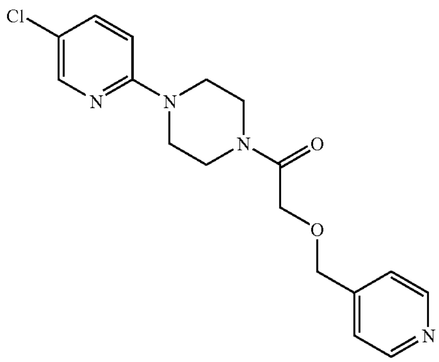 | 1-[4-(5-Chloro-pyridin-2-yl)-piperazin-1-yl]-2-(pyridin-4-ylmethoxy)-ethanone |
| 54 | 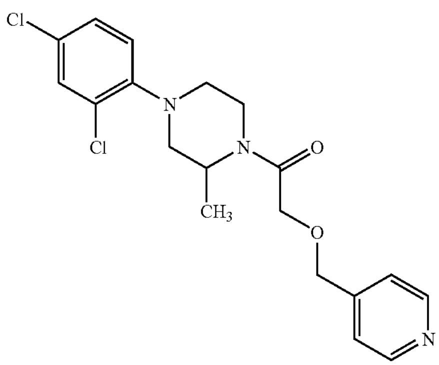 | 1-[4-(2,4-Dichloro-phenyl)-2-methyl-piperazin-1-yl]-2-(pyridin-4-ylmethoxy)-ethanone |
| 55 | 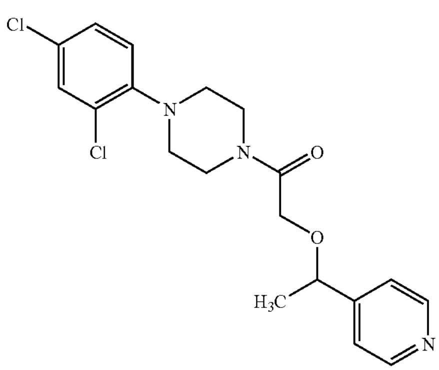 | 1-[4-(2,4-Dichloro-phenyl)-piperazin-1-yl]-2-(1-pyridin-4-yl-ethoxy)-ethanone |
| 56 | 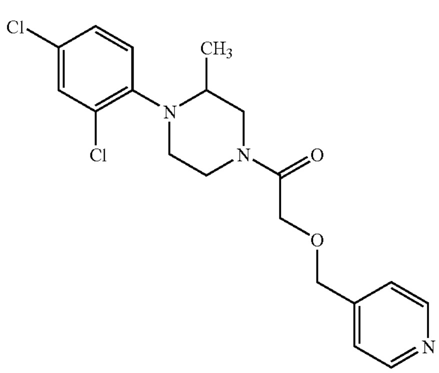 | 1-[4-(2,4-Dichloro-phenyl)-3-methyl-piperazin-1-yl]-2-(pyridin-4-ylmethoxy)-ethanone |

| No. | Structure | Name |
|---|---|---|
| 57 | 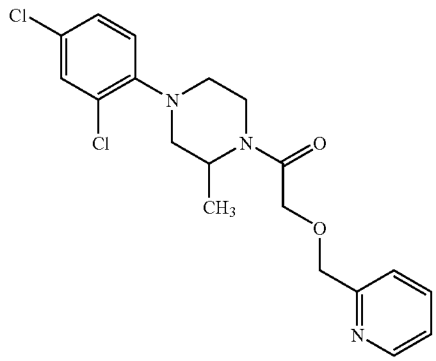 | 1-[4-(2,4-Dichloro-phenyl)-2-methyl-piperazin-1-yl]-2-(pyridin-2-ylmethoxy)-ethanone |
| 58 | 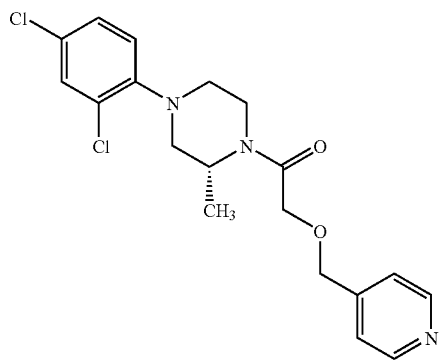 | 1-[(R)-4-(2,4-Dichloro-phenyl)-2-methyl-piperazin-1-yl]-2-(pyridin-4-ylmethoxy)-ethanone |
| 59 | 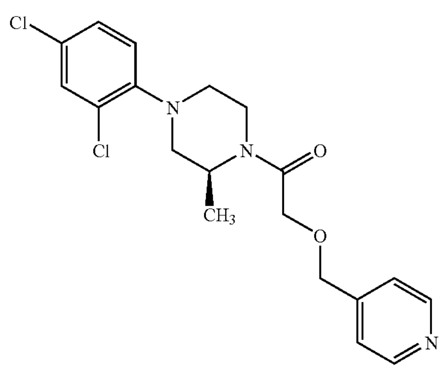 | 1-[(S)-4-(2,4-Dichloro-phenyl)-2-methyl-piperazin-1-yl]-2-(pyridin-4-ylmethoxy)-ethanone |
| 60 | 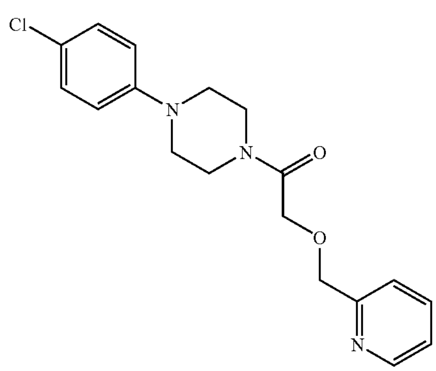 | 1-[4-(4-Chloro-phenyl)-piperazin-1-yl]-2-(pyridin-2-ylmethoxy)-ethanone |

| No. | Structure | Name |
|---|---|---|
| 61 | 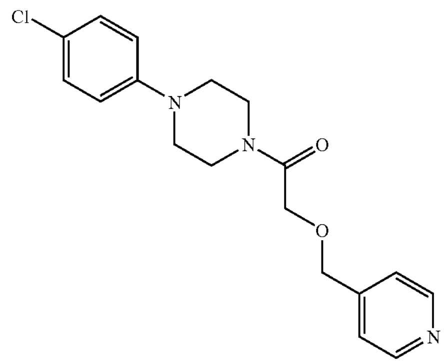 | 1-[4-(4-Chloro-phenyl)-piperazin-1-yl]-2-(pyridin-4-ylmethoxy)-ethanone |
| 62 | 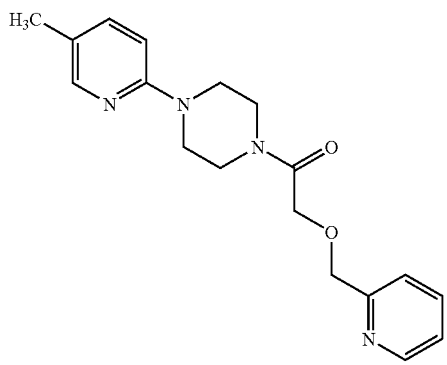 | 1-[4-(5-Methyl-pyridin-2-yl)-piperazin-1-yl]-2-(pyridin-2-ylmethoxy)-ethanone |
| 63 | 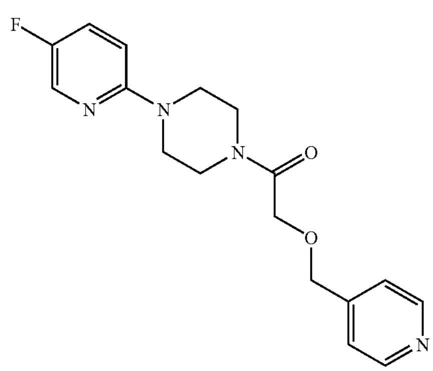 | 1-[4-(5-Fluoro-pyridin-2-yl)-piperazin-1-yl]-2-(pyridin-4-ylmethoxy)-ethanone |
| 64 | 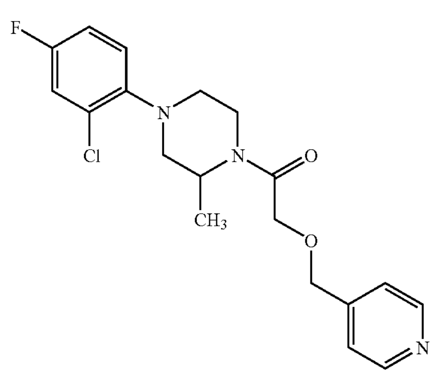 | 1-[4-(2-Chloro-4-fluoro-phenyl)-2-methyl-piperazin-1-yl]-2-(pyridin-4-ylmethoxy)-ethanone |

| No. | Structure | Name |
|---|---|---|
| 65 | 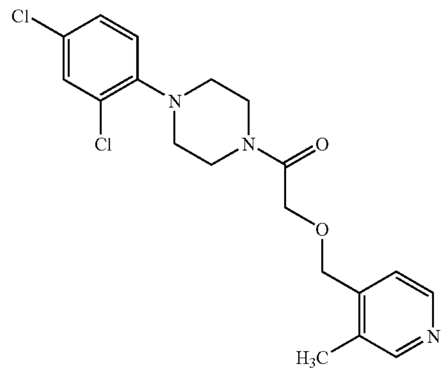 | 1-[4-(2,4-Dichloro-phenyl)-piperazin-1-yl]-2-(3-methyl-pyridin-4-ylmethoxy)-ethanone |
| 66 | 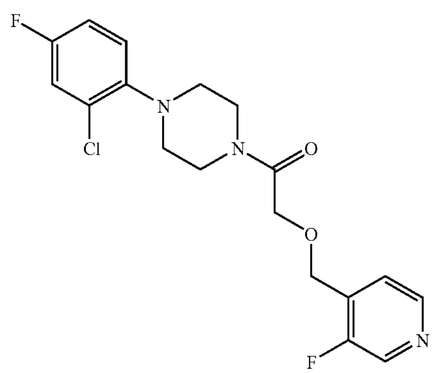 | 1-[4-(2-Chloro-4-fluoro-phenyl)-piperazin-1-yl]-2-(3-fluoro-pyridin-4-ylmethoxy)-ethanone |
| 67 | 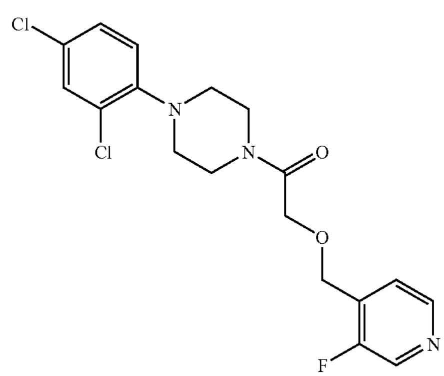 | 1-[4-(2,4-Dichloro-phenyl)-piperazin-1-yl]-2-(3-fluoro-pyridin-4-ylmethoxy)-ethanone |
| 68 | 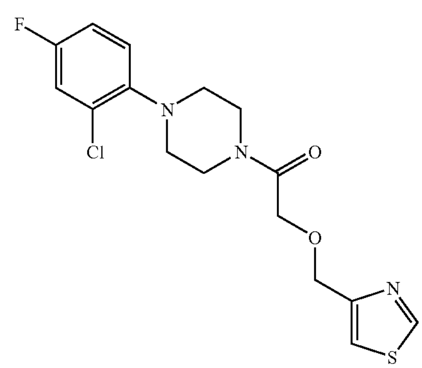 | 1-[4-(2-Chloro-4-fluoro-phenyl)-piperazin-1-yl]-2-(thiazol-4-ylmethoxy)-ethanone |

-continued

| No. | Structure | Name |
|---|---|---|
| 69 | 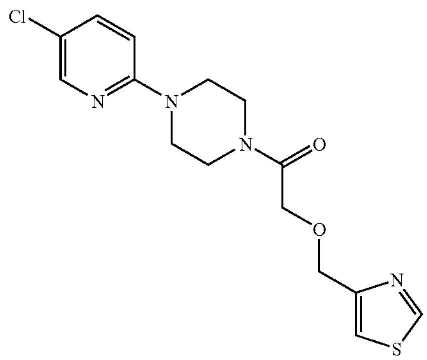 | 1-[4-(5-Chloro-pyridin-2-yl)-piperazin-1-yl]-2-(thiazol-4-ylmethoxy)-ethanone |
| 70 | 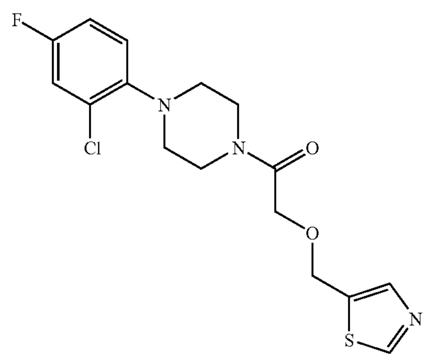 | 1-[4-(2-Chloro-4-fluoro-phenyl)-piperazin-1-yl]-2-(thiazol-5-ylmethoxy)-ethanone |
| 71 | 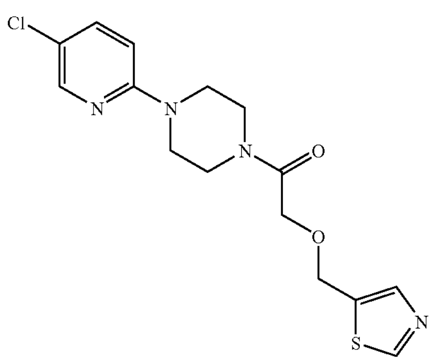 | 1-[4-(5-Chloro-pyridin-2-yl)-piperazin-1-yl]-2-(thiazol-5-ylmethoxy)-ethanone |
| 72 | 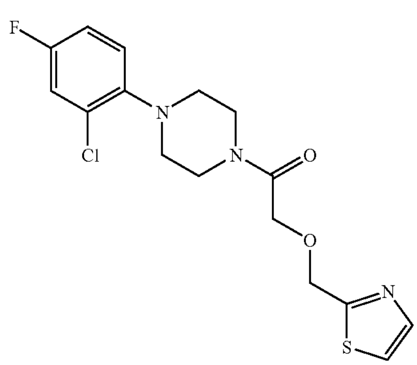 | 1-[4-(2-Chloro-4-fluoro-phenyl)-piperazin-1-yl]-2-(thiazol-2-ylmethoxy)-ethanone |

| No. | Structure | Name |
|---|---|---|
| 73 | 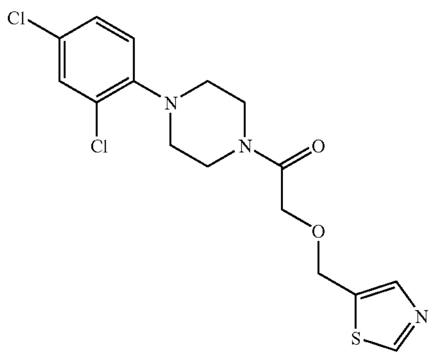 | 1-[4-(2,4-Dichloro-phenyl)-piperazin-1-yl]-2-(thiazol-5-ylmethoxy)-ethanone |
| 74 | 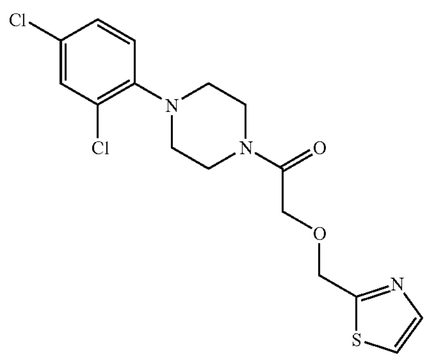 | 1-[4-(2,4-Dichloro-phenyl)-piperazin-1-yl]-2-(thiazol-2-ylmethoxy)-ethanone |
| 75 | 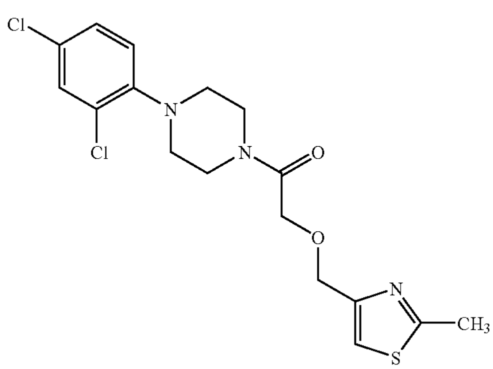 | 1-[4-(2,4-Dichloro-phenyl)-piperazin-1-yl]-2-(2-methyl-thiazol-4-ylmethoxy)-ethanone |
| 76 | 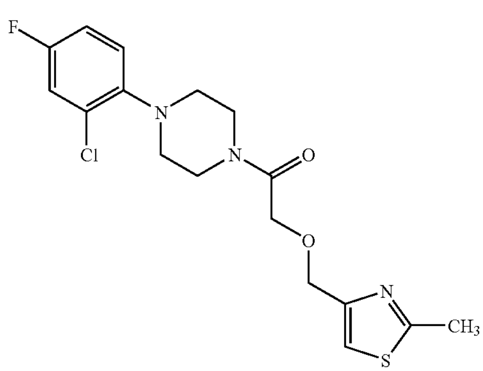 | 1-[4-(2-Chloro-4-fluoro-phenyl)-piperazin-1-yl]-2-(2-methyl-thiazol-4-ylmethoxy)-ethanone |

| No. | Structure | Name |
|---|---|---|
| 77 | 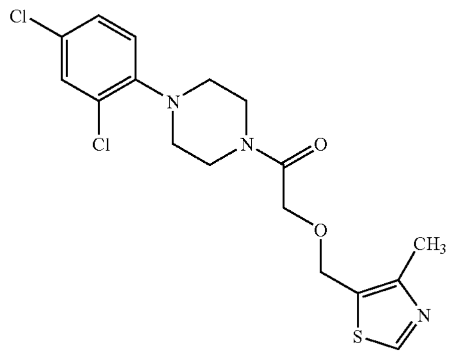 | 1-[4-(2,4-Dichloro-phenyl)-piperazin-1-yl]-2-(4-methyl-thiazol-5-ylmethoxy)-ethanone |
| 78 | 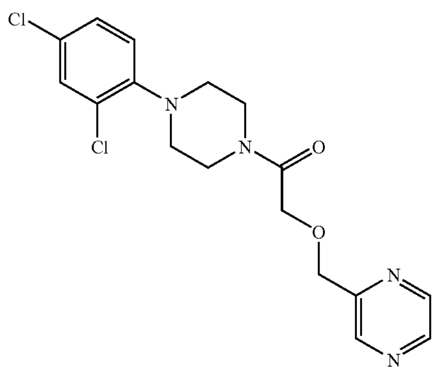 | 1-[4-(2,4-Dichloro-phenyl)-piperazin-1-yl]-2-(pyrazin-2-ylmethoxy)-ethanone |
| 79 | 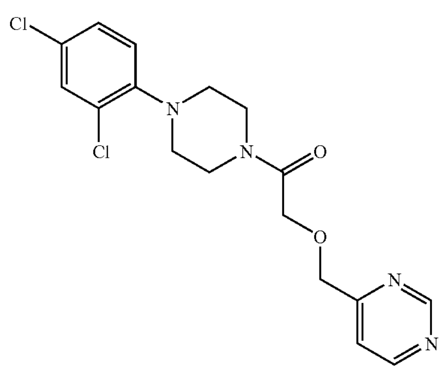 | 1-[4-(2,4-Dichloro-phenyl)-piperazin-1-yl]-2-(pyrimidin-4-ylmethoxy)-ethanone |
| 80 | 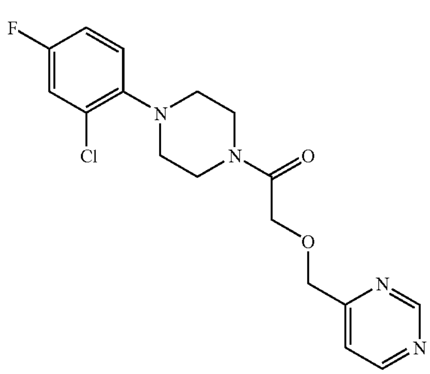 | 1-[4-(2-Chloro-4-fluoro-phenyl)-piperazin-1-yl]-2-(pyrimidin-4-ylmethoxy)-ethanone |

| No. | Structure | Name |
|---|---|---|
| 81 | 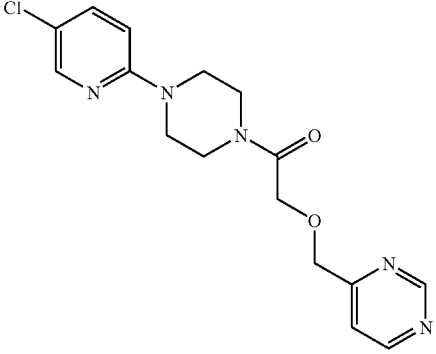 | 1-[4-(5-Chloro-pyridin-2-yl)-piperazin-1-yl]-2-(pyrimidin-4-ylmethoxy)-ethanone |
| 82 | 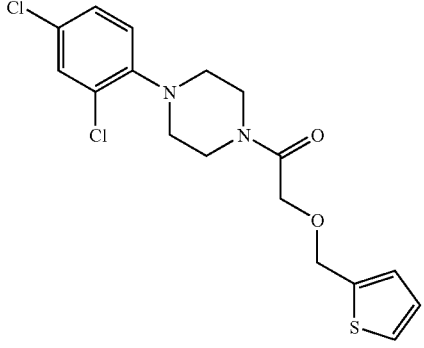 | 1-[4-(2,4-Dichloro-phenyl)-piperazin-1-yl]-2-(thiophen-2-ylmethoxy)-ethanone |
| 83 | 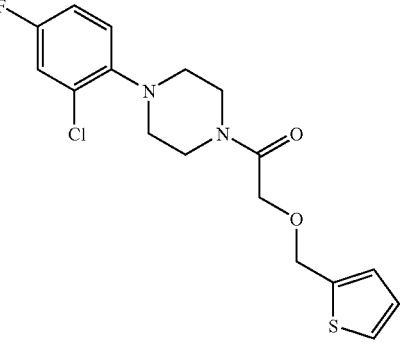 | 1-[4-(2-Chloro-4-fluoro-phenyl)-piperazin-1-yl]-2-(thiophen-2-ylmethoxy)-ethanone |
| 84 | 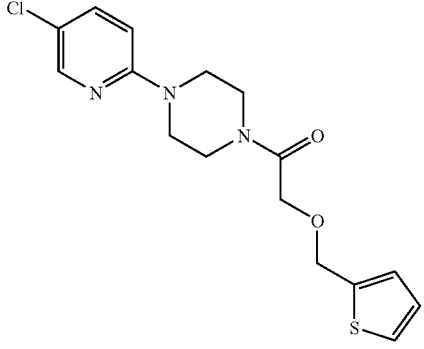 | 1-[4-(5-Chloro-pyridin-2-yl)-piperazin-1-yl]-2-(thiophen-2-ylmethoxy)-ethanone |

-continued

| No. | Structure | Name |
|---|---|---|
| 85 | 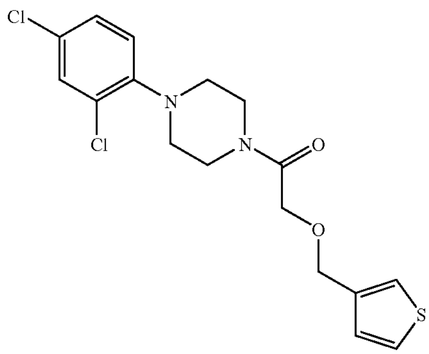 | 1-[4-(2,4-Dichloro-phenyl)-piperazin-1-yl]-2-(thiophen-3-ylmethoxy)-ethanone |
| 86 | 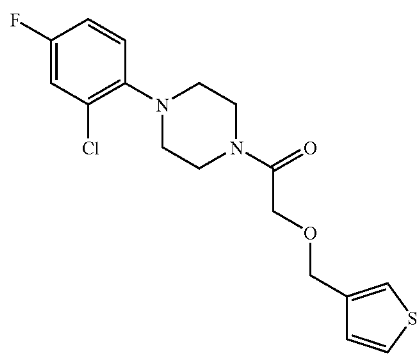 | 1-[4-(2-Chloro-4-fluoro-phenyl)-piperazin-1-yl]-2-(thiophen-3-ylmethoxy)-ethanone |
| 87 | 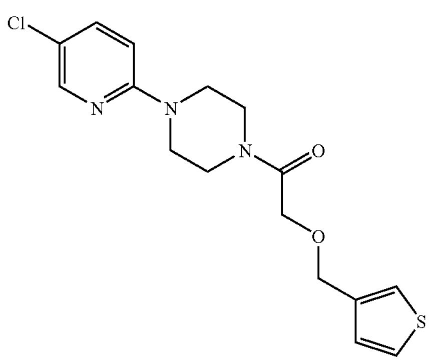 | 1-[4-(5-Chloro-pyridin-2-yl)-piperazin-1-yl]-2-(thiophen-3-ylmethoxy)-ethanone |
| 88 | 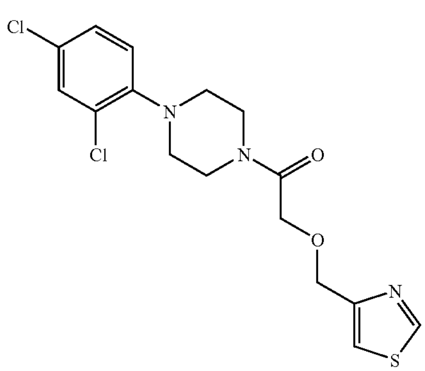 | 1-[4-(2,4-Dichloro-phenyl)-piperazin-1-yl]-2-(thiazol-4-ylmethoxy)-ethanone |

Pharmaceutical Compositions

The compounds of the present invention may be formulated into conventional pharmaceutical compositions comprising a compound of Formula I, or a pharmaceutically acceptable salt or solvate thereof and a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

It has been found that the compounds according to the present invention selectively potentiate mGluR5 receptor function. Accordingly, the compounds of the present invention are expected to be useful in the treatment of conditions associated with inhibition of mGluR5 or conditions in which downstream pathways are altered by activation of mGluR5.

The Group I mGluR receptors including mGluR5 are highly expressed in the central and peripheral nervous system and in other tissues. Thus, it is expected that the compounds of the invention are well suited for the treatment of mGluR5-mediated disorders such as acute and chronic neurological and psychiatric disorders, gastrointestinal disorders, and chronic and acute pain disorders.

The invention relates to compounds of Formula I, as defined herein, for use in therapy.

The invention relates to compounds of Formula I, as defined herein, for use in treatment of mGluR5-mediated disorders.

One embodiment of the invention relates to the use of a Formula I compound for the manufacture of a medicament for the treatment of schizophrenia.

Another embodiment of the invention relates to the use of a Formula I compound for the manufacture of a medicament for the treatment of cognition.

The invention also provides a method of treatment of mGluR5-mediated disorders and any disorder listed above, in a patient suffering from, or at risk of, said condition, which comprises administering to the patient an effective amount of a compound of Formula I, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly.

The term "disorder", unless stated otherwise, means any condition and disease associated with metabotropic glutamate receptor activity.

Non-Medical Use

In addition to their use in therapeutic medicine, the compounds of Formula I, as well as salts and hydrates of such compounds, are useful as pharmacological tools in the development and standardization of in vitro and in vivo test systems for the evaluation of the effects of inhibitors of mGluR related activity in laboratory animals such as cats, dogs, rabbits, monkeys, rats and mice, as part of the search for new therapeutics agents.

Process of Preparation

Another aspect of the present invention provides processes for preparing compounds of Formula I, or salts or hydrates thereof. Processes for the preparation of the compounds in the present invention are described below.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It also is to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations-A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, normal and reversed phase chromatography on column or rotating plate, recrystallization, distillation and liquid-liquid or solid-liquid extraction, which will be readily understood by the one skilled in the art. The definitions of substituents and groups are as in Formula I except where defined differently. The term "room temperature" and "ambient temperature" shall mean, unless otherwise specified, a temperature between 16 and 25° C.

Compounds of Formula I may be prepared according to methods shown in Schemes 1-5, below. It will be readily understood by those of skill in the art that the choice of route for a specific compound of the invention will be influenced by a number of factors including, but not limited to, availability of starting materials, the nature of any substituents etc. Unless otherwise indicated, the variables described in the following schemes have the same definitions as those given for Formula I, above.

Scheme 1

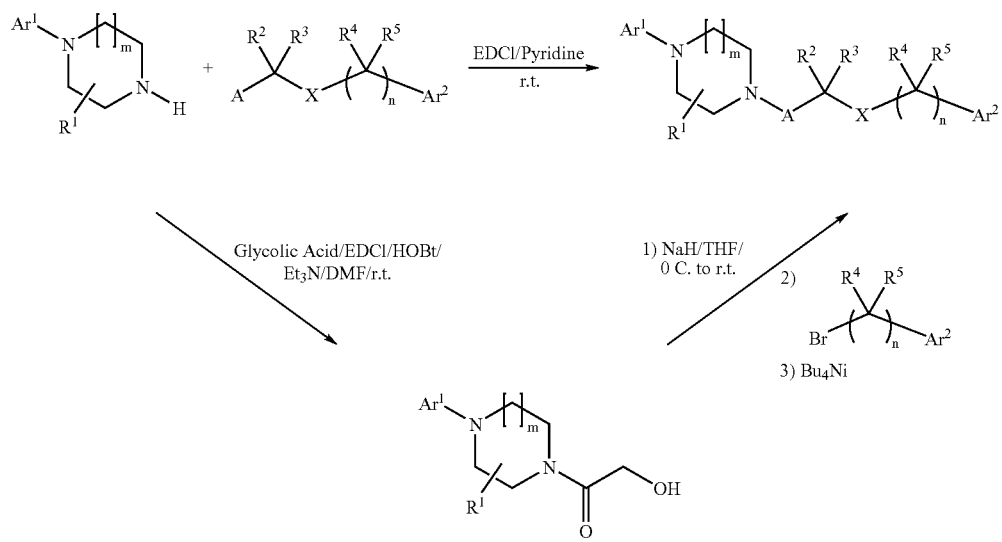

Scheme 2

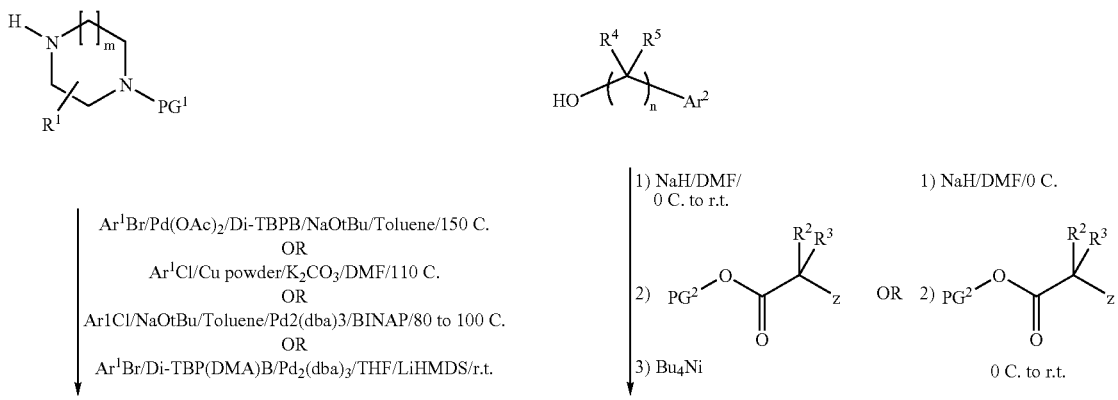

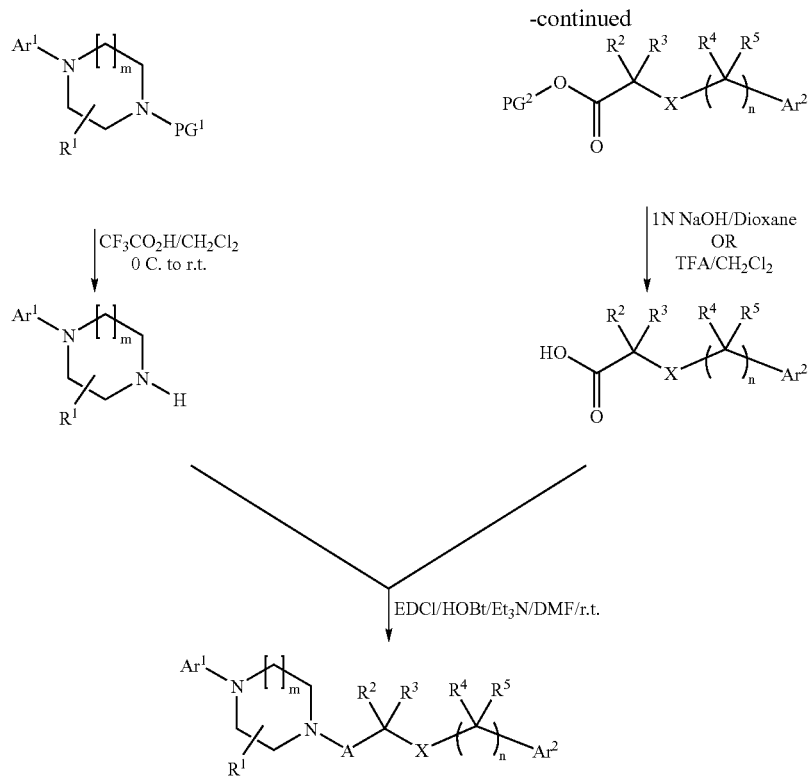
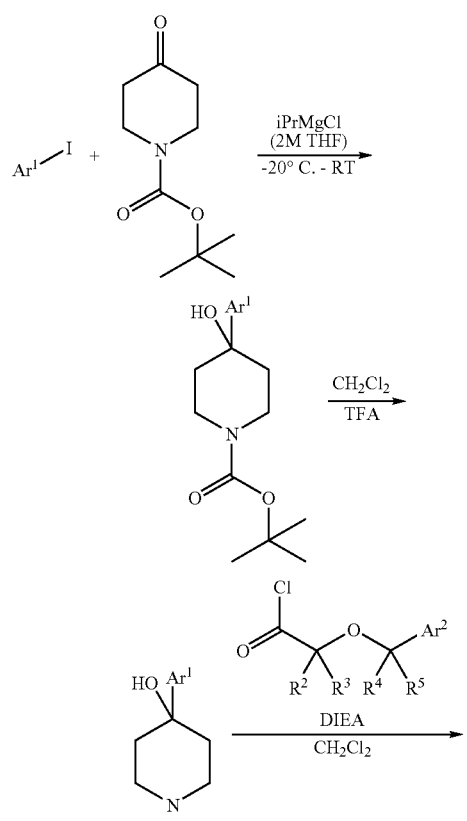
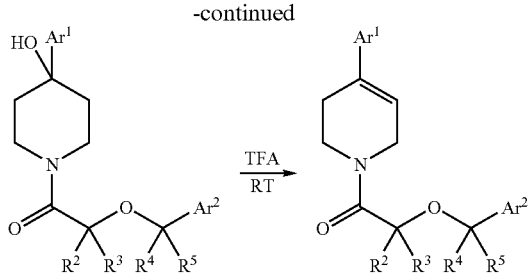
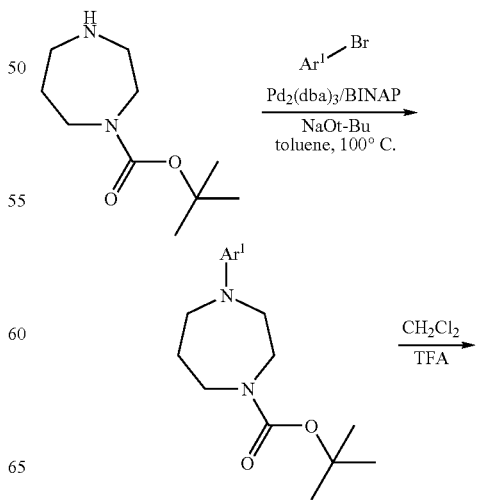

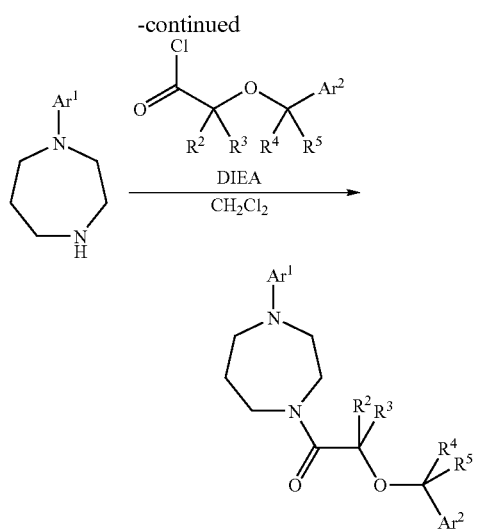

Scheme 5

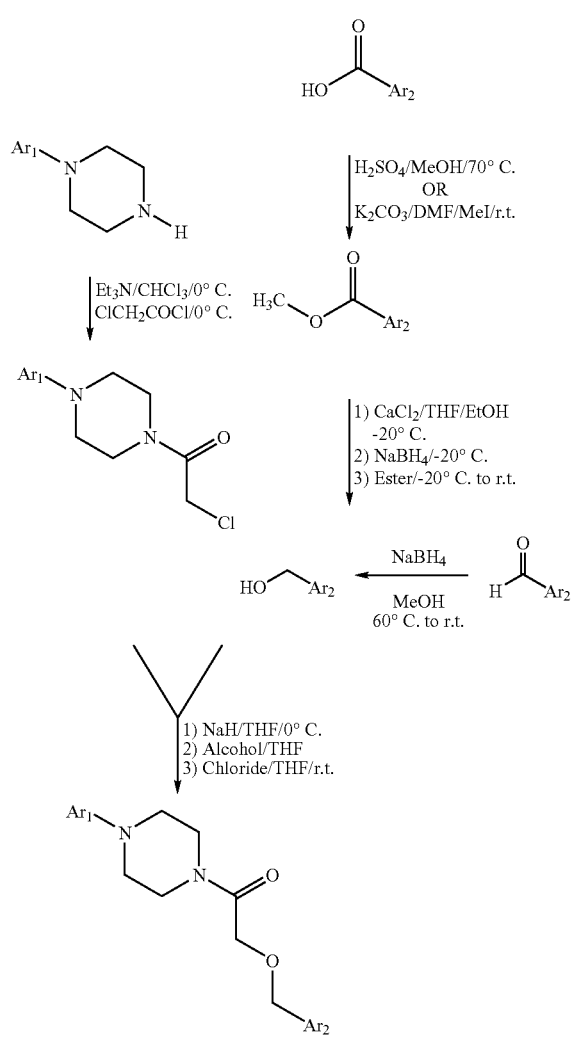

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

General Methods

All starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet). Unless otherwise indicated, in the tables below $^1$H NMR data was obtained at 300 MHz, using CDCl$_3$ as the solvent.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

Microwave heating was performed in an Emrys Optimizer from Biotage/Personal Chemistry or a Smith Synthesizer Single-mode microwave cavity producing continuous irradiation at 2450 MHz (Personal Chemistry AB, Uppsala, Sweden).

Pharmacological Assays

The pharmacological properties of the compounds of the invention can be analyzed using standard assays for functional activity. Examples of glutamate receptor assays are well known in the art as described in for example Aramori et al., Neuron 8:757 (1992), Tanabe et al., Neuron 8:169 (1992), Miller et al., J Neuroscience 15: 6103 (1995), Balazs, et al., J. Neurochemistry 69:151 (1997). The methodology described in these publications is incorporated herein by reference. Conveniently, the compounds of the invention can be studied by means of an assay that measures the mobilization of intracellular calcium, [Ca$^{2+}$]i in cells expressing mGluR5.

Intracellular calcium mobilization was measured by detecting changes in fluorescence of cells loaded with the fluorescent indicator fluo-3. Fluorescent signals were measured using the FLIPR system (Molecular Devices). A two addition experiment was used that could detect compounds that either activate or antagonize the receptor.

For FLIPR analysis, cells expressing human mGluR5d were seeded on collagen coated clear bottom 96-well plates with black sides and analysis of [Ca$^{2+}$]i mobilization was done 24 hours after seeding.

FLIPR experiments were performed using a laser setting of 0.800 W and a 0.4 second CCD camera shutter speed. Each FLIPR experiment was initiated with 160 μL of buffer present in each well of the cell plate. After each addition of the compound, the fluorescence signal was sampled 50 times at 1 second intervals followed by 3 samples at 5 second intervals. Responses were measured as the peak height of the response within the sample period.

EC$_{50}$ and IC$_{50}$ determinations were made from data obtained from 8-point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

We have validated a secondary functional assay for mGluR5d based on Inositol Phosphate ($IP_3$) turnover. $IP_3$ accumulation is measured as an index of receptor mediated phospholipase C turnover. GHEK cells stably expressing the human mGluR5d receptors were incubated with [3H] myo-inositol overnight, washed three times in HEPES buffered saline and pre-incubated for 10 minutes with 10 mM LiCl. Compounds (agonists) were added and incubated for 30 minutes at 37° C. Antagonist and potentiator activity was determined by pre-incubating test compounds for 15 minutes, then incubating in the presence of glutamate or DHPG (EC80 for antagonists, EC30 for potentiators) for 30 minutes. Reactions were terminated by the addition of perchloric acid (5%). Samples were collected and neutralized, and inositol phosphates were separated using Gravity-Fed Ion-Exchange Columns.

Generally, the compounds of the present invention were active in assays described herein at concentrations (or with $EC_{50}$ values) less than 10 µM. For example, compounds 12, 23, 48 and 58 have EC50 values of 0.6, 5.1, 0.4 and 2.3 µM, respectively.

Abbreviations

FLIPR Fluorometric Imaging Plate reader

CCD Charge Coupled Device

CRC Concentration Response Curve

GHEK Human Embryonic Kidney expressing Glutamate Transporter

HEPES 4-(2-hydroxyethyl)-1-piperazineethanesulfonic acid (buffer)

$IP_3$ inositol triphosphate

DHPG 3,5-dihydroxyphenylglycine;

EXAMPLE 1.1

2-Benzyloxy-1-[4-(4-fluorophenyl)-piperazin-1-yl]-ethanone

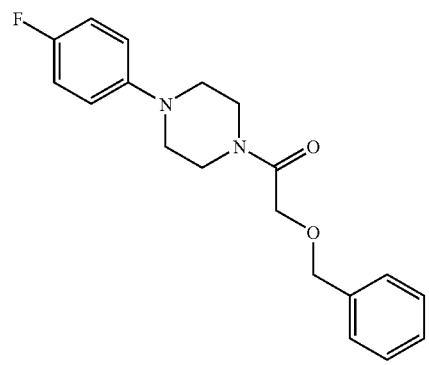

General Procedure: To a screw-cap vial was added benzyloxyacetic acid (70 mg, 0.42 mmol), 1-(3-dimthylaminopropyl)-3-ethylcarbodiimide hydrochloride (88.8 mg, 0.46 mmol), 1-(4-fluorophenyl)piperazine (83.5 mg, 0.46 mmol) and pyridine (2 mL). The resulting mixture was stirred at room temperature overnight. Saturated aqueous sodium bicarbonate (7 mL) and ethyl acetate (7 mL) were added to the reaction mixture. The organic phase was separated, washed with water (3×7 mL), dried over anhydrous sodium sulfate and concentrated in vacuo. The crude product was purified on silica gel using 100% dichloromethane to ethyl acetate:dichloromethane=1:9 in a gradient fashion, to give the desired product as an off-white solid (55.5 mg, 27%). $^1$H NMR (300 MHz, $CDCl_3$): δ 7.37 (m, 5H), 7.00 (m, 2H), 6.89 (m, 2H), 4.62 (s, 2H), 4.23 (s, 2H), 3.78 (t, 2H), 3.66 (t, 2H), 3.06 (q, 4H)

In a similar fashion the following compounds were synthesized, where the starting materials were commercially available.

| 1.2 | 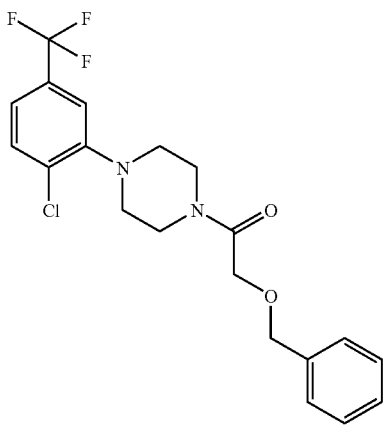 | 2-Benzyloxy-1-[4-(2-chloro-5-trifluoro methyl-phenyl)-piperazin-1-yl]-ethanone | 108.2 mg (62%) yellow oil |
|---|---|---|---|
| NMR | 7.37 (m, 6 H), 7.17 (d, 1 H), 6.96 (dd, 1 H), 4.62 (s, 2 H), 4.23 (s, 2 H), 3.78 (t, 2 H), 3.67 (t, 2 H), 3.17 (q, 4 H) | | |

| 1.3 | 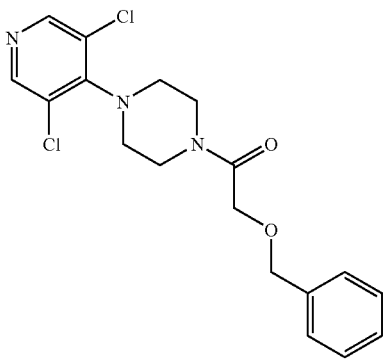 | 2-Benzyloxy-1-[4-(3,5-dichloro-pyridin-4-yl)-piperazin-1-yl]-ethanone | 88.4 mg (55%) clear oil |
|---|---|---|---|
| NMR | 8.38 (s, 2 H), 7.37 (m, 5 H), 4.65 (s, 2 H), 4.25 (s, 2 H), 3.79 (t, 2 H), 3.66 (t, 2 H), 3.33 (q, 4 H) | | |
| 1.4 | 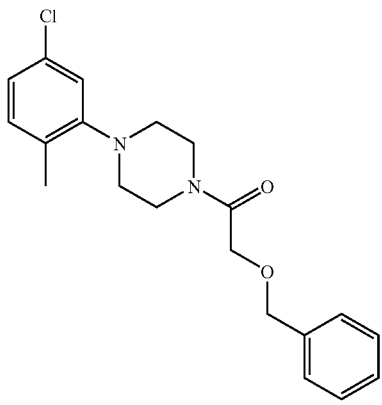 | 2-Benzyloxy-1-[4-(5-chloro-2-methyl-phenyl)-piperazin-1-yl]-ethanone | 64.3 mg (43%) yellow oil |
| NMR | 7.38 (m, 5 H), 7.12 (d, 1 H), 7.01 (dd, 1 H), 6.92 (d, 1 H), 4.65 (s, 2 H), 4.25 (s, 2 H), 3.78 (t, 2 H), 3.65 (t, 2 H), 2.86 (bm, 4 H), 2.28 (s, 3 H) | | |
| 1.5 | 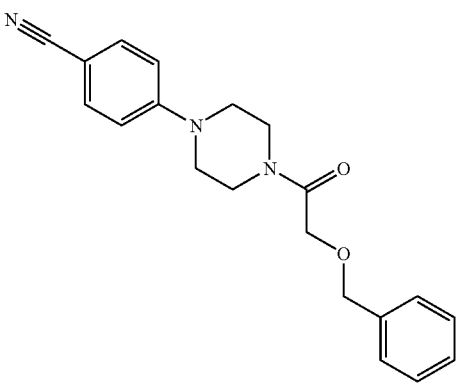 | 4-[4-(2-Benzyloxyacetyl)-piperazin-1-yl]-benzonitrile | 70.8 mg (50%) off white solid |
| NMR | 7.55 (d, 2 H), 7.37 (m, 5 H), 6.86 (d, 2 H), 4.63 (s, 2 H), 4.24 (s, 2 H), 3.78 (t, 2 H), 3.69 (t, 2 H), 3.34 (q, 4 H) | | |

| | | | |
|---|---|---|---|
| 1.6 | 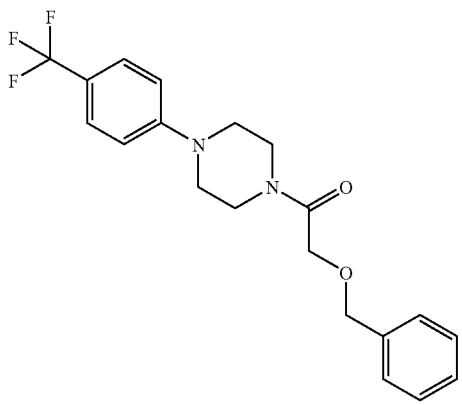 | 2-Benzyloxy-1-[4-(4-trifluoromethyl-phenyl)-piperazin-1-yl]-ethanone | 92.7 mg, (58%) beige solid |
| NMR | 7.52 (d, 2 H), 7.37 (m, 5 H), 6.93 (d, 2 H), 4.63 (s, 2 H), 4.25 (s, 2 H), 3.79 (t, 2 H), 3.69 (t, 2 H), 3.28 (q, 4 H) | | |
| 1.7 | 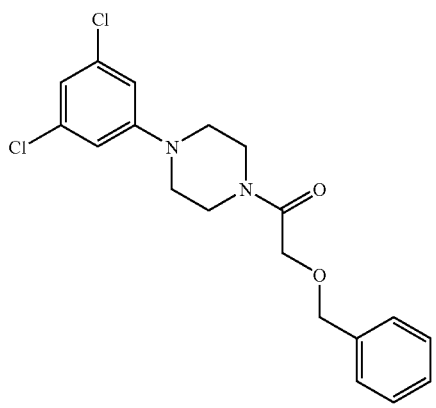 | 2-Benzyloxy-1-[4-(3,5-di-chloromethyl phenyl)-piperazin-1-yl]-ethanone | 81.3 mg, (51%) yellow oil |
| NMR | 7.39 (m, 5 H), 6.87 (t, 1 H), 6.74 (d, 2 H), 4.63 (s, 2 H), 4.24 (s, 2 H), 3.76 (t, 2 H), 3.66 (t, 2 H), 3.18 (q, 4 H) | | |
| 1.8 | 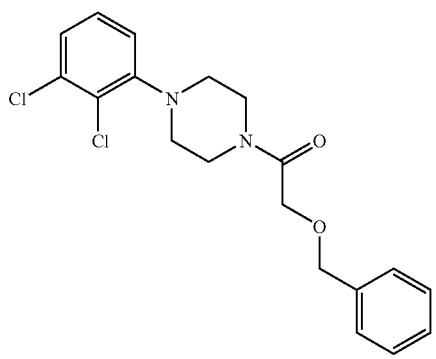 | 2-Benzyloxy-1-[4-(2,3-dichlorophenyl)-piperazin-1-yl]-ethanone | 91.1 mg (57%) yellow oil |
| NMR | 7.39 (m, 5 H), 7.20 (m, 2 H), 6.91 (dd, 1 H), 4.64 (s, 2 H), 4.25 (s, 2 H), 3.81 (t, 2 H), 3.68 (t, 2 H), 3.02 (q, 4 H) | | |

| | | | |
|---|---|---|---|
| 1.9 | 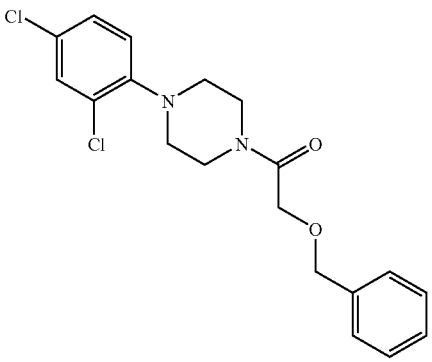 | 2-Benzyloxy-1-[4-(2,4-dichloro phenyl)-piperazin-1-yl]-ethanone | 83.3 mg (52%) clear oil |
| NMR | 7.39 (m, 6 H), 7.21 (dd, 1 H), 6.92 (dd, 1 H), 4.64 (s, 2 H), 4.24 (s, 2 H), 3.80 (t, 2 H), 3.67 (t, 2 H), 3.00 (q, 4 H) | | |
| 1.10 | 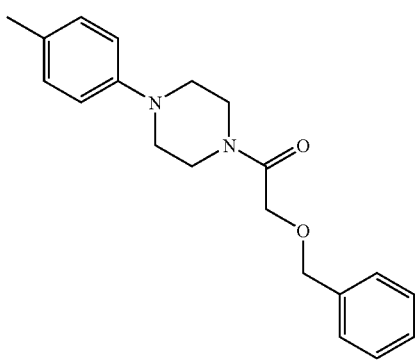 | 2-Benzyloxy-1-(4-p-tolyl-piperazin-1-yl)-ethanone | 99.8 mg, (73%) beige solid |
| NMR | 7.37 (m, 5 H), 7.11 (d, 2 H), 6.84 (d, 2 H), 4.63 (s, 2 H), 4.24 (s, 2 H), 3.79 (t, 2 H), 3.66 (t, 2 H), 3.11 (q, 4 H), 2.30 (s, 3 H) | | |
| 1.11 | 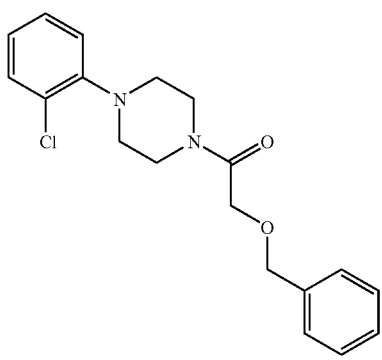 | 2-Benzyloxy-1-[4-(2-chlorophenyl)-piperazin-1-yl]-ethanone | 88.8 mg (61%) yellow oil |
| NMR | 7.39 (m, 6 H), 7.23 (m, 1 H), 7.00 (m, 2 H), 4.65 (s, 2 H), 4.25 (s, 2 H), 3.82 (t, 2 H), 3.69 (t, 2 H), 3.03 (q, 4 H) | | |

EXAMPLE 2.1

2-Benzyloxy-1-(4-phenyl-piperazin-1-yl)-ethanone

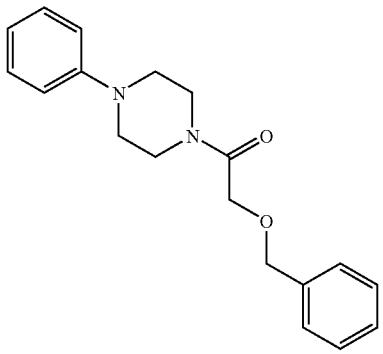

General Procedure: To a screw-cap vial was added benzyloxyacetic acid (50 mg, 0.30 mmol), 1-(3-dimthylaminopropyl)-3-ethylcarbodiimide hydrochloride (63.4 mg, 0.33 mmol), hydroxybenzotriazole (44.7 mg, 0.33 mmol), 1-phenylpiperazine (53.7 mg, 0.33 mmol) and N,N-dimethylformamide (5 mL). The resulting mixture was stirred at room temperature overnight. Water (7 mL) and ethyl acetate (7 mL) were added to the reaction mixture. The organic phase was separated, washed successively with saturated aqueous sodium bicarbonate (7 mL), water (7 mL) and brine (7 mL). The organic phase was dried over anhydrous sodium sulfate and concentrated in vacuo. The crude product was purified on silica gel using hexanes:ethyl acetate=9:1 to hexanes:ethyl acetate=0:100 in a gradient fashion, to give the desired product as an orange oil (32 mg, 34%). $^1$H NMR (300 MHz, CDCl$_3$): δ 7.34 (m, 7H), 6.96 (m, 3H), 4.64 (s, 2H), 4.25 (s, 2H), 3.82 (t, 2H), 3.70 (t, 2H), 3.19 (q, 4H)

In a similar fashion the following compounds were synthesized, where the starting materials were commercially available. Triethylamine was used as a base to neutralize, where the starting materials were available as salts.

| 2.2 | 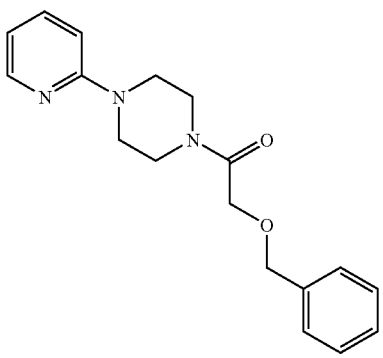 | 2-Benzyloxy-1-(4-pyridin-2-yl-piperazin-1-yl)-ethanone | 46 mg (49%) white waxy solid |
|---|---|---|---|
| NMR | 8.25 (d, 1 H), 7.63 (td, 1 H), 7.37 (m, 5 H), 6.75 (m, 2 H), 4.64 (s, 2 H), 4.24 (s, 2 H), 3.78 (t, 2 H), 3.76 (bs, 4 H), 3.58 (t, 2 H) | | |
| 2.3 | 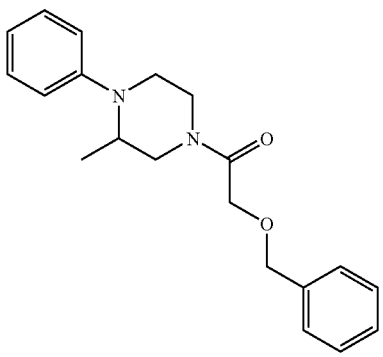 | 2-Benzyloxy-1-(3-methyl-4phenyl-piperazin-1-yl)-ethanone | 54.3 mg (56%) orange oil |
| NMR | 7.36 (m, 7 H), 6.96 (m, 3 H), 4.64 (d, 2 H), 4.26~3.16 (m, 9 H), 1.01 (dd, 3 H) | | |

-continued
| | | | |
|---|---|---|---|
| 2.4 | 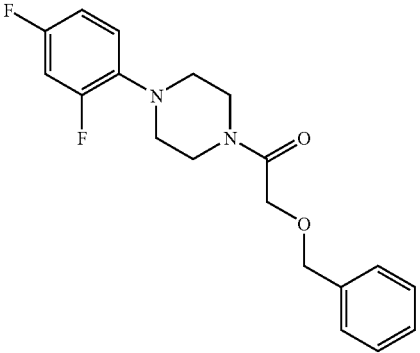 | 2-Benzyloxy-1-[4-(2,4-difluoro-phenyl)-piperazin-1-yl]-ethanone | 315 mg (91%) clear oil |
| NMR | 7.36 (m, 5 H), 6.85 (m, 3 H), 4.64 (s, 2 H), 4.24 (s, 2 H), 3.80 (t, 2 H), 3.68 (t, 2 H), 2.99 (q, 4 H) | | |
| 2.5 | 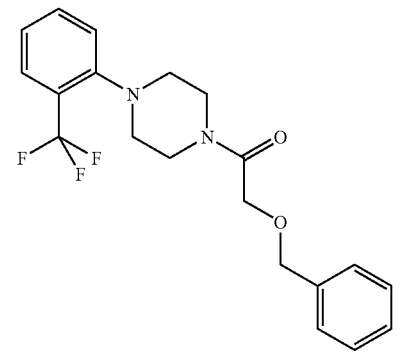 | 2-Benzyloxy-1-[4-(2-trifluoromethyl-phenyl)-piperazin-1-yl]-ethanone | 67 mg, (59%) yellow oil |
| NMR | 7.65 (d, 2 H), 7.54 (t, 1 H), 7.32 (m, 7 H), 4.64 (s, 2 H), 4.25 (s, 2 H), 3.78 (t, 2 H), 3.61 (t, 2 H), 2.91 (q, 4 H) | | |
| 2.6 | 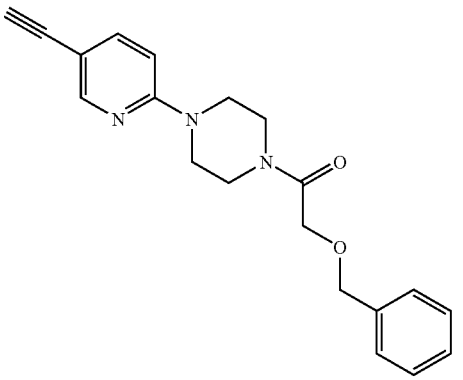 | 2-Benzyloxy-1-[4-(5-ethynyl-pyridin-2-yl)-piperazin-1-yl]-ethanone | 50.7 mg (50%) white solid |
| NMR | 8.44 (d, 1 H), 7.67 (dd, 1 H), 7.37 (m, 5 H), 6.62 (d, 1 H), 4.64 (s, 2 H), 4.25 (s, 2 H), 3.67 (m, 8 H) | | |
| 2.7 | 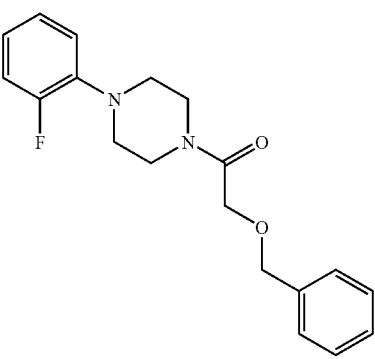 | 2-Benzyloxy-1-[4-(2-fluorophenyl)-piperazin-1-yl]-ethanone | 65.8 mg (67%) yellow oil |

| | | | |
|---|---|---|---|
| NMR | 7.37 (m, 5 H), 7.04 (m, 4 H), 4.64 (s, 2 H), 4.25 (s, 2 H), 3.81 (t, 2 H), 3.69 (t, 2 H), 3.07 (q, 4 H) | | |
| 2.8 | 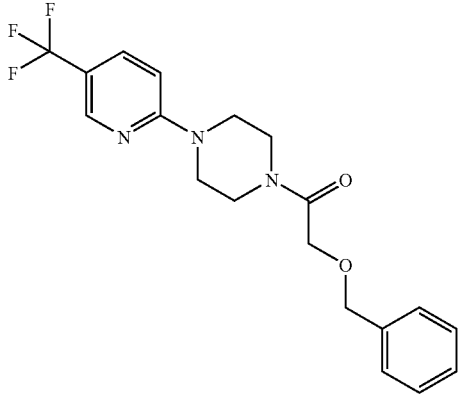 | 2-Benzyloxy-1-[4-(5-trifluoromethyl-pyridin-2-yl)-piperazin-1-yl]-ethanone | 61.8 mg, (54%) white solid |
| NMR | 8.42 (d, 1 H), 7.67 (dd, 1 H), 7.37 (m, 5 H), 6.65 (d, 1 H), 4.64 (s, 2 H), 4.25 (s, 2 H), 3.71 (m, 8 H) | | |
| 2.9 | 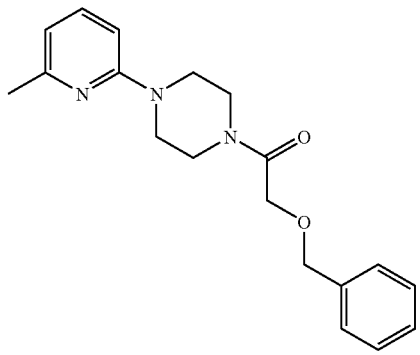 | 2-Benzyloxy-1-[4-(6-methyl-pyridin-2-yl)-piperazin-l-yl]-ethanane | 37.7 mg (39%) clear oil |
| NMR | 7.40 (m, 6 H), 7.50 (dd, 2 H), 4.64 (s, 2 H), 4.25 (s, 2 H), 3.76 (t, 2 H), 3.54 (m, 6 H), 2.42 (s, 3 H) | | |
| 2.10 | 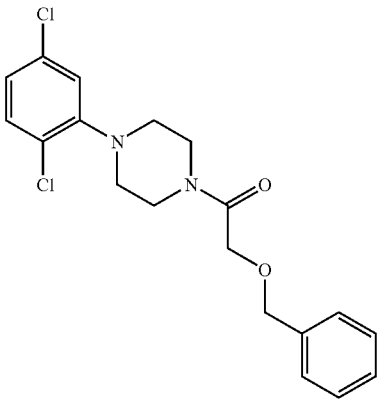 | 2-Benzyloxy-1-[4-(2,5-dichlorophenyl)-piperazin-1-yl]-ethanone | 70.8 mg, (62%) clear oil |
| NMR | 7.34 (m, 6 H), 6.97 (m, 2 H), 4.64 (s, 2 H), 4.25 (s, 2 H), 3.81 (t, 2 H), 3.69 (t, 2 H), 3.01 (q, 4 H) | | |

| 2.11 | 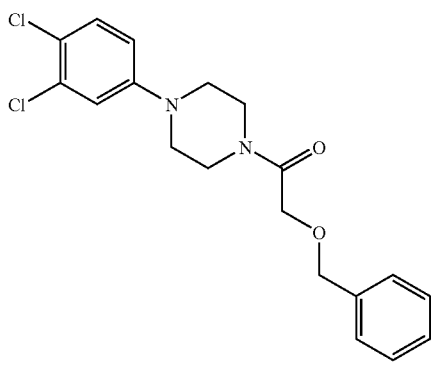 | 2-Benzyloxy-1-[4-(3,4-dichloro-phenyl)-piperazin-1-yl]-ethanone | 48 mg (47%) clear oil |
NMR 7.35 (m, 6 H), 6.96 (d, 1 H), 6.75 (dd, 1 H), 4.63 (s, 2 H), 4.24 (s, 2 H), 3.77 (t, 2 H), 3.67 (t, 2 H), 3.15 (q, 4 H)
| 2.12 | 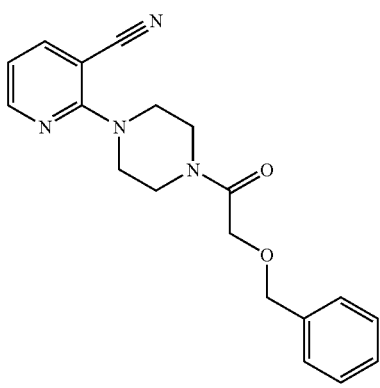 | 2-[4-(2-Benzyloxy-acetyl)-piperazin-1-yl]-nicotinonitrile | 43 mg, (47%) clear oil |
NMR 8.38 (dd, 1 H), 7.82 (dd, 1 H), 7.37 (m, 5 H), 6.84 (dd, 1 H), 4.64 (s, 2 H), 4.24 (s, 2 H), 3.74 (m, 8 H)
| 2.13 | 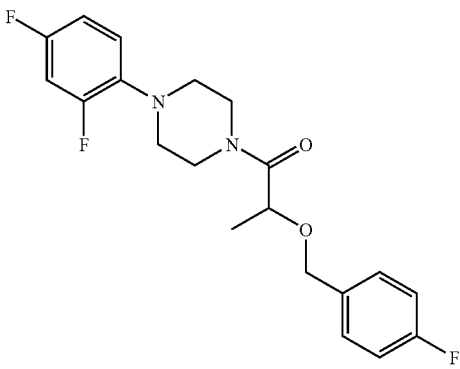 | 1-[4-(2,4-difluoro-phenyl)-piperazin-1-yl]-2-(4-fluoro-benzyloxy)-propan-1-one | 83.2 mg (58%) clear oil |
NMR 7.34 (m, 2 H), 7.06 (t, 2 H), 6.82 (m, 3 H), 4.51 (dd, 2 H), 4.39 (q, 1 H), 3.82 (m, 4 H), 3.00 (m, 4 H), 1.49 (d, 3 H)

| | | | |
|---|---|---|---|
| 2.14 | 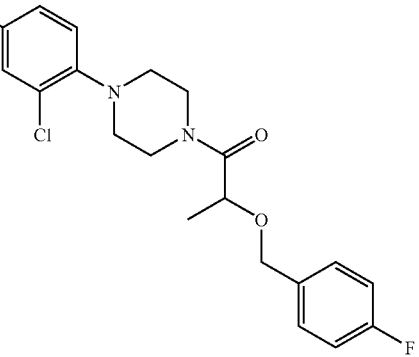 | 1-[4-(2,4-dichloro-phenyl)-piperazin-1-yl)-2-(4-fluoro-benzyloxy)-propan-1-one | 101 mg, (65%) yellow solid |
| NMR | 7.36 (m, 3 H), 7.22 (dd, 1 H), 7.06 (t, 3 H), 6.91 (d, 1 H), 4.51 (dd, 2 H), 4.38 (q, 1 H), 3.84 (m, 4 H), 3.00 (m, 4 H), 1.49 (d, 3 H) | | |
| 2.15 | 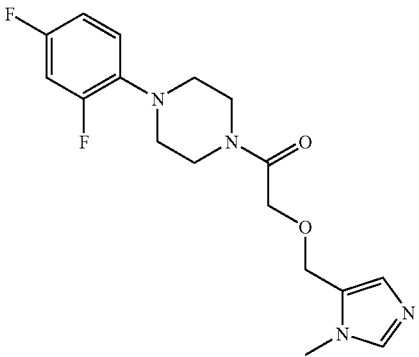 | 1-[4-(2,4-difluoro-phenyl)-piperazin-1-yl]-2-(3-methyl-3H-imidazol-4-ylmethoxy)-propan-1-one | 29 mg (24%) light yellow solid |
| NMR | 7.49 (s, 1 H), 7.07 (s, 1 H), 6.82 (m, 3 H), 4.64 (s, 2 H), 4.24 (s, 2 H), 3.80 (t, 2 H), 3.75 (s, 3 H), 3.56 (t, 2 H), 3.01 (q, 4 H) | | |
| 2.16 | 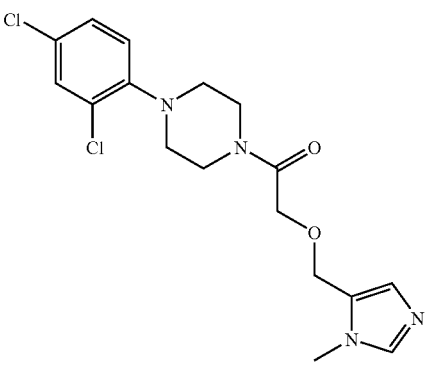 | 1-[4-(2,4-chloro-phenyl)-piperazin-1-yl]-2-(3-methyl-3H-imidazol-4-ylmethoxy)-propan-1-one | 62 mg (47%) yellow oil |
| NMR | 7.49 (s, 1 H), 7.40 (m, 1 H), 7.22 (dd, 1 H), 7.07 (m, 1 H), 6.92 (d, 1 H), 4.63 (s, 2 H), 4.18 (s, 2 H), 3.80 (t, 2 H), 3.75 (s, 3 H), 3.56 (t, 2 H), 3.00 (q, 4 H) | | |
| 2.17 | 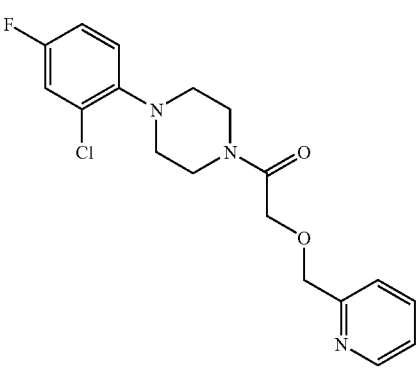 | 1-[4-(2-Chloro-4-fluoro-phenyl)-piperazin-1-yl]-2-(pyridin-2-ylmethyloxy)-ethanone | 51.5 mg, (57%) brown oil |

| | | | |
|---|---|---|---|
| NMR | 8.58 (d, 1 H), 7.73 (dt, 1 H), 7.50 (d, 1 H), 7.17 (m, 1 H), 6.98 (dd, 1 H), 6.95 (d, 2 H), 4.76 (s, 2 H), 4.36 (s, 2 H), 3.83 (t, 2 H), 3.70 (t, 2 H), 2.99 (br, 4 H) | | |
| 2.18 | 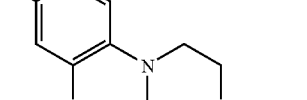 | 1-[4-(2-Chloro-4-fluoro-phenyl)-piperazin-1-yl]-2-(pyridin-4-ylmethyloxy)-ethanone | 29 mg (24%) brown oil |
| NMR | 8.62 (dd, 2 H), 7.29 (m, 2 H), 7.16 (dd, 1 H), 6.95 (dd, 2 H), 4.68 (s, 2 H), 4.31 (s, 2 H), 3.82 (t, 2 H), 3.67 (t, 2 H), 2.99 (q, 4 H) | | |
| 2.29 | 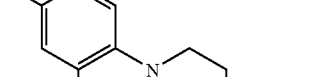 | 1-[4-(2,4-Dichloro-phenyl)-piperazin-1-yl]-2-(pyridin-4-ylmethyloxy)-ethanone | 318 mg (37%) beige solid |
| NMR | 8.62 (dd, 2 H), 7.41 (d, 1 H), 7.29 (m, 2 H), 7.22 (dd, 1 H), 6.92 (d, 1 H), 4.68 (s, 2 H), 4.30 (s, 2 H), 3.82 (t, 2 H), 3.68 (t, 2 H), 3.01 (br, 4 H) | | |
| 2.20 | 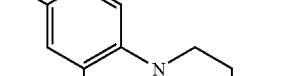 | 2-Benzyloxy-1-[4-(4-Fluoro-2-chloro-phenyl)-piperazin-1-yl]-ethanone | 76 mg (77%) clear oil |
| NMR | 7.37 (m, 5 H), 7.07 (m, 2 H), 6.83 (t, 1 H), 4.63 (s, 2 H), 4.24 (s, 2 H), 3.80 (t, 2 H), 3.68 (t, 2 H), 3.03 (q, 4 H) | | |

| | | | |
|---|---|---|---|
| 2.21 | 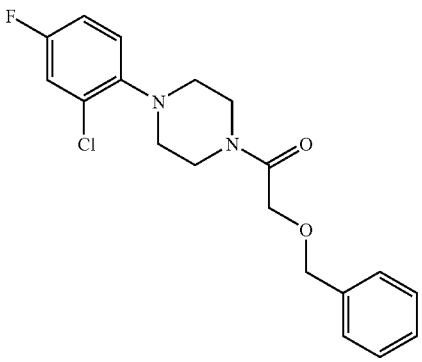 | 2-Benzyloxy-1-[4-(2-Chloro-4-fluoro-phenyl)-piperazin-1-yl]-ethanone | 60 mg (61%) clear oil |
| NMR | 7.39 (m, 5 H), 7.17 (dd, 1 H), 6.96 (dd, 2 H), 4.65 (s, 2 H), 4.25 (s, 2 H), 3.81 (t, 2 H), 3.68 (t, 2 H), 2.96 (q, 4 H) | | |
| 2.22 | 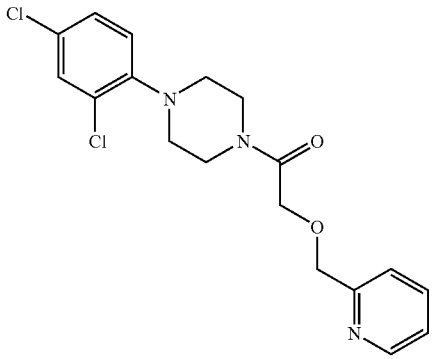 | 1-[4-(2,4-dichloro-phenyl)-piperazin-1-yl]-2-(pyridin-2-ylmethoxy)-ethanone | 62.5 mg (33.5%) brown oil |
| NMR | 8.58 (d, 1 H), 7.73 (td, 1 H), 7.49 (d, 1 H), 7.39 (d, 1 H), 7.20 (m, 2 H), 6.93 (d, 1 H), 4.76 (s, 2 H), 4.35 (s, 2 H), 3.82 (t, 2 H), 3.70 (t, 2 H), 3.01 (q, 4 H) | | |
| 2.23 | 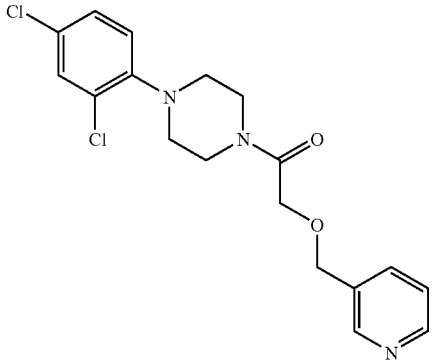 | 1-[4-(2,4-dichloro-phenyl)-piperazin-1-yl]-2-(pyridin-3-ylmethoxy)-ethanone | 38.8 mg (21%) brown oil |
| NMR | 8.62 (m, 2 H), 7.74 (m, 1 H), 7.41 (d, 1 H), 7.31 (m, 1 H), 7.20 (dd, 1 H), 6.92 (d, 1 H), 4.67 (s, 2 H), 4.28 (s, 2 H), 3.81 (t, 2 H), 3.67 (t, 2 H), 3.01 (q, 4 H) | | |
| 2.24 | 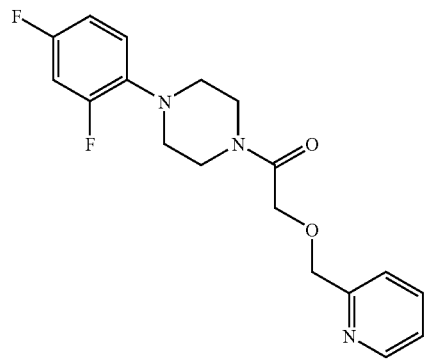 | 1-[4-(2,4-Difluoro-phenyl)-piperazin-1-yl]-2-(pyridin-2-ylmethoxy)-ethanone | 11.8 mg (6.9%) brown oil |

| | | | |
|---|---|---|---|
| NMR | 8.58 (d, 1 H), 7.73 (td, 1 H), 7.49 (d, 1 H), 7.26 (m, 1 H), 6.83 (m, 3 H), 4.76 (s, 2 H), 4.35 (s, 2 H), 3.82 (t, 2 H), 3.70 (t, 2 H). 3.02 (q, 4 H) | | |
| 2.25 | 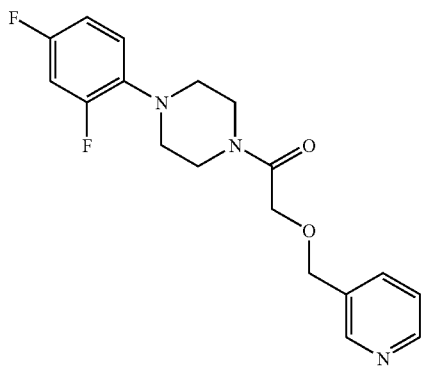 | 1-[4-(2,4- Difluoro-phenyl)-piperazin-1-yl]-2-(pyridin-3-ylmethoxy)-ethanone | 61.5 mg, (36%) brown oil |
| NMR | 8.62 (m, 2 H), 7.73 (dt, 1 H), 7.34 (m, 1 H), 6.83 (m, 3 H), 4.67 (s, 2 H), 4.28 (s, 2 H), 3.81 (t, 2 H), 3.66 (t, 2 H), 3.01 (q, 4 H) | | |
| 2.26 | 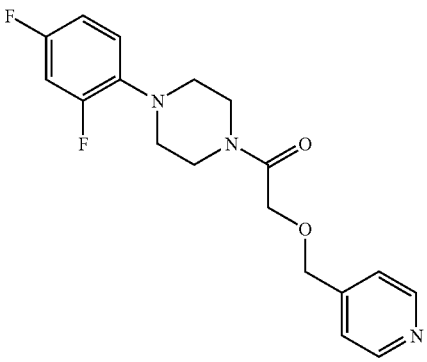 | 1-[4-(2,4-dichloro-phenyl)-piperazin-1-yl]-2-(pyridin-4-ylmethoxy)-ethanone | 23.6 mg, (14%) brown oil |
| NMR | 8.62 (m, 2 H), 7.31 (m, 2 H), 6.83 (m, 3 H), 4.67 (s, 2 H), 4.30 (s, 2 H), 3.81 (t, 2 H), 3.67 (t, 2 H), 3.02 (br, 4 H) | | |
| 2.27 | 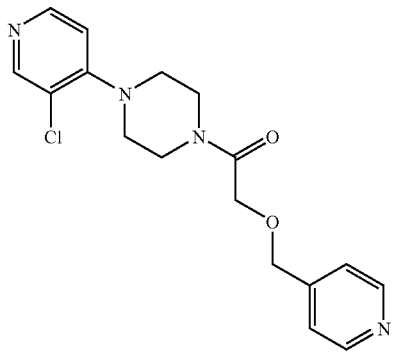 | 1-[4-(3-Chloro-pyridin-4-yl)-piperazin-1-yl]-2-(pyridin-4-ylmethoxy)-ethanone | 13.3 mg (26%) brown oil |
| NMR | 8.62 (bs, 2 H), 8.46 (bs, 1 H), 8.35 (m, 1 H), 7.29 (m, 2 H), 6.81 (d, 1 H), 4.66 (s, 2 H), 4.30 (s, 2 H), 3.83 (t, 2 H), 3.70 (t, 2 H), 3.20 (m, 4 H) | | |

| | | | |
|---|---|---|---|
| 2.28 | 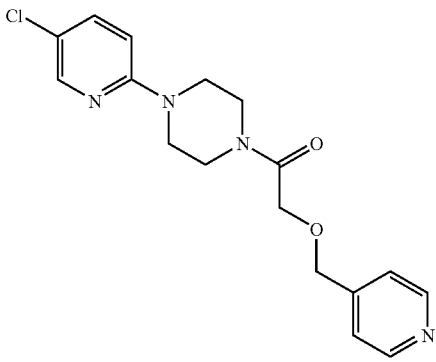 | 1-[4-(5-Chloro-pyridin-2-yl)-piperazin-1-yl]-2-(pyridin-4-ylmethoxy)-ethanone | 38 mg (73%) brown oil |
| NMR | 8.59 (bs, 2 H), 8.11 (dd, 1 H), 7.45 (dd, 1 H), 7.27 (m, 2 H), 6.59 (dd, 1 H), 4.64 (s, 2 H), 4.28 (s, 2 H), 3.74 (m, 2 H), 3.52 (m, 6 H) | | |
| 2.29 | 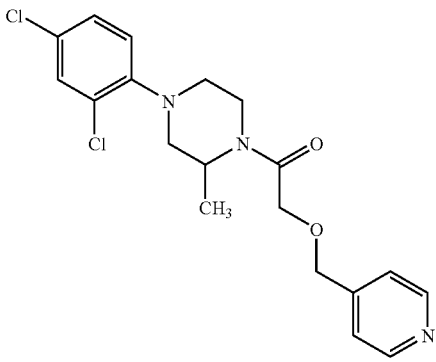 | 1-[4-(2,4-Dichloro-phenyl)-2-methyl-piperazin-1-yl]-2-(pyridin-4-ylmethoxy)-ethanone | 61.4 mg (82%) pale brown oil |
| NMR | 8.61 (m, 2 H), 7.39 (d, 1 H), 7.30 (d, 2 H), 7.21 (dd, 1 H), 6.91 (d, 1 H), 4.86 (m, 1 H), 4.67 (s, 2 H), 4.28 (m, 3 H), 3.66 (m, 1 H), 3.24 (m, 2 H), 2.75 (m, 2 H), 1.49 (bd, 3 H) | | |
| 2.30 | 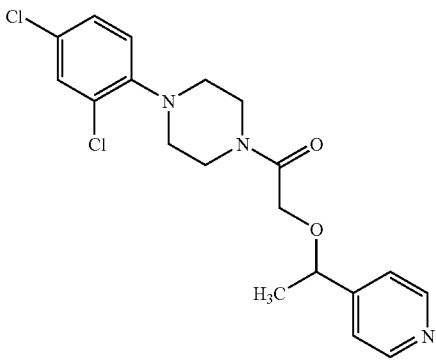 | 1-[4-(2,4-Dichloro-phenyl)-piperazin-1-yl]-2-(1-pyridin-4-yl-ethoxy)-ethanone | 100.6 mg (73%) yellow oil |
| NMR | 8.57 (dd, 2 H), 7.34 (d, 1 H), 7.24 (d, 2 H), 7.17 (dd, 1 H), 6.87 (d, 1 H), 4.54 (q, 1 H), 4.15 (d, 1 H), 4.00 (d, 1 H), 3.73 (m, 2 H), 3.58 (m, 2 H), 2.94 (m, 4 H), 1.47 (d, 3 H) | | |

| | | | | |
|---|---|---|---|---|
| 2.31 | 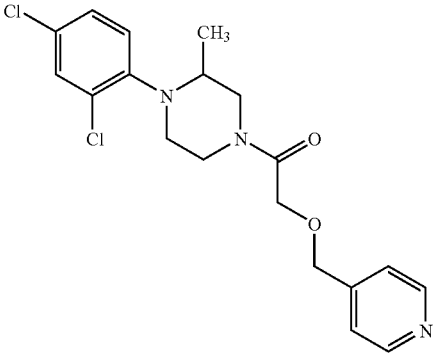 | | 1-[4-(2,4-Dichloro-phenyl)-3-methyl-piperazin-1-yl]-2-(pyridin-4-ylmethoxy)-ethanone | 112.3 mg (89%) yellow oil |
| NMR | 8.56 (bs, 2 H), 7.25 (dd, 2 H), 6.69 (s, 1 H), 6.65 (d, 2 H), 4.61 (s, 2 H), 4.33 (m, 3 H), 3.87 (m, 2 H), 3.57 (m, 1 H), 3.12 (m, 3 H), 1.00 (d, 3 H) | | | |
| 2.32 | 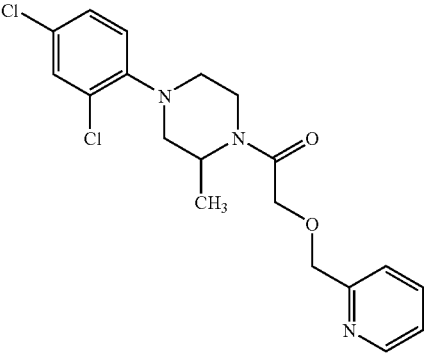 | | 1-[4-(2,4-Dichloro-phenyl)-2-methyl-piperazin-1-yl]-2-(pyridin-2-ylmethoxy)-ethanone | 78 mg (71%) yellow oil |
| NMR | 8.58 (d, 1 H), 7.71 (m, 1 H), 7.50 (d, 1 H), 7.39 (d, 1 H), 7.21 (m, 2 H), 6.92 (d, 1 H), 4.86 (bs, 1 H), 4.75 (s, 2 H), 4.52 (m, 1 H), 4.33 (m, 2 H), 3.78 (m, 0.5 H), 3.62 (m, 0.5 H), 3.22 (t, 2 H), 2.73 (m, 2 H), 1.48 (bd, 3 H) | | | |
| 2.33 | 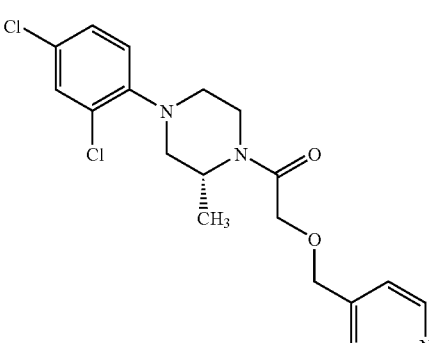 | | 1-[(R)-4-(2,4-Dichloro-phenyl)-2-methyl-piperazin-1-yl]-2-(pyridin-4-ylmethoxy)-ethanone | 90.1 mg (82%) yellow oil |
| NMR | 8.58 (d, 2 H), 7.71 (d, 1 H), 7.50 (d, 2 H), 7.39 (dd, 1 H), 7.21 (d, 1 H), 6.92 (bs, 1 H), 4.86 (s, 2 H), 4.75 (m, 0.5 H), 4.52 (m, 2 H), 4.33 (m, 0.5 H), 3.78 (m, 1 H), 3.62 (m, 2 H), 3.22 (m, 2 H), 2.73 (bd, 3 H) | | | |

| | | | | |
|---|---|---|---|---|
| 2.34 | 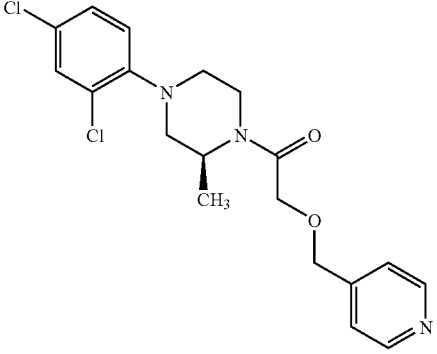 | | 1-[(S)-4-(2,4-Dichloro-phenyl)-2-methyl-piperazin-1-yl]-2-(pyridin-4-ylmethoxy)-ethanone | 90.6 mg (82%) yellow oil |
| NMR | 8.61 (dd, 2 H), 7.40 (d, 1 H), 7.30 (d, 2 H), 7.21 (dd, 1 H), 6.91 (d, 1 H), 4.85 (bs, 0.5 H), 4.67 (s, 2 H), 4.51 (m, 0.5 H), 4.28 (m, 2 H), 4.14 (m, 0.5 H), 3.66 (m, 1 H), 3.24 (m, 2 H), 2.73 (m, 2 H), 1.49 (bd, 3 H) | | | |
| 2.35 | 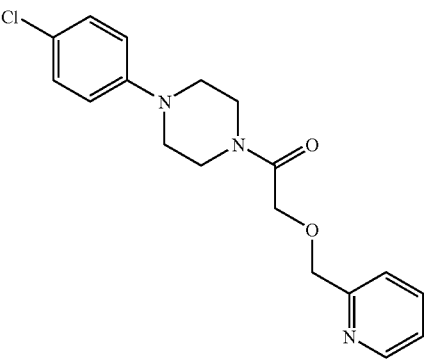 | | 1-[4-(4-Chloro-phenyl)-piperazin-1-yl]-2-(pyridin-2-ylmethoxy)-ethanone | 52.1 mg (54%) yellow solid |
| NMR | 8.59 (dd, 1 H), 7.72 (tt, 1 H), 7.47 (d, 1 H), 7.23 (m, 3 H), 6.84 (dd, 2 H), 4.74 (s, 2 H), 4.34 (s, 2 H), 3.79 (m, 2 H), 3.69 (m, 2 H), 3.14 (m, 4 H) | | | |
| 2.36 | 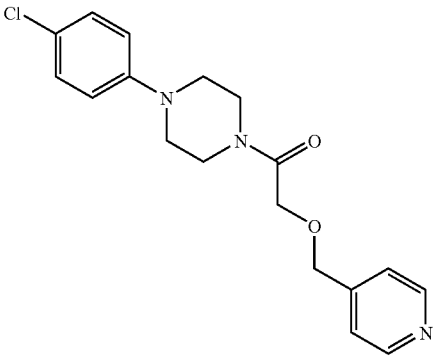 | | 1-[4-(4-Chloro-phenyl)-piperazin-1-yl]-2-(pyridin-4-ylmethoxy)-ethanone | 72.3 mg (75%) off-white solid |
| NMR | 8.61 (dd, 2 H), 7.25 (m, 4 H), 6.84 (dd, 2 H), 4.66 (s, 2 H), 4.29 (s, 2 H), 3.79 (t, 2 H), 3.66 (t, 2 H), 3.14 (m, 4 H) | | | |
| 2.37 | 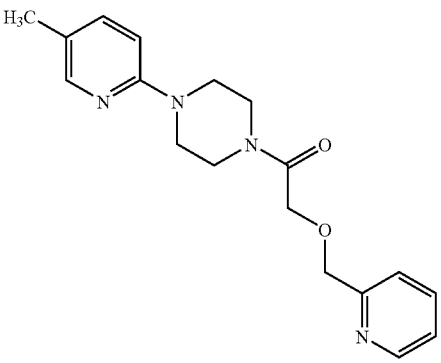 | | 1-[4-(5-Methyl-pyridin-2-yl)-piperazin-1-yl]-2-(pyridin-2-ylmethoxy)-ethanone | 30.6 mg (35%) brown solid |

| | | | |
|---|---|---|---|
| NMR | 8.58 (d, 1 H), 8.04 (d, 1 H), 7.69 (tt, 1 H), 7.48 (d, 1 H), 7.35 (dd, 1 H), 7.24 (m, 1 H), 6.61 (d, 1 H), 4.75 (s, 2 H), 4.35 (s, 2 H), 3.76 (m, 2 H), 3.65 (m, 2 H), 3.52 (m, 4 H), 2.22 (s, 3 H) | | |
| 2.38 | 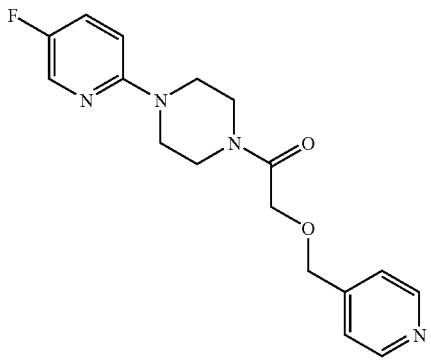 | 1-[4-(5-Fluoro-pyridin-2-yl)-piperazin-1-yl]-2-(pyridin-4-ylmethoxy)-ethanone | 71.5 mg (46%) brown oil |
| NMR | 8.60 (d, 2 H), 8.11 (d, 1 H), 7.45 (dd, 1 H), 7.29 (d, 2 H), 6.58 (d, 1 H), 4.83 (m, 0.5 H), 4.66 (s, 2 H), 4.47 (m, 0.5 H), 4.26 (bs, 2 H), 4.12 (m, 2 H), 3.86 (m, 1 H), 3.46 (m, 1 H), 3.15 (m, 1 H), 2.93 (t, 1 H), 1.27 (m, 3 H) | | |
| 2.39 | 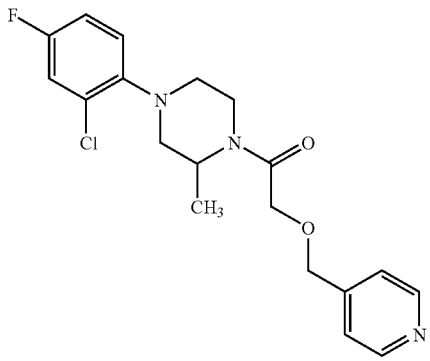 | 1-[4-(2-Chloro-4-fluoro-phenyl)-2-methyl-piperazin-1-yl]-2-(pyridin-4-ylmethoxy)-ethanone | 3.1 mg (4%) yellow oil |
| NMR | 8.60 (m, 2 H), 7.29 (m, 2 H), 7.15 (dd, 1 H), 6.95 (d, 2 H), 4.84 (m, 0.5), 4.67 (s, 2 H), 4.50 (m, 0.5), 4.28 (m, 2 H), 4.10 (m, 1 H), 3.65 (m, 1 H), 3.18 (m, 2 H), 2.74 (m, 2 H), 1.48 (m, 3 H) | | |

The starting materials (piperazines or benzyloxyacetic acids) for compounds 2.15 to 2.28 are prepared as follows (Example 3.1 to Example 3.32):

EXAMPLE 3.1

4-(4-Chloro-2-fluoro-phenyl)-piperazine-1-carboxylic acid tert-butylester

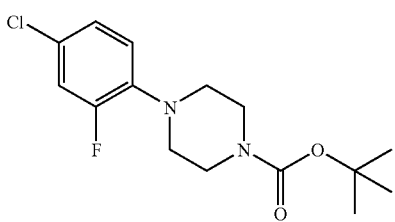

General Procedure: In a 20 mL tube equipped with a stir bar added 1-bromo-4-chloro-2-fluorobenzene (1 g, 4.77 mmol), $^t$butyl-1-piperazinecarboxylate (1.74 g, 9.55 mmol), palladium acetate (0.107 g, 0.48 mmol), 2-di$^t$butylphosphenylbiphenyl (0.143 g, 0.48 mmol), sodium tert-butoxide (0.688 g, 7.16 mmol) and toluene (10 mL). The reaction vessel was sealed and placed in a microwave oven at 150° C. for 15 min. The reaction mixture was filtered though Diatomaceous earth. The filtrate was diluted with ethyl acetate (50 mL), sequentially washed with water (3×50 mL) and brine (50 mL) in a separation funnel. The organic layer was dried over anhydrous sodium sulfate, filtered and concentrated in vacuo. The crude residue was purified on silica gel using hexanes: ethyl acetate=93:7 to hexanes:ethyl acetate=95:5 in a gradient fashion, to isolate the desired product as yellow oil (639 mg, 43%). $^1$H NMR (300 MHz, CDCl$_3$): δ 7.03 (m, 2H), 6.83 (m, 1H), 3.57 (t, 4H), 2.95 (t, 4H), 1.46 (s, 9H).

In a similar fashion the following compound was synthesized:

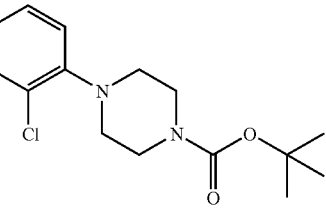

| | | | |
|---|---|---|---|
| 3.2 | (structure) | 4-(2-Chloro-4-fluoro-phenyl)-piperazine-1-carboxylic acid tert-butylester | 473 mg (32%) yellow oil |
| NMR | 7.07 (dd, 1 H), 6.89 (m, 2 H), 3.54 (t, 4 H), 2.86 (t, 4 H), 1.44 (s, 9 H) | | |

EXAMPLE 3.3

4-(2,4-Dichloro-phenyl)-2-methyl-piperazine-1-carboxylic acid tert-butyl ester

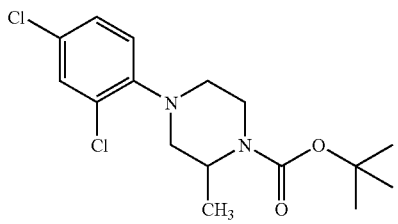

General Procedure: To a 50 mL screw-cap round bottom flask equipped with a stir bar were added 1-bromo-2,4-dichlorobenzene (2.0 g, 8.85 mmol), 2-methyl-piperazine-1-carboxylic acid tert-butyl ester (2.13 g, 10.6 mmol), palladium acetate (0.199 g, 0.89 mmol), 2-di-tert-butylphosphenylbiphenyl (0.264 g, 0.48 mmol), sodium tert-butoxide (1.02 g, 10.6 mmol) and toluene (20 mL). The reaction flask was sealed and the reaction mixture was heated at 110° C. overnight. The reaction mixture was filtered through diatomaceous earth and the filtrate was concentrated in vacuo. The residue was dissolved in ethyl acetate and washed with water (2×50 mL) and brine (50 mL). The organic layer was dried over anhydrous sodium sulfate, filtered and concentrated in vacuo. The crude residue was purified on silica gel using hexanes:diethyl ether=95:5 to 90:10 in a gradient fashion, to give the desired product as yellow oil (858 mg, 28%). $^1$H NMR (300 MHz, CDCl$_3$): δ 7.28 (d, 1H), 7.11 (dd, 1H), 6.85 (d, 1H), 4.28 (bs, 1H), 3.89 (d, 1H), 3.22 (m, 1H), 3.08 (m, 2H), 2.67 (m, 2H), 1.43 (s, 9H), 1.34 (d, 3H).

In a similar fashion the following compounds were synthesized:

| | | | |
|---|---|---|---|
| 3.4 | (structure) | (R)-4-(2,4-Dichloro-phenyl)-2-methyl-piperazine-1-carboxylic acid tert-butyl ester | 131 mg (18%) yellow oil |
| NMR | 7.36 (d, 1 H), 7.17 (dd, 1 H), 6.91 (d, 1 H), 4.32 (m, 1 H), 3.95 (bd, 1 H), 3.28 (m, 1 H), 3.15 (m, 2 H), 2.75 (m, 2 H), 1.48 (s, 9 H), 1.38 (d, 3 H) | | |
| 3.5 | (structure) | (S)-4-(2,4-Dichloro-phenyl)-2-methyl-piperazine-1-carboxylic acid tert-butyl ester | 138 mg (19%) yellow oil |
| NMR | 7.36 (d, 1 H), 7.17 (dd, 1 H), 6.91 (d, 1 H), 4.32 (m, 1 H), 3.95 (bd, 1 H), 3.28 (m, 1 H), 3.15 (m, 2 H), 2.75 (m, 2 H), 1.48 (s, 9 H), 1.38 (d, 3 H | | |

EXAMPLE 3.6

4-(3-Chloro-pyridin-4-yl)-piperazine-1-carboxylic acid tert-butyl ester

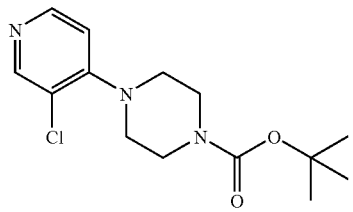

General Procedure: To a 50 mL round bottom flask equipped with a stir bar were added 3,4-dichloropyridine (0.70 g, 4.73 mmol), piperazine-1-carboxylic acid tert-butyl ester (0.86 g, 4.73 mmol), copper powder (36 mg, 0.57 mmol), potassium carbonate (0.65 g, 4.73 mmol) and N,N-dimethylformamide (10 mL). The reaction mixture was stirred at 110° C. overnight. The reaction mixture was cooled to room temperature, diluted with ethyl acetate (100 mL) and sequentially washed with water (50 mL), saturated aqueous sodium bicarbonate (50 mL), water (50 mL) and brine (50 mL). The organic layer was dried over anhydrous sodium sulfate, filtered and concentrated in vacuo. The crude residue was purified on silica gel using hexanes:ethyl acetate=80:20 to 50:50 in a gradient fashion, to give the desired product as a yellow solid (404 mg, 29%). $^1$H NMR (300 MHz, CDCl$_3$): δ 8.30 (bd, 2H), 6.74 (d, 1H), 3.52 (m, 4H), 3.07 (m, 4H), 1.4 (s, 9H).

In a similar fashion the following compounds were synthesized:

EXAMPLE 3.9

4-(2,4-Dichloro-phenyl)-3-methyl-piperazine-1-carboxylic acid tert-butyl ester

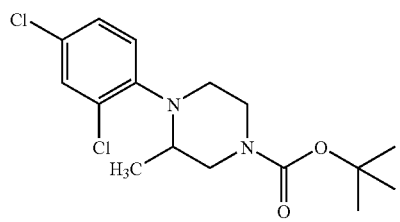

General Procedure: To a 75 mL screw-cap round bottom flask equipped with a stir bar were added 1-bromo-2,4-dichlorobenzene (0.72 mL, 5.99 mmol), 3-methyl-piperazine-1-carboxylic acid tert-butyl ester (1.0 g, 4.99 mmol), 2-di-tert-butylphosphino-2'-(N,N-dimethylamine)biphenyl (51.1 mg, 0.15 mmol), tris(dibenzylideneacetone)dipalladium (45.7 mg, 0.05 mmol) and tetrahydrofuran (30 mL). The reaction flask was flushed with nitrogen for 5 minutes and then lithium bis(trimethylsilyl)amide (1 M in tetrahydrofuran, 6.99 mL, 6.99 mmol) was added in one portion. The reaction flask was sealed and the reaction mixture was stirred at room temperature for 72 hours. The reaction mixture was concentrated in vacuo and the residue purified on silica gel using hexanes:acetone=98:2 to give the desired product as an off-white solid (130 mg, 8%). $^1$H NMR (300 MHz, CDCl$_3$):

| 3.7 | 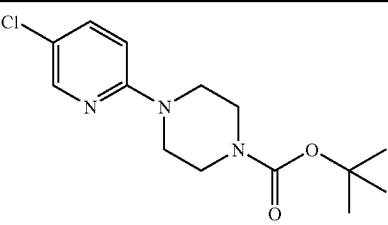 | 4-(5-Chloro-pyridin-2-yl)-piperazine-1-carboxylic acid tert-butyl ester | 675 mg (44%) white solid |
|---|---|---|---|
| NMR | 8.12 (d, 1 H), 7.44 (dd, 1 H), 6.59 (d, 1 H), 3.51 (m, 8 H), 1.49 (s, 9 H) | | |
| 3.8 | 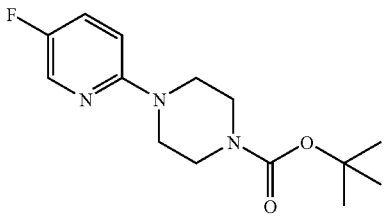 | 4-(5-Fluoro-pyridin-2-yl)-piperazine-1-carboxylic acid tert-butyl ester | 169 mg (11%) clear oil |
| NMR | 8.07 (d, 1 H), 7.28 (m, 1 H), 6.62 (dd, 1 H), 3.56 (m, 4 H), 3.46 (m, 4 H), 1.49 (s, 9 H) | | |

δ 6.77 (t, 1H), 6.68 (d, 2H), 4.10 (bs, 1H), 3.85 (bs, 2H), 3.12 (m, 4H), 1.48 (s, 9H), 1.04 (d, 3H).

EXAMPLE 3.10

4-(2-Chloro-4-fluoro-phenyl)-2-methyl-piperazine-1-carboxylic acid tert-butyl ester

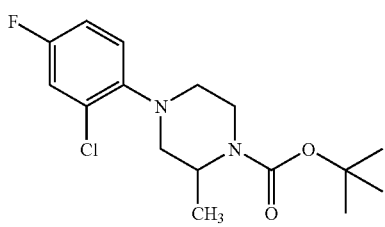

General Procedure: To a round bottom flask equipped with a stir bar were added 1-bromo-2-chloro-4-fluorobenzene (0.314 g, 1.5 mmol), 2-methyl-piperazine-1-carboxylic acid tert-butyl ester (0.451 g, 2.25 mmol), sodium tert-butoxide (0.216 g, 2.25 mmol) and toluene (15 mL). The reaction mixture was heated to 80° C. and then a mixture of tris(dibenzylidine acetone)dipalladium (31.1 mg, 0.015 mmol) and racemic 2,2'-bis(diphenylphosphino)-1,1'-binaphthyl (13.7 mg, 0.05 mmol) in toluene (2 mL) was slowly added to the reaction mixture. The reaction mixture was stirred at 110° C. overnight and then concentrated in vacuo. The residue was dissolved in ethyl acetate (100 mL) and washed with water (3×50 mL) and brine (50 mL). The organic layer was dried over anhydrous sodium sulfate, filtered and concentrated in vacuo. The crude residue was purified on silica gel using hexanes:diethyl ether=100:0 to 80:20 in a gradient fashion, to give the desired product (147.9 mg, 28%). $^1$H NMR (300 MHz, CDCl$_3$): δ 7.15 (m, 1H), 6.96 (m, 2H), 4.33 (m, 1H), 3.95 (d, 1H), 3.29 (m, 1H), 3.13 (m, 2H), 2.74 (m, 2H), 1.49 (s, 9H), 1.40 (d, 3H).

EXAMPLE 3.11

1-(2-Chloro-4-fluoro-phenyl)-3-methyl-piperazine

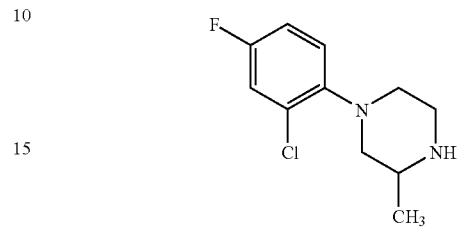

General Procedure: In a 50 mL round bottom flask equipped with a stir bar were added 4-(2-chloro-4-fluoro-phenyl)-2-methyl-piperazine-1-carboxylic acid tert-butyl ester (147.9 mg, 0.45 mmol) and dichloromethane (1.5 mL). The solution was cooled to 0° C. and to it was added trifluoroacetic acid (1.5 mL). The reaction mixture was stirred at 0° C. for 10 minutes and then at room temperature overnight. The reaction mixture was concentrated in vacuo and the residue was dissolved in dichloromethane and treated with 2 N hydrochloric acid in diethyl ether (3.5 mL). The resulting suspension was stirred at room temperature overnight and then was concentrated in vacuo. The residue was triturated with diethyl ether and filtered to give the desired product as a pale brown solid (66.3 mg, 49%). $^1$H NMR (300 MHz, CDCl$_3$): δ 9.29 (bs, 1H), 8.97 (bs, 1H), 7.46 (d, 1H), 7.24 (m, 2H), 3.37 (m, 2H), 3.29 (m, 2H), 3.15 (m, 1H), 2.95 (m, 1H), 2.80 (m, 1H), 1.15 (d, 3H).

In a similar fashion the following compounds were synthesized as free bases or hydrochloride salts:

| | Structure | Name | Yield |
|---|---|---|---|
| 3.12 | ![structure] | 1-(2-Chloro-4-fluoro-phenyl)-piperazine | 262 mg (81%) yellow oil |
| NMR | 7.16 (dd, 1 H), 6.99 (m, 2 H), 3.04 (m, 8 H) | | |
| 3.13 | ![structure] | 1-(3-Chloro-pyridin-4-yl)-piperazine | 169 mg (41%) mustard solid |
| NMR | 8.71 (bs, 1 H), 8.47 (m, 1 H), 7.52 (d, 1 H), 3.96 (m, 4 H), 3.49 (m, 4 H) | | |
| 3.14 | ![structure] | 1-(5-Chloro-pyridin-2-yl)-piperazine | 572 mg (82%) off-white solid |
| NMR | 8.18 (d, 1 H), 8.02 (dd, 1 H), 7.38 (d, 1 H), 3.99 (m, 4 H), 3.45 (m, 4 H) | | |

-continued

| 3.15 | 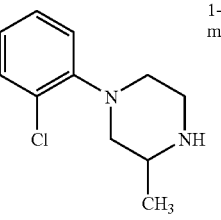 | 1-(2,4-Dichloro-phenyl)-3-methyl-piperazine | 495 mg (81%) brown oil |
| NMR | 7.37 (d, 1 H), 7.20 (dd, 1 H), 6.97 (d, 1 H), 3.24 (m, 2 H), 3.10 (m, 3 H), 2.69 (m, 1 H), 2.36 (m, 1 H), 1.12 (d, 3 H) | | |
| 3.16 | 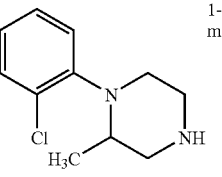 | 1-(2,4-Dichloro-phenyl)-2-methyl-piperazine | 85 mg (91%) |
| NMR | 6.74 (m, 1 H), 6.69 (d, 2 H), 3.82 (m, 1 H), 3.02 (m, 6 H), 1.10 (d, 3 H) | | |
| 3.17 | 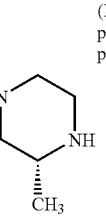 | (R)-1-(2,4-Dichloro-phenyl)-3-methyl-piperazine | 73.1 mg (79%) yellow oil |
| NMR | 7.37 (d, 1 H), 7.20 (dd, 1 H), 6.97 (d, 1 H), 3.24 (m, 2 H), 3.10 (m, 3 H), 2.70 (m, 1 H), 2.35 (m, 1 H), 1.11 (d, 3 H) | | |
| 3.18 | 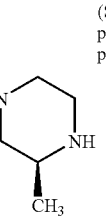 | (S)-1-(2,4-Dichloro-phenyl)-3-methyl-piperazine | 79 mg (81%) yellow oil |
| NMR | 7.37 (d, 1 H), 7.20 (dd, 1 H), 6.97 (d, 1 H), 3.23 (m, 2 H), 3.10 (m, 3 H), 2.68 (m, 1 H), 2.35 (m, 1 H), 1.11 (d, 3 H) | | |
| 3.19 | 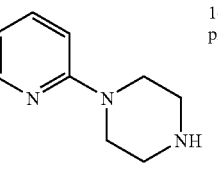 | 1-(5-Fluoro-pyridin-2-yl)-piperazine | 95.1 mg (87%) yellow oil |
| NMR | 7.99 (d, 1 H), 7.19 (m, 1 H), 6.54 (dd, 1 H), 3.36 (m, 4 H), 2.90 (m, 4 H) | | |
| 3.20 | 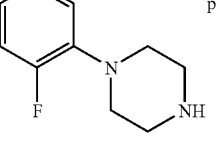 | 1-(4-Chloro-2-fluoro-phenyl)-piperazine | 368.6 mg (85%) yellow oil |
| NMR | 7.07 (m, 2 H), 6.85 (t, 1 H), 3.04 (m, 8 H) | | |

EXAMPLE 3.21

2-(4-Fluoro-benzyloxy)-propionic acid ethyl ester

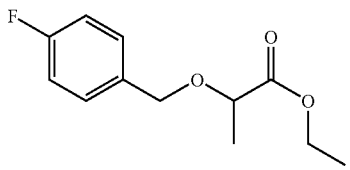

In a screw-cap vial was added sodium hydride (60% in mineral oil, 175 mg, 4.36 mmol) and tetrahydrofuran (1 mL). The suspension was cooled to 0° C. A solution of ethyl lactate (0.46 mL, 3.97 mmol) in tetrahydrofuran (3.0 mL) was added to the above suspension and the resulting reaction mixture was stirred at room temperature for 15 min. To this mixture added 4-fluoro-benzyl bromide (0.75 g, 3.97 mmol) solution in tetrahydrofuran (4 mL) followed by tetrabutyl ammonium iodide (10 mg). The reaction mixture was stirred at room temperature overnight. The reaction mixture was diluted with water (10 mL) and extracted with ethyl acetate (3×20 mL). The combined organic layers were dried over anhydrous sodium sulfate, filtered and concentrated in vacuo. The crude residue was purified on silica gel using hexanes:ethyl acetate=98:2 to hexanes:ethyl acetate=92:8 in a gradient fashion, to isolate the desired product as clear oil (0.380 g, 42%). $^1$H NMR (300 MHz, CDCl$_3$): δ 7.31 (m, 2H), 6.97 (m, 2H), 4.59 (d, 1H), 4.37 (d, 1H), 4.16 (q, 2H), 4.01 (q, 1H), 1.39 (d, 3H), 1.25 (t, 3H)

EXAMPLE 3.22

2-(4-Fluoro-benzyloxy)-propionic acid

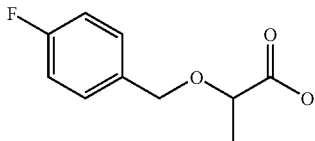

To a round bottom flask equipped with stir bar was added 2-(4-fluoro-benzyloxy)-propionic acid ethyl ester (0.380 g, 1.68 mmol), dioxane (6 mL) and 1N aqueous sodium hydroxide (1.76 mL, 1.76 mmol). The resulting mixture was stirred at room temperature overnight. The reaction mixture was concentrated in vacuo. The isolated residue was treated with 2N aqueous hydrochloric acid (10 mL) then extracted with dichloromethane (4×20 mL). The combined organic phase was dried over anhydrous sodium sulfate, filtered and concentrated in vacuo to isolate desired product as clear oil (328 mg, 99%). Isolated material was used as such in the next step.
$^1$ NMR (300 MHz, CDCl$_3$): δ 11.5 (br, 1H), 7.35 (m, 2H), 7.03 (m, 2H), 4.65 (d, 1H), 4.48 (d, 1H), 4.10 (q, 1H), 1.50 (d, 3H)

EXAMPLE 3.23

(3-Methyl-3H-imidazol-4-ylmethoxy)-acetic acid tert-butyl ester

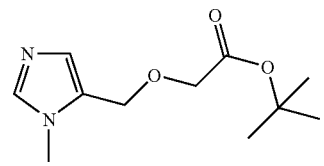

General Procedure: In a 50 mL round bottom flask was added sodium hydride (60% in mineral oil, 480 mg, 12.0 mmol) and N,N-dimethylformamide (5 mL). The suspension was cooled to 0° C. A solution of (3-methyl-3H-imidazol-4-yl)-methanol (1.12 g, 10.0 mmol) in N,N-dimethylformamide (10 mL) was added to the above suspension and the resulting reaction mixture was stirred at room temperature for 20 min. To this mixture was added tert-butylbromoacetate (1.6 mL, 11.0 mmol) solution in N,N-dimethylformamide (5 mL), followed by tetrabutyl ammonium iodide (10 mg). The reaction mixture was stirred at room temperature overnight. The reaction mixture was diluted with water (10 mL) and extracted with ethyl acetate (3×50 mL). The combined organic layers were washed with brine (50 mL), dried over anhydrous sodium sulfate, filtered and concentrated in vacuo. The crude residue was purified on silica gel using chloroform: 2% ammonia-methanol=99:1 to chloroform:2% ammonia-methanol=96:4 in a gradient fashion, to isolate the desired intermediate as yellow oil. $^1$H NMR (300 MHz, CDCl$_3$): δ 7.39 (s, 1H), 6.95 (s, 1H), 4.52 (s, 2H), 3.86 (s, 2H), 3.66 (s, 2H), 1.41 (s, 9H)

In a similar fashion the following compounds were synthesized:

| 3.24 | | (Pyridin-2-ylmethoxy)-acetic acid tert-butyl ester | 700 mg (31%) yellow oil |
|---|---|---|---|
| | NMR | 8.30 (dd, 1 H), 7.44 (dt, 1 H), 7.28 (d, 1 H), 6.95 (dt, 1 H), 4.52 (s, 2 H), 3.89 (s, 2 H), 1.25 (s, 9 H) | |

| | | | |
|---|---|---|---|
| 3.25 | 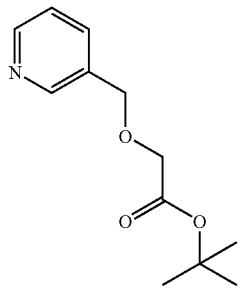 | (Pyridin-3-ylmethoxy)-acetic acid tert-butyl ester | 815 mg (36%) yellow oil |
| NMR | | | |
| 3.26 | 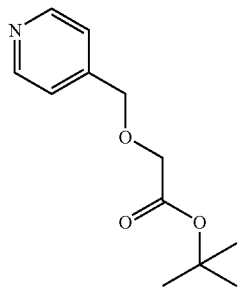 | (Pyridin-4-ylmethoxy)-acetic acid tert-butyl ester | 790 mg (35%) yellow oil |
| NMR | 8.59 (dd, 2 H), 7.30 (dd, 2 H), 4.64 (s, 2 H), 4.04 (s, 2 H), 1.49 (s, 9 H) | | |

EXAMPLE 3.27

(3-Methyl-3H-imidazol-4-ylmethoxy)-acetic acid

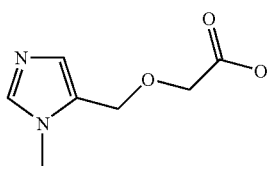

General Procedure: In a 50 mL round bottom flask equipped with a stir bar was added (3-methyl-3H-imidazol-4-ylmethoxy)-acetic acid tert-butyl ester, trifluoroacetic acid (3 mL) and dichloromethane (3 mL) at 0° C. The reaction mixture was left stirring at room temperature for 2.5 h then concentrated in vacuo. The residue was diluted with ethyl acetate (10 mL) and treated with 4N aqueous hydrochloric acid (3 mL). The resulting mixture was concentrated in vacuo and the isolated residue was triturated with ether to give desired product as hydrochloride salt, off-white solid (140 mg). $^1$H NMR (300 MHz, CDCl$_3$): δ 14.6 (br, 1H), 12.9 (br, 1H), 9.14 (s, 1H), 7.74 (s, 1H), 4.66 (s, 2H), 4.11 (s, 2H), 3.87 (s, 3H)

In a similar fashion the following compounds were synthesized as hydrochloride or formate salts:

| | | | |
|---|---|---|---|
| 3.28 | 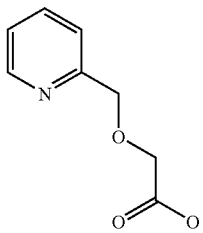 | (Pyridin-2-ylmethoxy)-acetic acid | 709 mg yellow solid |
| NMR | 8.82 (d, 1 H), 8.50 (m, 1 H), 7.95 (m, 2 H), 5.06 (s, 2 H), 4.35 (d, 2 H) | | |

| | | | |
|---|---|---|---|
| 3.29 | (pyridin-3-ylmethyl structure) | (Pyridin-3-ylmethoxy)-acetic acid | 812 mg yellow oil |
| NMR | 8.87 (d, 2 H), 8.54 (m, 1 H), 8.05 (dd, 1 H), 4.72 (s, 2 H), 4.30 (d, 2 H) | | |
| 3.30 | (pyridin-4-ylmethyl structure) | (Pyridin-4-ylmethoxy)-acetic acid | 772 mg yellow solid |
| NMR | 8.88 (d, 2 H), 7.97 (m, 2 H), 4.89 (s, 2 H), 4.30 (d, 2 H) | | |
| 3.31 | (1-pyridin-4-yl-ethoxy structure) | (1-Pyridin-4-yl-ethoxy)-acetic acid | 570 mg (83%) grey-yellow solid |
| NMR | 8.82 (bd, 2 H), 8.12 (bd, 2 H), 4.97 (m, 1 H), 4.19 (d, 2 H), 1.55 (d, 3 H) | | |

EXAMPLE 3.32

(1-Pyridin-4-yl-ethoxy)-acetic acid tert-butyl ester

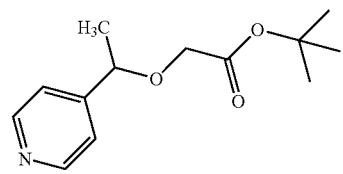

General Procedure: To a 250 mL round bottom flask equipped with a stir bar and a dropping funnel were added sodium hydride (60% in mineral oil, 0.65 g, 16.2 mmol) and N,N-dimethylformamide (10 mL). The suspension was cooled to 0° C. and a solution of 1-pyridin-4-yl-ethanol (2.0 g, 16.2 mmol) in N,N-dimethylformamide (20 mL) was added dropwise. The reaction mixture was stirred at room temperature for 20 minutes and then cooled to 0° C. A solution of tert-butylbromoacetate (3.12 mL, 21.1 mmol) in N,N-dimethylformamide (10 mL) was then added dropwise. The reaction mixture was stirred at room temperature overnight. The reaction mixture was cooled to room temperature, diluted with ethyl acetate, washed with water and washed with brine. The organic layer was dried over anhydrous sodium sulfate, filtered and concentrated in vacuo. The residue was purified on silica gel using hexanes:acetone=95:5 to 85:15 in a gradient fashion, to give the desired product as brown oil (746 mg, 19%). $^1$H NMR (300 MHz, CDCl$_3$): δ 8.59 (dd, 2H), 7.27 (dd, 2H), 4.56 (q, 1H), 3.95 (d, 1H), 3.80 (d, 1H), 1.50 (d, 3H), 1.46 (s, 9H).

EXAMPLE 4.1

1-[4-(2,4-Dichloro-phenyl)-piperazin-1-yl]-2-(3-fluoro-benzyloxy)-ethanone

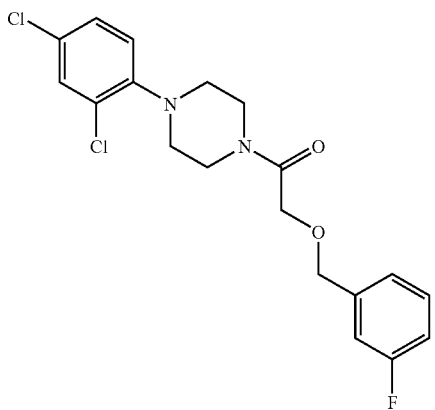

General Procedure: To a screw-cap vial was added sodium hydride (60% in mineral oil, 13 mg, 0.325 mmol) and tetrahydrofuran (1 mL). The suspension was cooled to 0° C. A solution of 1-[4-(2,4-Dichloro-phenyl)-piperazin-1-yl]-2-hydroxy-ethanone (85.5 mg, 0.295 mmol) in tetrahydrofuran (1.5 mL) was added to the above suspension and the resulting purple reaction mixture was stirred at room temperature for 15 min. To this mixture was added 3-fluoro-benzyl bromide (55.9 mg, 0.29 mmol) solution in tetrahydrofuran (2 mL) followed by tetrabutyl ammonium iodide (5 mg). The reaction was stirred at room temperature overnight. The reaction mixture was diluted with water (8 mL) and extracted with ethyl acetate (3×8 mL). The combined organic layers were dried over anhydrous sodium sulfate, filtered and concentrated in vacuo. The crude residue was purified on silica gel using hexanes:ethyl acetate=96:4 to hexanes:ethyl acetate=70:30 in a gradient fashion, to isolate the desired product as clear oil (69.4 mg, 60%). $^1$H NMR (300 MHz, CDCl$_3$): δ 7.34 (m, 2H), 7.19 (dd, 1H), 7.16 (m, 2H), 7.11 (dt, 1H), 6.90 (d, 1H), 4.62 (s, 2H), 4.24 (s, 2H), 3.80 (t, 2H), 3.66 (t, 2H), 2.98 (q, 4H)

In a similar fashion the following compounds were synthesized:

| | | | | |
|---|---|---|---|---|
| 4.2 | 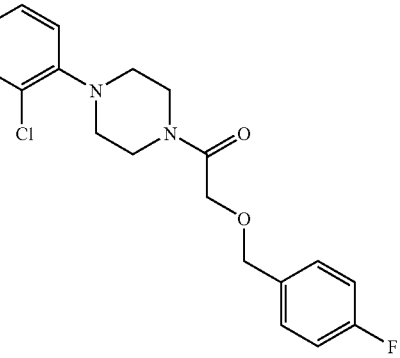 | | 1-[4-(2,4-Dichloro-phenyl)-piperazin-1-yl]-2-(4-fluoro-benzyloxy)-ethanane | 53.7 mg (47%) clear oil |
| NMR | | 7.36 (m, 3 H), 7.19 (dd, 1 H), 7.04 (m, 2 H), 6.90 (d, 1 H), 4.58 (s, 2 H), 4.22 (s, 2 H), 3.79 (t, 2 H), 3.65 (t, 2 H), 2.98 (g, 4 H) | | |
| 4.3 | 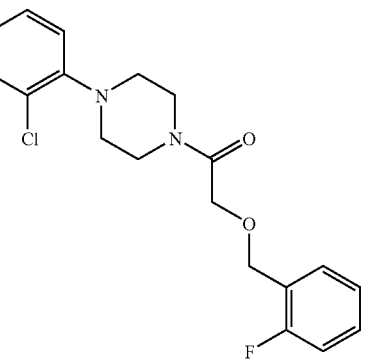 | | 1-[4-(2,4-Dichloro-phenyl)-piperazin-1-yl-2-(2-fluoro-benzyloxy)-ethanone | 52.8 mg (46%) yellow oil |
| NMR | | 7.42 (m, 3 H), 7.17 (m, 3 H), 6.93 (d, 1 H), 4.69 (s, 2 H), 4.27 (s, 2 H), 3.80 (t, 2 H), 3.69 (t, 2 H), 3.00 (q, 4 H) | | |
| 4.4 | 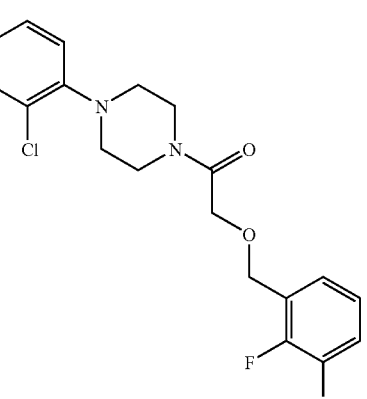 | | 1-[4-(2,4-Dichloro-phenyl)-piperazin-1-yl]-2-(2,3-difluoro-benzyloxy)-ethanone | 61.2 mg (51%) yellow oil |
| NMR | | 7.41 (d, 1 H), 7.21 (m, 4 H), 6.93 (d, 1 H), 4.71 (s, 2 H), 4.28 (s, 2 H), 3.81 (t, 2 H), 3.68 (t, 2 H), 3.01 (q, 4 H) | | |

| | | | |
|---|---|---|---|
| 4.5 |  | 1-[4-(2,4-Dichloro-phenyl)-piperazin-1-yl]-2-(2,4-difluoro-benzyloxy)-ethanone | 78.4 mg (65%) yellow oil |
| NMR | 7.42 (m, 2 H), 7.23 (dd, 1 H), 6.93 (m, 3 H), 4.64 (s, 2 H), 4.26 (s, 2 H), 3.81 (t, 2 H), 3.68 (t, 2 H), 3.01 (q, 4 H) | | |
| 4.6 |  | 1-[4-(2,4-Dichloro-phenyl)-piperazin-1-yl]-2-(2,5-difluoro-benzyloxy)-ethanone | 86.4 mg, (72%) yellow oil |
| NMR | 7.4l (d, 1 H), 7.21 (m, 2 H), 6.96 (m, 3 H), 4.67 (s, 2 H), 4.29 (s, 2 H), 3.82 (t, 2 H), 3.68 (t, 2 H), 3.01 (q, 4 H) | | |
| 4.7 | | 1-[4-(2,4-Dichloro-phenyl)-piperazin-1-yl]-2-(2,6-difluoro-benzyloxy)-ethanone | 61.1 mg (51%) yellow oil |
| NMR | 7.38 (m, 2 H), 7.23 (d, 1 H), 6.93 (m, 3 H), 4.71 (s, 2 H), 4.27 (s, 2 H), 3.80 (t, 2 H), 3.67 (t, 2 H), 3.00 (br, 4 H) | | |

| 4.8 | 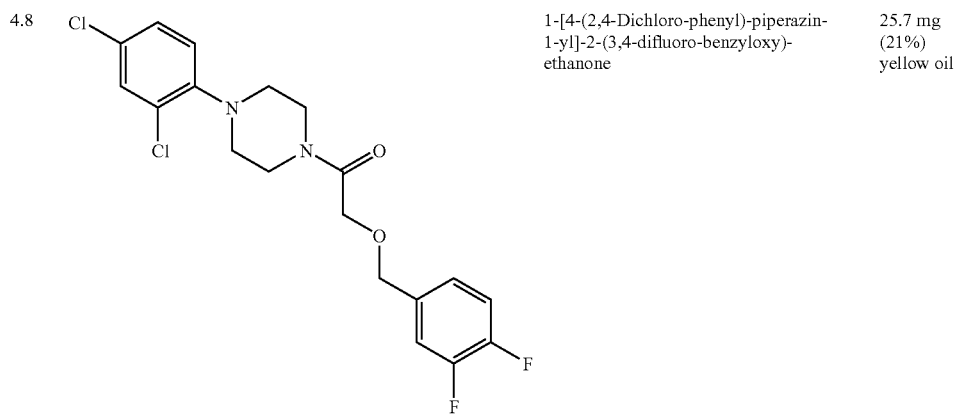 | 1-[4-(2,4-Dichloro-phenyl)-piperazin-1-yl]-2-(3,4-difluoro-benzyloxy)-ethanone | 25.7 mg (21%) yellow oil |
|---|---|---|---|
| NMR | 7.41 (d, 1 H), 7.21 (m, 4 H), 6.93 (d, 1 H), 4.59 (s, 2 H), 4.25 (s, 2 H), 3.81 (t, 2 H), 3.67 (t, 2 H), 3.01 (q, 4 H) | | |
| 4.9 | 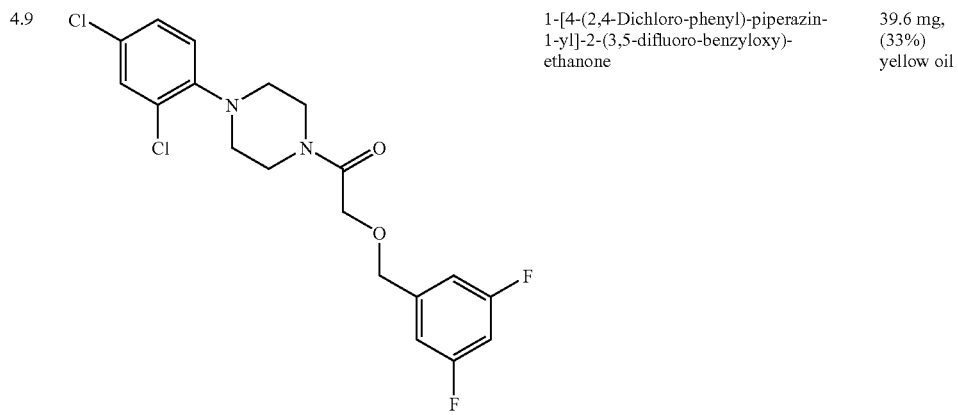 | 1-[4-(2,4-Dichloro-phenyl)-piperazin-1-yl]-2-(3,5-difluoro-benzyloxy)-ethanone | 39.6 mg, (33%) yellow oil |
| NMR | 7.41 (d, 1 H), 7.22 (dd, 1 H), 6.92 (m, 3 H), 6.76 (m, 1 H), 4.62 (s, 2 H), 4.27 (s, 2 H), 3.82 (t, 2 H), 3.67 (t, 2 H), 3.02 (br, 4 H) | | |
| 4.10 | 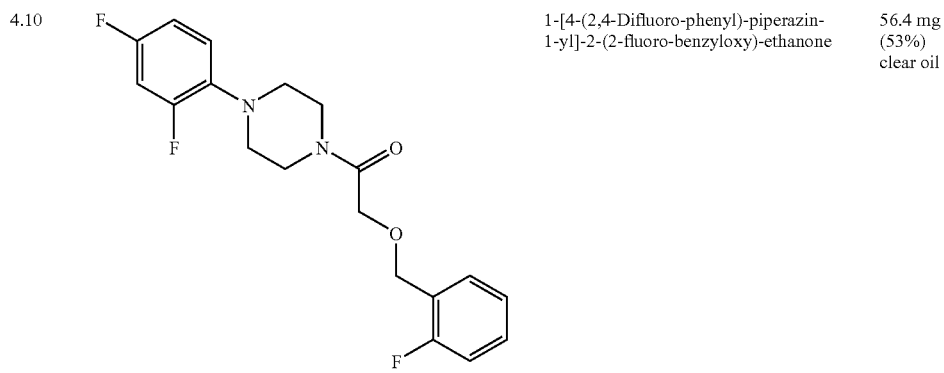 | 1-[4-(2,4-Difluoro-phenyl)-piperazin-1-yl]-2-(2-fluoro-benzyloxy)-ethanone | 56.4 mg (53%) clear oil |
| NMR | 7.44 (dt, 1 H), 7.19 (m, 1 H), 7.08 (m, 2 H), 6.82 (m, 3 H), 4.69 (s, 2 H), 4.27 (s, 2 H), 3.80 (t, 2 H), 3.68 (t, 2 H), 3.02 (br, 4 H) | | |

| | | | |
|---|---|---|---|
| 4.11 | 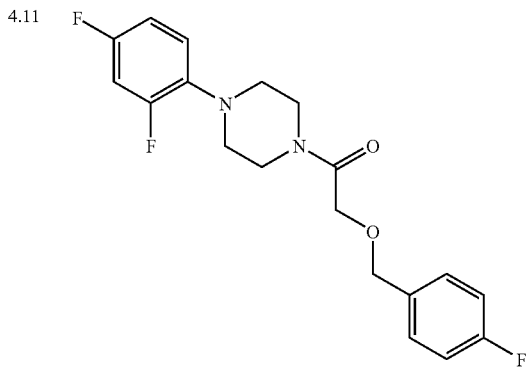 | 1-[4-(2,4-Difluoro-phenyl)-piperazin-1-yl]-2-(4-fluoro-benzyloxy)-ethanone | 43.8 mg (41%) clear oil |
| NMR | 7.36 (m, 2 H), 7.06 (t, 2 H), 6.83 (m, 3 H), 4.59 (s, 2 H), 4.23 (s, 2 H), 3.80 (1, 2 H), 3.67 (t, 2 H), 3.00 (q, 4 H) | | |
| 4.12 | 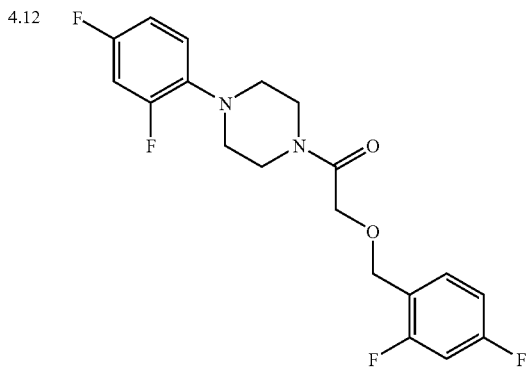 | 2-(2,4-Difluoro-benzyloxy)-1-[4-(2,4-difluoro-phenyl)-piperazin-1-yl]-ethanone | 62.7 mg, (56%) yellow oil |
| NMR | 7.41 (q, 1 H), 6.58 (m, 5 H), 4.64 (s, 2 H), 4.26 (s, 2 H), 3.80 (t, 2 H), 3.67 (t, 2 H), 3.01 (br, 4 H) | | |

The starting materials for compounds from 4.1 to 4.12 are prepared as follows (Example 5.1 to Example 5.2):

EXAMPLE 5.1

1-[4-(2,4-Dichloro-phenyl)-piperazin-1-yl]-2-hydroxy-ethanone

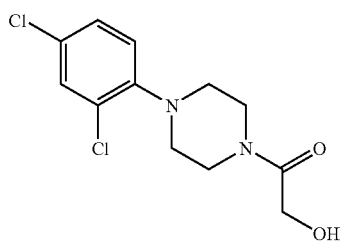

To a screw-cap vial was added glycolic acid (100 mg, 1.31 mmol), 1-(3-dimthylaminopropyl)-3-ethylcarbodiimide hydrochloride (277.3 mg, 1.45 mmol), hydroxybenzotriazole (195.5 mg, 1.45 mmol), 1-(2,4-dichlorophenyl)-piperazine dihydrochloride (439.8 mg, 1.45 mmol), triethylamine (0.55 mL, 3.94 mmol) and N,N-dimethylformamide (5 mL). The resulting mixture was stirred at room temperature overnight. The reaction mixture was diluted with ethyl acetate (8 mL), successively washed with water (8 mL), saturated aqueous sodium bicarbonate (2×8 mL) and water (8 mL). The organic layer was dried over anhydrous sodium sulfate, filtered and concentrated in vacuo. The crude residue was purified on silica gel using hexanes:ethyl acetate=4:1 to 100% ethyl acetate in a gradient fashion, to isolate the desired product as yellow solid (171.1 mg, 45%). $^1$H NMR (300 MHz, CDCl$_3$): δ 7.28 (d, 1H), 7.11 (dd, 1H), 6.85 (dd, 1H), 4.11 (br, 2H), 3.74 (t, 2H), 3.72 (br, 1H, OH), 3.36 (t, 2H), 2.92 (t, 4H)

In a similar fashion the following compound was synthesized:

| 5.2 | 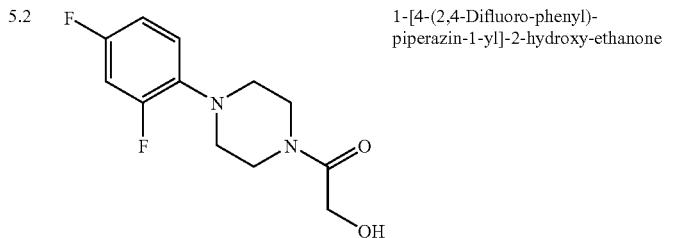 | 1-[4-(2,4-Difluoro-phenyl)-piperazin-1-yl]-2-hydroxy-ethanone | 1.59 g (61%) white solid |
|---|---|---|---|
| NMR | 6.85 (m, 3 H), 4.21 (d, 2 H), 3.85 (t, 2 H), 3.65 (t, 1 H, OH), 3.45 (t, 2 H), 3.03 (m, 4 H) | | |

EXAMPLE 6

4-(2,4-dichloro-phenyl)-4-hydroxy-piperidine-1-carboxylic acid tert-butyl ester

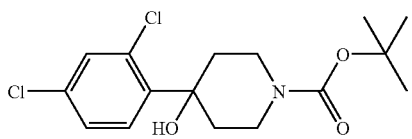

To solution of 1,3-dichloro 4-iodobenzene (1.0 g, 3.66 mmol) in tetrahydrofuran (10 mL) at −20° C. was added isopropyl magnesium chloride (2M in tetrahydrofuran, 1.9 mL, 3.84 mmol). The solution was stirred for 30 min and then a solution of 4-oxo-piperidine-1-carboxylic acid tert-butyl ester (0.73 g, 3.66 mmol) in tetrahydrofuran (5 mL) was added. The solution was allowed to warm to room temperature with stirring for 18 h. The reaction was quenched with a saturated aqueous solution of ammonium chloride (10 mL) and extracted with ethyl acetate (3×10 mL). The organic extracts were combined, washed with brine (20 mL), dried over sodium sulfate and concentrated in vacuo. The residue was dissolved in methanol (20 mL) followed by addition of sodium borohydride (0.14 g, 3.66 mmol). The resulting mixture was left stirring for 30 min. Methanol was removed in vacuo. Water (20 mL) was added to the residue and extracted with ethyl acetate (25 mL). The organic phase was dried over sodium sulfate. The gum obtained was chromatographed on silica gel using dichloromethane/methanol from 100% to 98% dichloromethane in a gradient fashion, to give the title compound as a white foamy solid (0.38 g, 30%). The material was used in next reaction without further purification.

EXAMPLE 7

4-(2,4-dichloro-phenyl)-piperidin-4-ol

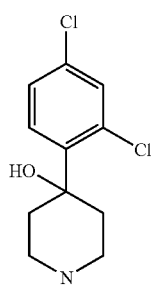

To a solution of 4-(2,4-dichloro-phenyl)-4-hydroxy-piperidine-1-carboxylic acid tert-butyl ester (0.38 g, 1.1 mmol) in dichloromethane (5 mL) was added trifluoroacetic acid (1 mL). The reaction was stirred at room temperature for 15 min. Solvent was removed in vacuo and the residue was partitioned between ethyl acetate and saturated aqueous sodium bicarbonate. The aqueous layer was extracted with ethyl acetate. The combined organic extracts were dried over sodium sulfate, filtered and concentrated in vacuo to give 4-(2,4-dichloro-phenyl)-piperidin-4-ol as a white solid (0.23 g, 85%). The material was used as is without further purification.

EXAMPLE 8

2-Benzyloxy-1-[4-(2,4-dichloro-phenyl)-4-hydroxy-piperidin-1-yl]-ethanone

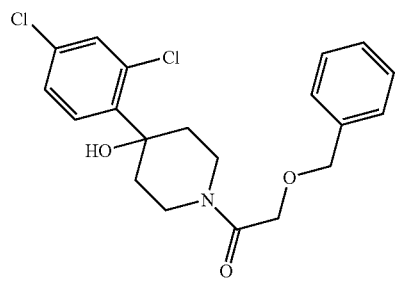

To a solution of 4-(2,4-dichloro-phenyl)-piperidin-4-ol (0.10 g, 0.40 mmol) in dichloromethane (2 mL) was added diisopropyl ethylamine (0.073 mL, 0.42 mmol) followed by benzyloxy acetyl chloride (0.078 g, 0.42 mmol). The reaction mixture was stirred at room temperature for 1 hour. The reaction mixture was diluted with dichloromethane (10 mL) and washed with saturated aqueous sodium bicarbonate (10 mL). The organic layer was dried over sodium sulfate, filtered and concentrated in vacuo. The residual oil was chromatographed on silica gel using dichloromethane/methanol from 100% to 97% dichloromethane in a gradient fashion, to give the title compound as a glassy solid. The material was used as is without further purification. $^1$H NMR (300 MHz, CDCl$_3$):

δ 7.35 (m, 8H), 4.58 (m, 3H), 4.22 (m, 2H), 3.86 (bm, 1H), 3.57 (bm, 1H), 3.13 (bm, 1H), 2.64 (s, 1H), 2.26 (m, 2H), 1.97 (m, 2H).

EXAMPLE 9

2-Benzyloxy-1-[4-(2,4-dichloro-phenyl)-3,6-dihydro-2H-pyridin-1-yl]-ethanone

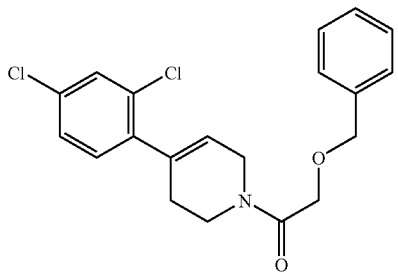

A solution of 2-benzyloxy-1-[4-(2,4-dichloro-phenyl)-4-hydroxy-piperidin-1-yl]-ethanone (0.035 g, 0.09 mmol) in trifluoroacetic acid (1 mL) was stirred at RT for 48 h. Ethyl acetate (2 mL) and saturated aqueous sodium bicarbonate (2 mL) were added and the layers were separated. The organic layer was dried over sodium sulfate, filtered and concentrated in vacuo. The isolated residue was chromatographed on silica gel using dichloromethane/ethyl acetate to 100% to 90% dichloromethane in a gradient fashion, to give the title compound as a gum (0.0094 g, 28%).

$^1$H NMR (300 MHz, CDCl$_3$): complex mixture of rotomers, δ 7.21 (m, 8H), 5.68 (m, 1H), 4.65 (m, 2H), 4.20 (m, 2H), 3.82 (m), 3.53 (m), 2.91 (m), 2.44 (m), 1.94 (m).

EXAMPLE 10

4-(2,4-Dichloro-phenyl)-[1,4]diazepane-1-carboxylic acid tert-butyl ester

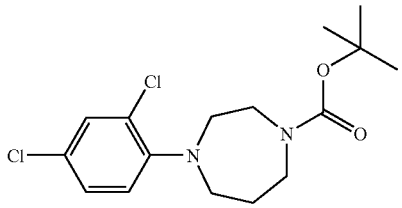

To a solution of [1,4]diazepane-1-carboxylic acid tert-butyl ester (0.36 g, 1.77 mmol) in toluene (5 mL) was added tris(dibenzylideneacetone)-dipalladium(0) (0.040 g, 0.044 mmol), R(+)-2,2'-bis(diphenylphosphino)-1,1'-binapthyl (0.027 g, 0.044 mmol), sodium t-butoxide (0.13 g, 1.33 mmol), and 1-bromo-2,4-dichlorobenzene (0.20 g, 0.89 mmol). The solution was heated to 100° C. for 2 h. The reaction was cooled to room temperature, diethylether (5 mL) was added and the resulting mixture filtered through a bed of diatomaceous earth. The residue was chromatographed on silica gel using hexane/ethyl acetate from 100% to 95% hexane in a gradient fashion, to give the title compound as a gum (0.13 g, 43%). The residue was used as is without further purification.

EXAMPLE 11

1-(2,4-Dichloro-phenyl)-[1,4]diazepane

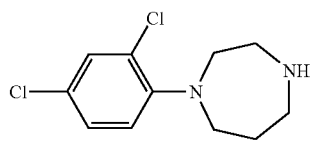

To a solution of 4-(2,4-dichloro-phenyl)-[1,4]diazepane-1-carboxylic acid tert-butyl ester (0.13 g, 0.38 mmol) in dichloromethane (2 mL) was added trifluoroacetic acid (1 mL). The reaction was stirred until complete (as monitored by LC-MS) and the volatiles were removed in vacuo. The residue was partitioned between ethyl acetate (5 mL) and saturated aqueous sodium bicarbonate (5 mL). The organic layer was separated, dried over sodium sulfate, filtered and concentrated in vacuo to give the title compound as a gum (0.09 g, 100%).

EXAMPLE 12

2-Benzyloxy-1-[4-(2,4-dichloro-phenyl)-[1,4]diazepan-1-yl]-ethanone

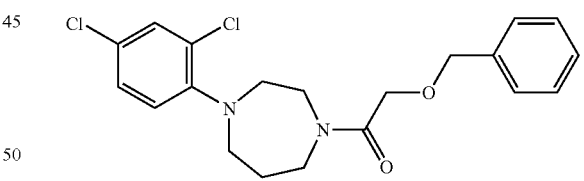

To a solution of 1-(2,4-dichloro-phenyl)-[1,4]diazepane (0.11 g, 0.45 mmol) in dichloromethane (5 mL) was added diisopropyl-ethylamine (0.082 mL, 0.47 mmol) and benzyloxyacetyl chloride (0.086 g, 0.47 mmol). The solution was stirred at room temperature for 1 h. The residue was chromatographed on silica gel using dichloromethane/ethyl acetate from 100% to 95% dichloromethane in a gradient fashion, to obtain the title compound as a gum (0.80 g, 46%).

$^1$H NMR (300 MHz, CDCl$_3$): δ 7.33 (m, 6H), 7.14 (m, 1H), 6.96 (m. 1H), 4.64 (m, 2H), 4.21 (m, 2H), 3.79 (m, 2H), 3.65 (m, 2H), 3.19 (m, 4H), 2.04 (m, 2H).

EXAMPLE 13.1

1-[4-(2,4-Dichloro-phenyl)-piperazin-1-yl]-2-(3-methyl-pyridin-4-ylmethoxy)-ethanone

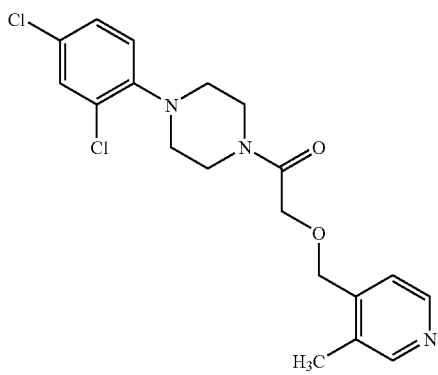

General Procedure: To a screw-cap vial equipped with a stir bar were added sodium hydride (60% in mineral oil, 25 mg, 0.633 mmol) and tetrahydrofuran (1 mL). The suspension was cooled to 0° C. and to it was added a solution of (3-methyl-pyridin-4-yl)-methanol (65 mg, 0.528 mmol) in tetrahydrofuran (1 mL) dropwise. The reaction mixture was stirred at 0° C. for 15 minutes and then a solution of 2-chloro-1-[4-(2,4-dichloro-phenyl)-piperazin-1-yl]-ethanone (192 mg, 0.633 mmol) in tetrahydrofuran (1 mL) was added in one portion. The reaction mixture was stirred at room temperature overnight, quenched with water and extracted with dichloromethane. The combined organic layer was washed with brine, dried over anhydrous sodium sulfate, filtered and concentrated in vacuo. The residue was purified on silica gel using hexanes:ethyl acetate=80:20 to 30:70 in a gradient fashion, to give the desired product as a white solid (72 mg, 35%). $^1$H NMR (300 MHz, CDCl$_3$): δ 8.45 (d, 1H), 8.38 (s, 1H), 7.64 (d, 1H), 7.41 (d, 1H), 7.22 (dd, 1H), 6.93 (d, 1H), 4.72 (s, 2H), 4.39 (s, 2H), 3.82 (t, 2H), 3.65 (t, 2H), 3.02 (t, 4H), 2.30 (s, 3H).

In a similar fashion the following compounds were synthesized:

| | | | |
|---|---|---|---|
| 13.2 | 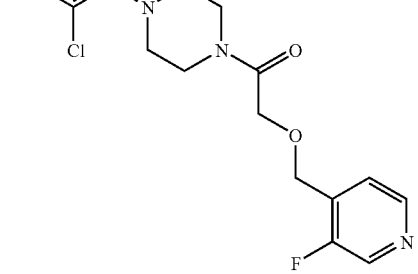 | 1-[4-(2-Chloro-4-fluoro-phenyl)-piperazin-1-yl]-2-(3-fluoro-pyridin-4-ylmethoxy)-ethanone | 39.3 mg (60%) colourless oil |
| NMR | 8.45 (s, 2 H), 7.49 (t, 1 H), 7.16 (tt, 1 H), 6.97 (dd, 2 H), 4.76 (s, 2 H), 4.34 (s, 2 H), 3.82 (t, 2 H), 3.66 (t, 2 H), 2.99 (m, 4 H) | | |
| 13.3 | 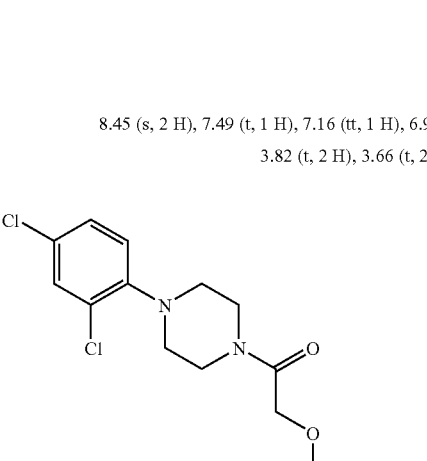 | 1-[4-(2,4-Dichloro-phenyl)-piperazin-1-yl]-2-(3-fluoro-pyridin-4-ylmethoxy)-ethanone | 106 mg (81%) pale yellow oil |
| NMR | 8.45 (m, 2 H), 7.48 (t, 1 H), 7.41 (d, 1 H), 7.22 (dd, 1 H), 6.93 (d, 1 H), 4.75 (s, 2 H), 4.34 (s, 2 H), 3.82 (t, 2 H), 3.67 (t, 2 H), 3.02 (m, 4 H) | | |

| | | | | |
|---|---|---|---|---|
| 13.4 | 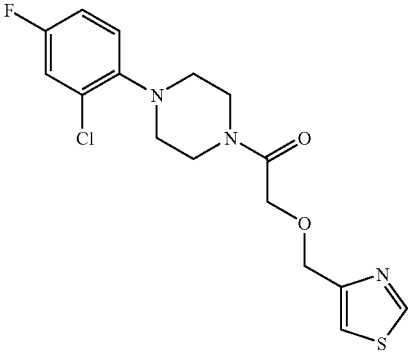 | | 1-[4-(2-Chloro-4-fluoro-phenyl)-piperazin-1-yl]-2-(thiazol-4-ylmethoxy)-ethanone | 104.6 mg (66%) yellow oil |
| NMR | 8.82 (d, 1 H), 7.38 (d, 1 H), 7.15 (dd, 1 H), 6.97 (m, 2 H), 4.82 (s, 2 H), 4.33 (s, 2 H), 3.80 (t, 2 H), 3.69 (t, 2 H), 2.98 (t, 4 H) | | | |
| 13.5 | 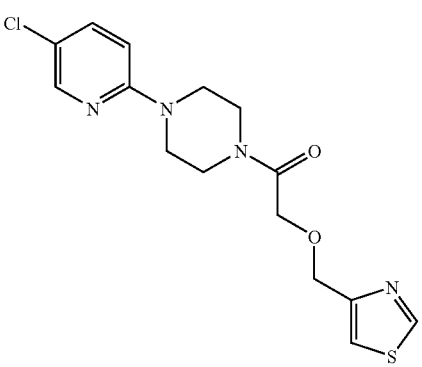 | | 1-[4-(5-Chloro-pyridin-2-yl)-piperazin-1-yl]-2-(thiazol-4-ylmethoxy)-ethanone | 88.5 mg (58%) off-white solid |
| NMR | 8.82 (d, 1 H), 8.13 (d, 1 H), 7.46 (dd, 1 H), 7.38 (d, 1 H), 6.61 (d, 1 H), 4.81 (s, 2 H), 4.33 (s, 2 H), 3.74 (m, 2 H), 3.57 (m, 6 H) | | | |
| 13.6 | 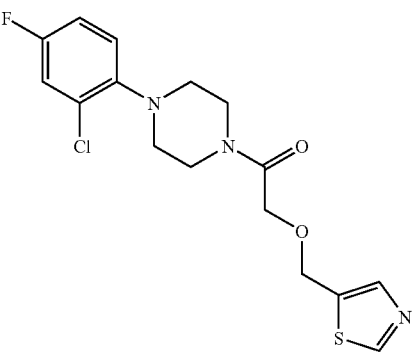 | | 1-[4-(2-Chloro-4-fluoro-phenyl)-piperazin-1-yl]-2-(thiazol-5-ylmethoxy)-ethanone | 117.8 mg (74%) pale yellow oil |
| NMR | 8.83 (s, 1 H), 7.85 (s, 1 H), 7.16 (m, 1 H), 6.97 (dd, 2 H), 4.88 (s, 2 H), 4.25 (s, 2 H), 3.80 (t, 2 H), 3.63 (t, 2 H), 2.98 (m, 4 H) | | | |
| 13.7 | 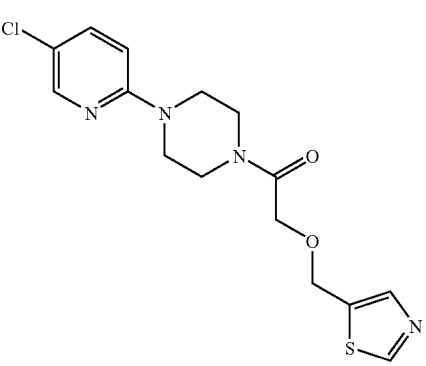 | | 1-[4-(5-Chloro-pyridin-2-yl)-piperazin-1-yl]-2-(thiazol-5-ylmethoxy)-ethanone | 81.1 mg (53%) off-white solid |

| | | | |
|---|---|---|---|
| NMR | 8.83 (s, 1 H), 8.14 (d, 1 H), 7.84 (s, 1 H), 7.47 (dd, 1 H), 6.61 (d, 1 H), 4.88 (s, 2 H), 4.24 (s, 2 H), 3.75 (t, 2 H), 3.54 (m, 6 H) | | |
| 13.8 | 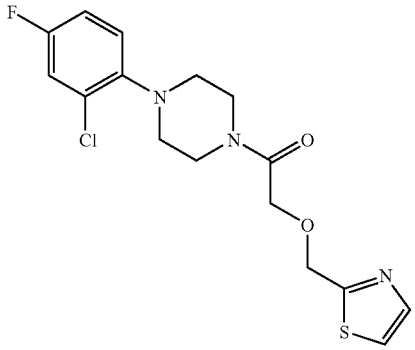 | 1-[4-(2-Chloro-4-fluoro-phenyl)-piperazin-1-yl]-2-(thiazol-2-ylmethoxy)-ethanone | 90.5 mg (57%) clear oil |
| NMR | 7.79 (d, 1 H), 7.39 (d, 1 H), 7.15 (m, 1 H), 6.97 (m, 2 H), 4.95 (s, 2 H), 4.36 (s, 2 H), 3.81 (t, 2 H), 3.66 (t, 2 H), 2.99 (t, 4 H) | | |
| 13.9 | 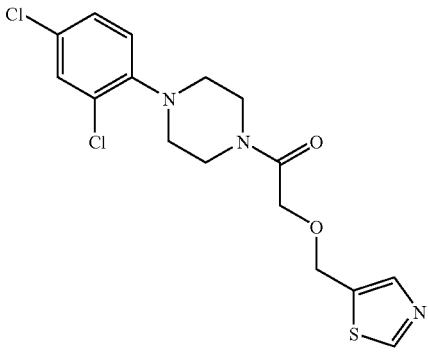 | 1-[4-(2,4-Dichloro-phenyl)-piperazin-1-yl]-2-(thiazol-5-ylmethoxy)-ethanone | 125 mg (75%) yellow oil |
| NMR | 8.83 (s, 1 H), 7.85 (s, 1 H), 7.40 (d, 1 H), 7.22 (dd, 1 H), 6.93 (d, 1 H), 4.88 (s, 2 H), 4.24 (s, 2 H), 3.81 (t, 2 H), 3.63 (t, 2 H), 3.00 (m, 4 H) | | |
| 13.10 | 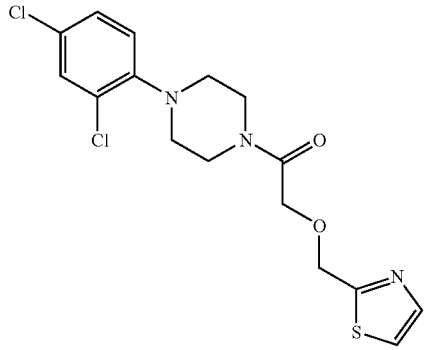 | 1-(4-(2,4-Dichloro-phenyl)-piperazin-1-yl]-2-(thiazol-2-ylmethoxy)-ethanone | 83.7 mg (50%) white solid |
| NMR | 7.79 (d, 1 H), 7.39 (m, 2 H), 7.21 (dd, 1 H), 6.93 (d, 1 H), 4.95 (s, 2 H), 4.36 (s, 2 H), 3.81 (t, 2 H), 3.66 (t, 2 H), 3.01 (t, 4 H) | | |

-continued

| | | | | |
|---|---|---|---|---|
| 13.11 | 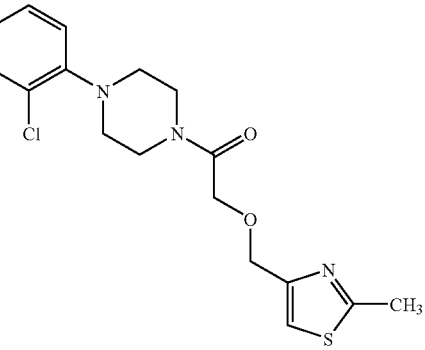 | | 1-[4-(2,4-Dichloro-phenyl)-piperazin-1-yl]-2-(2-methyl-thiazol-4-ylmethoxy)-ethanone | 119.6 mg (70%) clear oil |
| NMR | 7.40 (d, 1 H), 7.21 (dd, 1 H), 7.13 (s, 1 H), 6.93 (d, 1 H), 4.69 (s, 2 H), 4.31 (s, 2 H), 3.80 (t, 2 H), 3.70 (t, 2 H), 3.00 (t, 4 H), 2.72 (s, 3 H) | | | |
| 13.12 | 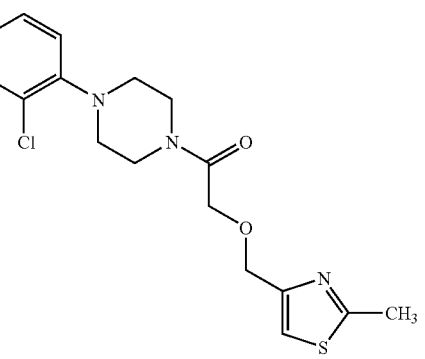 | | 1-[4-(2-Chloro-4-fluoro-phenyl)-piperazin-1-yl]-2-(2-methyl-thiazol-4-ylmethoxy)-ethanone | 125.5 mg (76%) clear oil |
| NMR | 8.14 (d, 1 H), 7.46 (dd, 1 H), 7.12 (s, 1 H), 6.60 (d, 1 H), 4.69 (s, 2 H), 4.31 (s, 2 H), 3.74 (m, 2 H), 3.65 (m, 2 H), 3.56 (m, 4 H), 2.71 (s, 3 H) | | | |
| 13.13 | 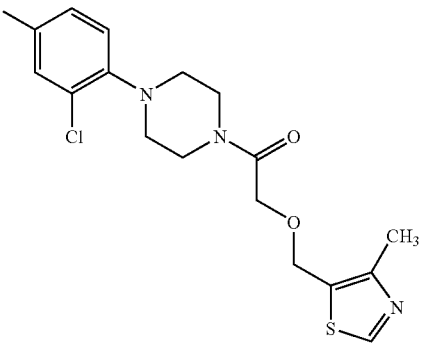 | | 1-[4-(2,4-Dichloro-phenyl)-piperazin-1-yl]-2-(4-methyl-thiazol-5-ylmethoxy)-ethanone | 125.7 mg (72%) yellow oil |
| NMR | 8.72 (s, 1 H), 7.41 (d, 1 H), 7.23 (m, 1 H), 6.93 (d, 1 H), 4.83 (s, 2 H), 4.24 (s, 2 H), 3.81 (m, 2 H), 3.65 (m, 2 H), 3.00 (m, 4 H), 2.49 (s, 3 H) | | | |
| 13.14 | 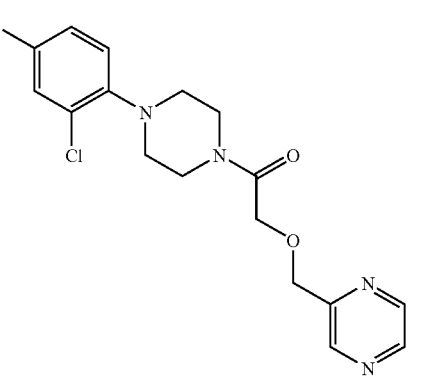 | | 1-[4-(2,4-Dichloro-phenyl)-piperazin-1-yl]-2-(pyrazin-2-ylmethoxy)-ethanone | 79.8 mg (48%) white solid |

| | | | |
|---|---|---|---|
| NMR | 8.76 (s, 1 H), 8.53 (m, 2 H), 7.38 (d, 1 H), 7.20 (dd, 1 H), 6.91 (d, 1 H), 4.80 (s, 2 H), 4.38 (s, 2 H), 3.81 (t, 2 H), 3.68 (t, 2 H), 3.00 (t, 4 H) | | |
| 13.15 | 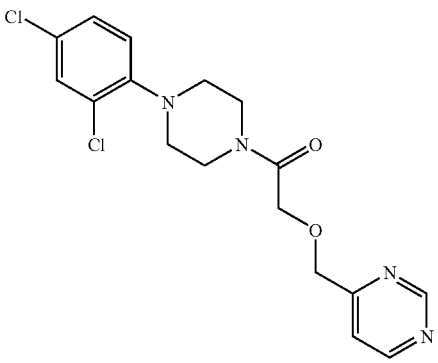 | 1-[4-(2,4-Dichloro-phenyl)-piperazin-1-yl]-2-(pyrimidin-4-ylmethoxy)-ethanone | 50.5 mg (29%) yellow solid |
| NMR | 9.15 (d, 1 H), 8.75 (d, 1 H), 7.56 (d, 1 H), 7.39 (d, 1 H), 7.21 (dd, 1 H), 6.92 (d, 1 H), 4.74 (s, 2 H), 4.38 (s, 2 H), 3.82 (t, 2 H), 3.66 (m, 2 H), 3.01 (m, 4 H) | | |
| 13.16 | 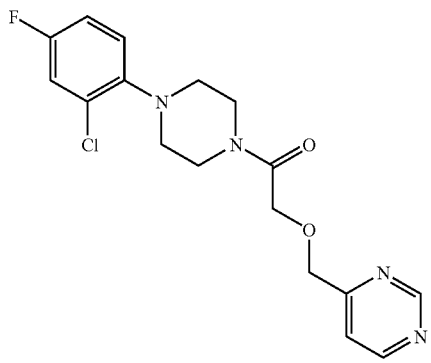 | 1-[4-(2-Chloro-4-fluoro-phenyl)-piperazin-1-yl]-2-(pyrimidin-4-ylmethoxy)-ethanone | 44 mg (28%) yellow oil |
| NMR | 9.16 (d, 1 H), 8.75 (d, 1 H), 7.56 (d, 1 H), 7.15 (m, 1 H), 6.96 (dd, 2 H), 4.74 (s, 2 H), 4.38 (s, 2 H), 3.81 (t, 2 H), 3.66 (t, 2 H), 2.99 (t, 4 H) | | |
| 13.17 | 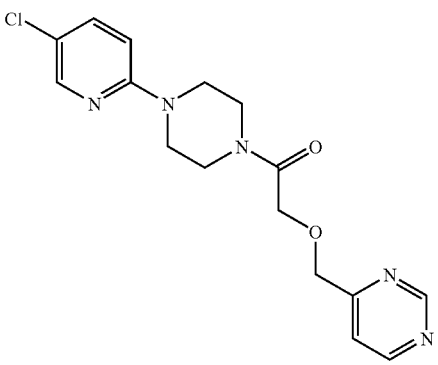 | 1-[4-(5-Chloro-pyridin-2-yl)-piperazin-1-yl]-2-(pyrimidin-4-ylmethoxy)-ethanone | 18.1 mg (11%) yellow solid |
| NMR | 9.21 (s, 1 H), 8.75 (d, 1 H), 8.13 (d, 1 H), 7.56 (d, 1 H), 7.46 (dd, 1 H), 6.61 (d, 1 H), 4.74 (s, 2 H), 4.39 (s, 2 H), 3.77 (m, 2 H), 3.61 (m, 4 H), 3.52 (m, 2 H) | | |

-continued

| | | | | |
|---|---|---|---|---|
| 13.18 | 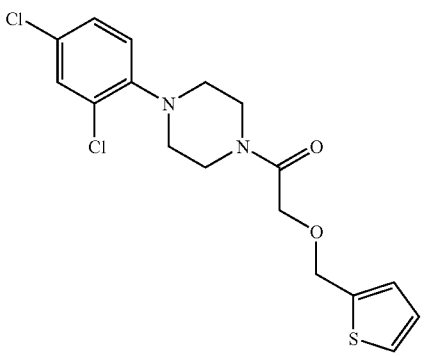 | | 1-[4-(2,4-Dichloro-phenyl)-piperazin-1-yl)-2-(thiophen-2-ylmethoxy)-ethanone | 90.5 mg (49%) yellow oil |
| NMR | 7.37 (d, 1 H), 7.31 (d, 1 H), 7.19 (dd, 1 H), 7.04 (m, 1 H), 6.98 (m, 1 H), 6.91 (d, 1 H), 4.78 (s, 2 H), 4.21 (s, 2 H), 3.77 (t, 2 H), 3.64 (t, 2 H), 2.97 (t, 4 H) | | | |
| 13.19 | 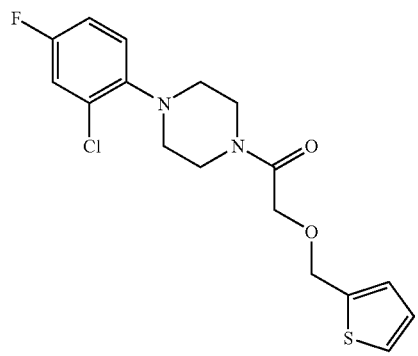 | | 1-[4-(2-Chloro-4-fluoro-phenyl)-piperazin-1-yl]-2-thiophen-2-ylmethoxy)-ethanone | 80.1 mg (50%) yellow oil |
| NMR | 7.32 (d, 1 H), 7.14 (d, 1 H), 7.05 (m, 1 H), 6.97 (m, 3 H), 4.79 (s, 2 H), 4.22 (s, 2 H), 3.78 (t, 2 H), 3.65 (t, 2 H), 2.96 (t, 4 H) | | | |
| 13.20 | 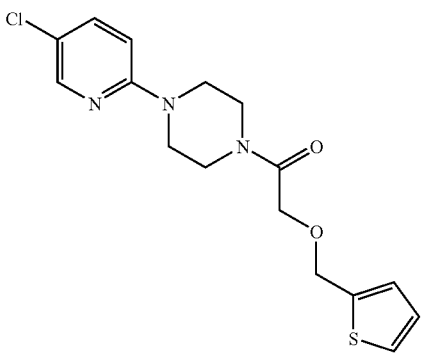 | | 1-[4-(5-Chloro-pyridin-2-yl)-piperazin-1-yl]-2-(thiophen-2-ylmethoxy)-ethanone | 16.2 mg (10%) colourless oil |
| NMR | 8.13 (d, 1 H), 7.46 (dd, 1 H), 7.33 (dd, 1 H), 7.05 (m, 1 H), 6.99 (m, 1 H), 6.59 (d, 1 H), 4.79 (s, 2 H), 4.22 (s, 2 H), 3.73 (m, 2 H), 3.53 (m, 6 H) | | | |
| 13.21 | 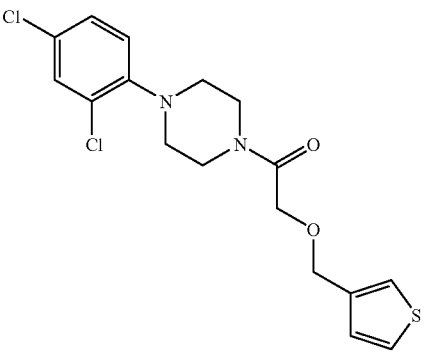 | | 1-[4-(2,4-Dichloro-phenyl)-piperazin-1-yl]-2-(thiophene-3-ylmethoxy)-ethanone | 31.7 mg (26%) yellow oil |

| | | | |
|---|---|---|---|
| NMR | 7.39 (dd, 1 H), 7.32 (m, 1 H), 7.27 (s, 1 H), 7.21 (dd, 1 H), 7.10 (dd, 1 H), 6.91 (d, 1 H), 4.68 (s, 2 H), 4.21 (s, 2 H), 3.79 (m, 2 H), 3.66 (t, 2 H), 2.98 (m, 4 H) | | |
| 13.22 | 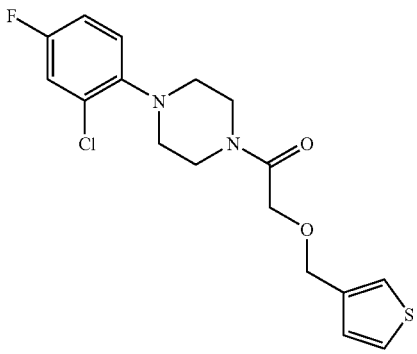 | 1-[4-(2-Chloro-4-fluoro-phenyl)-piperazin-1-yl]-2-(thiophen-3-ylmethoxy)-ethanone | 38 mg (31%) yellow oil |
| NMR | 7.33 (m, 1 H), 7.27 (s, 1 H), 7.11 (m, 2 H), 6.95 (dd, 2 H), 4.64 (s, 2 H), 4.21 (s, 2 H), 3.78 (m, 2 H), 3.66 (t, 2 H), 2.95 (m, 4 H) | | |
| 13.23 | 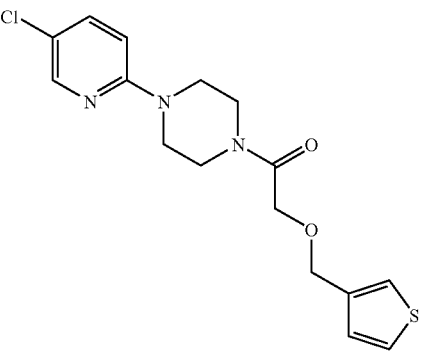 | 1-[4-(5-Chloro-pyridin-2-yl)-piperazin-1-yl]-2-(thiophen-3-ylmethoxy)-ethanone | 36.5 mg (31%) yellow oil |
| NMR | 8.13 (d, 1 H), 7.46 (dd, 1 H), 7.33 (m, 1 H), 7.26 (s, 1 H), 7.10 (dd, 1 H), 6.59 (d, 1 H), 4.63 (s, 2 H), 4.21 (s, 2 H), 3.73 m, 2 H), 3.53 (m, 6 H) | | |
| 13.24 | 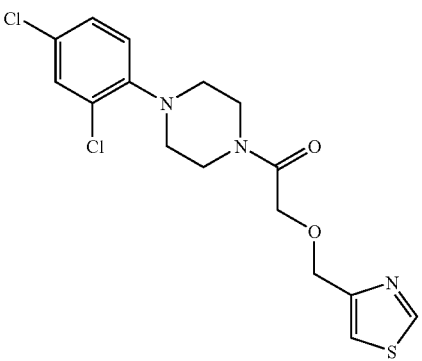 | 1-[4-(2,4-Dichloro-phenyl)-piperazin-1-yl]-2-(thiazol-4-ylmethoxy)-ethanone | 135.5 mg (89%) |
| NMR | 8.79 (d, 1 H), 7.36 (m, 2 H), 7.18 (dd, 1 H), 6.91 (d, 1 H), 4.75 (s, 2 H), 4.31 (s, 2 H), 3.78 (m, 2 H), 3.68 (m, 2 H), 2.98 (m, 4 H) | | |

The starting materials (piperazines or alcohols) for compounds 16.1 to 16.39 are prepared as follows (Example 14.1 to Example 14.9):

EXAMPLE 14.1

2-Chloro-1-[4-(2,4-dichloro-phenyl)-piperazin-1-yl]-ethanone

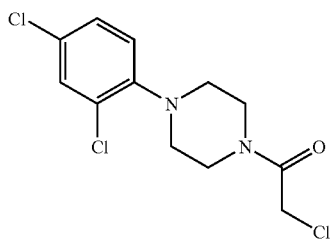

General Procedure: To a 50 mL round bottom flask equipped with a stir bar were added 1-(2,4-dichloro-phenyl)-piperazine dihydrochloride (1.0 g, 3.29 mmol) and chloroform (7 mL).

The solution was cooled to 0° C. and triethylamine (1.38 mL, 9.87 mmol) was added followed by the dropwise addition of chloroacetyl chloride (0.29 mL, 3.62 mL). The reaction mixture was stirred at 0° C. for 2.5 hours, quenched with water (50 mL) and extracted with dichloromethane (3×50 mL). The combined organic layer was washed with brine (50 mL), dried over anhydrous sodium sulfate, filtered and concentrated in vacuo. The residue was purified on silica gel using hexanes:diethyl ether=70:30 to 40:60 in a gradient fashion, to give an oil. The oil was triturated with hexanes to give the desired product as an off-white solid (934 mg, 92%).
$^1$H NMR (300 MHz, CDCl$_3$): δ 7.41 (d, 1H), 7.22 (dd, 1H), 6.96 (d, 1H), 4.12 (s, 2H), 3.82 (t, 2H), 3.71 (t, 2H), 3.06 (m, 4H).

In a similar fashion the following compounds were synthesized:

| 14.2 | 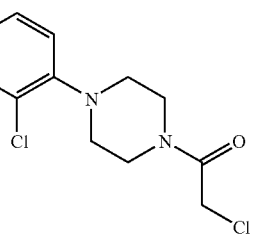 | 2-Chloro-1-[4-(2-chloro-4-fluoro-phenyl)-piperazin-1-yl]-ethanone | 582 mg (67%) orange oil |
|---|---|---|---|
| NMR | | 7.17 (m, 1 H), 6.99 (m, 2 H), 4.12 (s, 2 H), 3.82 (t, 2 H), 3.71 (t, 2 H), 3.05 (t, 2 H), 3.00 (t, 2 H) | |
| 14.3 | 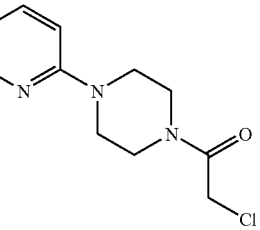 | 2-Chloro-1-[4-(5-chloro-pyridin-2-yl)-piperazin-1-yl]-ethanone | 1.14 g (41%) off-white solid |
| NMR | | 8.15 (d, 1 H), 7.48 (dd, 1 H), 6.62 (d, 1 H), 4.12 (s, 2 H), 3.76 (m, 2 H), 3.66 (s, 4 H), 3.53 (m, 2 H) | |

EXAMPLE 14.4

(3-Fluoro-pyridin-4-yl)-methanol

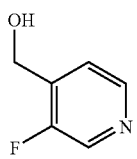

General Procedure: To a 50 mL round bottom flask equipped with a stir bar were added calcium chloride (96%, 1.12 g, 9.67 mmol), tetrahydrofuran (5 mL) and ethanol (5 mL). The suspension was cooled to −20° C. and sodium borohydride (96%, 699 mg, 17.73 mmol) was added. The reaction mixture was stirred at −20° C. for 20 minutes and then a solution of 3-fluoro-isonicotinic acid methyl ester (500 mg, 3.22 mmol) in tetrahydrofuran (5 mL) was added. The reaction mixture was stirred at −20° C. for 15 minutes and then at room temperature over the weekend. The reaction was quenched with cold saturated aqueous ammonium chloride (40 mL) and extracted with diethyl ether (3×60 mL). The combined organic layer was washed with brine (75 mL), dried over anhydrous sodium sulfate, filtered and concentrated in vacuo. The residue was purified on silica gel using dichloromethane:ethyl acetate=80:20 to 60:40 in a gradient fashion, to give the desired product as a white solid (223 mg, 54%). $^1$H NMR (300 MHz, CDCl$_3$): δ 8.43 (m, 2H), 7.50 (t, 1H), 4.86 (d, 2H), 2.25 (t, 1H).

In a similar fashion the following compounds were synthesized:

| 14.5 | 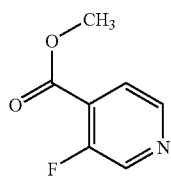 | (3-Methyl-pyridin-4-yl)methanol | 274 mg (67%) white solid |
|---|---|---|---|
| NMR | 8.44 (d, 1 H), 8.34 (s, 1 H), 7.67 (d, 1 H), 4.82 (s, 2 H), 2.28 (s, 3 H), 2.08 (m, 1 H) | | |

EXAMPLE 14.6

3-Fluoro-isonicotinic acid methyl ester

General Procedure: To a 50 mL round bottom flask equipped with a stir bar and a reflux condenser were added 3-fluoroisonicotinic acid (1.0 g, 7.09 mmol), methanol (10 mL) and sulfuric acid (4.2 mL). The reaction mixture was heated at 70° C. overnight, cooled to room temperature and concentrated in vacuo. The residue was cooled in an ice bath, basified to pH 9 using saturated aqueous sodium carbonate and extracted with ethyl acetate (2×). The combined organic layer was dried over anhydrous sodium sulfate, filtered and concentrated in vacuo to give the desired product as yellow oil (1.03 g, 94%). $^1$H NMR (300 MHz, CDCl$_3$): δ 8.62 (d, 1H), 8.54 (d, 1H), 7.77 (t, 1H), 3.98 (s, 3H).

EXAMPLE 14.7

2-Methyl-thiazole-4-carboxylic acid methyl ester

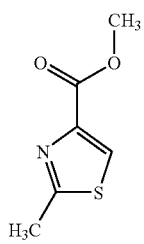

General Procedure: To a 100 mL round bottom flask equipped with a stir bar were added 2-methyl-1,3-thiazole-4-carboxylic acid (1.0 g, 6.98 mmol), potassium carbonate (3.86 g, 27.9 mmol), N,N-dimethylformamide (20 mL) and iodomethane (0.52 mL 8.38 mmol). The reaction mixture was stirred at room temperature over the weekend, diluted with ethyl acetate (100 mL) and washed with water (100 mL). The aqueous layer was then extracted with ethyl acetate (3×75 mL). The combined organic layer was washed with brine (100 mL), dried over anhydrous sodium sulfate, filtered and concentrated in vacuo. The residue was purified on silica gel using hexanes:ethyl acetate=80:20 to 50:50 in a gradient fashion, to give the desired product as an off-white solid (1.06 g, 97%). $^1$H NMR (300 MHz, CDCl$_3$): δ 8.06 (s, 1H), 3.95 (s, 3H), 2.78 (s, 3H).

EXAMPLE 14.8

(4-Methyl-thiazol-5-yl)-methanol

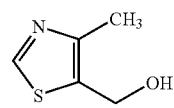

General Procedure: To a 100 mL round bottom flask equipped with a stir bar were added 4-methyl-thiazole-5-carbaldehyde (1.0 g, 7.86 mmol) and methanol (15 mL). The reaction mixture was heated to 60° C. and sodium borohydride (96%, 1.24 g, 31.5 mmol) was added in portions. The reaction mixture was stirred at 60° C. for 20 minutes and then at room temperature overnight. The reaction mixture was concentrated in vacuo, the residue was dissolved in ethyl acetate (100 mL) and the mixture was washed with water (20 mL). The aqueous layer was extracted with ethyl acetate (3×75 mL) and the combined organic layer was dried over anhydrous sodium sulfate, filtered and concentrated in vacuo. The residue was purified on silica gel using hexanes:diethyl ether=70:30 to 0:100 in a gradient fashion, to give the desired product as a white solid (834 mg, 82%). $^1$H NMR (300 MHz, CDCl$_3$): δ 8.65 (s, 1H), 4.84 (d, 2H), 2.52 (t, 1H), 2.44 (s, 3H).

In a similar fashion the following compounds were synthesized:

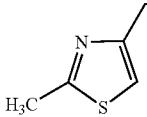

| 14.9 | | (2-Methyl-thiazol-4-yl)-methanol | 686 mg (78%) |
|---|---|---|---|
| NMR | 7.02 (s, 1 H), 4.71 (d, 2 H), 3.84 (t, 1 H), 2.69 (s, 3 H) | | |

What is claimed is:
1. A compound selected from the group consisting of:
2-benzyloxy-1-[4-(4-fluorophenyl)-piperazin-1-yl]-ethanone,
2-benzyloxy-1-[4-(2-chloro-5-trifluoro methyl-phenyl)-piperazin-1-yl]-ethanone,
2-benzyloxy-1-[4-(3,5-dichloro-pyridin-4-yl)-piperazin-1-yl]-ethanone,
2-benzyloxy-1-[4-(5-chloro-2-methyl-phenyl)-piperazin-1-yl]-ethanone,
4-[4-(2-benzyloxyacetyl)-piperazin-1-yl]-benzonitrile,
2-benzyloxy-1-[4-(4-trifluoromethyl-phenyl)-piperazin-1-yl]-ethanone,
2-benzyloxy-1-[4-(3,5-dichloromethyl phenyl)-piperazin-1-yl]-ethanone,
2-benzyloxy-1-[4-(2,3-dichlorophenyl)-piperazin-1-yl]-ethanone,
2-benzyloxy-1-[4-(2,4-dichlorophenyl)-piperazin-1-yl]-ethanone,
2-benzyloxy-1-(4-p-tolyl-piperazin-1-yl)-ethanone,
2-benzyloxy-1[4-(2-chlorophenyl)-piperazin-1-yl]-ethanone,
2-benzyloxy-1-(4-phenyl-piperazin-1-yl)-ethanone,
2-benzyloxy-1-(4-pyridin-2-yl-piperazin-1-yl)-ethanone,
2-benzyloxy-1-(3-methyl-4phenyl-piperazin-1-yl)-ethanone,
2-benzyloxy-1-[4-(2,4-difluoro-phenyl)-piperazin-1-yl]-ethanone,
2-benzyloxy-1-[4-(2-trifluoromethyl-phenyl)-piperazin-1-yl]-ethanone,
2-benzyloxy-1-[4-(5-ethynyl-pyridin-2-yl)-piperazin-1-yl]-ethanone,
2-benzyloxy-1-[4-(2-fluorophenyl)-piperazin-1-yl]-ethanone,
2-benzyloxy-1[4-(5-trifluoromethyl-pyridin-2-yl)-piperazin-1-yl]-ethanone,
2-benzyloxy-1-[4-(6-methyl-pyridin-2-yl)-piperazin-1-yl]-ethanone,
2-benzyloxy-1-[4-(2,5-dichlorophenyl)-piperazin-1-yl]-ethanone,
2-benzyloxy-1-[4-(3,4-dichloro-phenyl)-piperazin-1-yl]-ethanone,
2-[4-(2-benzyloxy-acetyl)-piperazin-1-yl]-nicotinonitrile,
1[4-(2,4-difluoro-phenyl)-piperazin-1-yl]-2-(4-fluoro-benzyloxy)-propan-1-one,
1[4-(2,4-dichloro-phenyl)-piperazin-1-yl]-2-(4-fluoro-benzyloxy)-propan-1-one,
1[4-(2,4-difluoro-phenyl)-piperazin-1-yl]-2-(3-methyl-3H-imidazol-4-ylmethoxy) -propan-1-one,
1-[4-(2,4-chloro-phenyl)-piperazin-1-yl]-2-(3methyl-3H-imidazol-4-ylmethoxy)-propan-1-one,
1[4-(2-chloro-4-fluoro-phenyl)-piperazin-1-yl]-2-(pyridin-2-ylmethyloxy)-ethanone,
1[4-(2-chloro-4-fluoro-phenyl)-piperazin-1-yl]-2-(pyridin-4-ylmethyloxy)-ethanone,
1-[4-(2,4-dichloro-phenyl)-piperazin-1-yl]-2-(pyridin-4-ylmethyloxy)-ethanone,
2-benzyloxy-1-[4-(4-fluoro-2-chloro-phenyl)-piperazin-1-yl]-ethanone,
2-benzyloxy-1[4-(2-chloro-4-fluoro-phenyl)-piperazin-1-yl]-ethanone,
1-[4-(2,4-dichloro-phenyl)-piperazin-1-yl]-2-(pyridin-2-ylmethoxy)-ethanone,
1-[4-(2,4-dichloro-phenyl)-piperazin-1-yl]-2-(pyridin-3-ylmethoxy)-ethanone,
1-[4-(2,4-difluoro-phenyl)-piperazin-1-yl]-2-(pyridin-2-ylmethoxy)-ethanone,
1-[4-(2,4-difluoro-phenyl)-piperazin-1-yl]-2-(pyridin-3-ylmethoxy)-ethanone,
1-[4-(2,4-dichloro-phenyl)-piperazin-1-yl]-2-(pyridin-4-ylmethoxy)-ethanone,
1-[4-(2,4-dichloro-phenyl)-piperazin-1-yl]-2-(3-fluoro-benzyloxy)-ethanone,
1-[4-(2,4-dichloro-phenyl)-piperazin-1-yl]-2-(4-fluoro-benzyloxy)-ethanone,
1-[4-(2,4-dichloro-phenyl)-piperazin-1-yl]-2-(2-fluoro-benzyloxy)-ethanone,
1-[4-(2,4-dichloro-phenyl)-piperazin-1-yl]-2-(2,3-difluoro-benzyloxy)-ethanone,
1[4-(2,4-dichloro-phenyl)-piperazin-1-yl]-2-(2,4-difluoro-benzyloxy)-ethanone,
1[4-(2,4-dichloro-phenyl)-piperazin-1-yl]-2-(2,5-difluoro-benzyloxy)-ethanone,
1-[4-(2,4-dichloro-phenyl)-piperazin-1-yl]-2-(2,6-difluoro-benzyloxy)-ethanone,
1-[4-(2,4-dichloro-phenyl)-piperazin-1-yl]-2-(3,4-difluoro-benzyloxy)-ethanone,
1-[4-(2,4-dichloro-phenyp-piperazin-1-yl]-2-(3,5-difluoro-benzyloxy)-ethanone,
1-[4-(2,4-difluoro-phenyl)-piperazin-1-yl]-2-(2-fluoro-benzyloxy)-ethanone,
1-[4-(2,4-difluoro-phenyl)-piperazin-1-yl]-2-(4-fluoro-benzyloxy)-ethanone,
2-(2,4-difluoro-benzyloxy)-1-[4-(2,4-difluoro-phenyl)-piperazin-1-yl]-ethanone,
2-benzyloxy-1[4-(2,4-dichloro-phenyl)-3,6-dihydro-2H-pyridin-1-yl]-ethanone,
2-benzyloxy-1[4-(2,4-dichloro-phenyl)[1,4]diazepan-1-yl]-ethanone,
1[4-(3-chloro-pyridin-4-yl)-piperazin-1-yl]-2-(pyridin-4-ylmethoxy)-ethanone,
1[4-(5-chloro-pyridin-2-yl)-piperazin-1-yl]-2-(pyridin-4-ylmethoxy)-ethanone,
1[4-(2,4-dichloro-phenyl)-2-methyl-piperazin-1-yl]-2-(pyridin-4-ylmethoxy)-ethanone,
1[4-(2,4-dichloro-phenyl)-piperazin-1-yl]-2-(1-pyridin-4-yl-ethoxy)-ethanone,
1[4-(2,4-dichloro-phenyl)-3-methyl-piperazin-1-yl]-2-(pyridin-4-ylmethoxy)-ethanone,
1-[4-(2,4-dichloro-phenyl)-2-methyl-piperazin-1-yl]-2-(pyridin-2-ylmethoxy)-ethanone,
1-[(R)-4-(2,4-dichloro-phenyl)-2-methyl-piperazin-1-yl]-2-(pyridin-4-ylmethoxy)-ethanone,
1-[(S)-4-(2,4-dichloro-phenyl)-2-methyl-piperazin-1-yl]-2-(pyridin-4-ylmethoxy)-ethanone,
1[4-(4-chloro-phenyl)-piperazin-1-yl]-2-(pyridin-2-ylmethoxy)-ethanone,

1[4-(4-chloro-phenyl)-piperazin-1-yl]-2-(pyridin-4-yl-methoxy)-ethanone,
1[4(5-methyl-pyridin-2-yl)-piperazin-1-yl]-2-(pyridin-2-ylmethoxy)-ethanone,
1-[4(5-fluoro-pyridin-2-yl)-piperazin-1-yl]-2-(pyridin-4-ylmethoxy)-ethanone,
1[4-(2-chloro-4-fluoro-phenyl)-2-methyl-piperazin-1-yl]-2-(pyridin-4-ylmethoxy)-ethanone,
1[4-(2,4-dichloro-phenyl)-piperazin-1-yl]-2-(3-methyl-pyridin-4-ylmethoxy)-ethanone,
1-[4-(2-chloro-4-fluoro-phenyl)-piperazin-1-yl]-2-(3-fluoro-pyridin-4-ylmethoxy)-ethanone,
1[4-(2,4-dichloro-phenyl)-piperazin-1-yl]-2-(3-fluoro-pyridin-4-ylmethoxy)-ethanone,
1[4-(2-chloro-4-fluoro-phenyl)-piperazin-1-yl]-2-(thiazol-4-ylmethoxy)-ethanone,
1[4-(5-chloro-pyridin-2-yl)-piperazin-1-yl]-2-(thiazol-4-ylmethoxy)-ethanone,
1[4-(2-chloro-4-fluoro-phenyl)-piperazin-1-yl]-2-(thiazol-5-ylmethoxy)-ethanone,
1-[4-(5-chloro-pyridin-2-yl)-piperazin-1-yl]-2-(thiazol-5-ylmethoxy)-ethanone,
1-[4-(2-chloro-4-fluoro-phenyl)-piperazin-1-yl]-2-(thiazol-2-ylmethoxy)-ethanone,
1-[4-(2,4-dichloro-phenyl)-piperazin-1-yl]-2-(thiazol-5-ylmethoxy)-ethanone,
1-[4-(2,4-dichloro-phenyl)-piperazin-1-yl]-2-(thiazol-2-ylmethoxy)-ethanone,
1-[4-(2,4-dichloro-phenyl)-piperazin-1-yl]-2-(2-methyl-thiazol-4-ylmethoxy)-ethanone,
1-[4-(2-chloro-4-fluoro-phenyl)-piperazin-1-yl]-2-(2-methyl-thiazo-4-ylmethoxy)-ethanone,
1-[4-(2,4-dichloro-phenyl)-piperazin-1-yl]-2-(4-methyl-thiazol-5-ylmethoxy)-ethanone,
1-[4-(2,4-dichloro-phenyl)-piperazin-1-yl]-2-(pyrazin-2-ylmethoxy)-ethanone,
1-[4-(2,4-dichloro-phenyl)-piperazin-1-yl]-2-(pyrimidin-4-ylmethoxy)-ethanone,
1-[4-(2-chloro-4-fluoro-phenyl)-piperazin-1-yl]-2-(pyrimidin-4-ylmethoxy)-ethanone,
1-[4-(5-chloro-pyridin-2-yl)-piperazin-1-yl]-2-(pyrimidin-4-ylmethoxy)-ethanone,
1-[4-(2,4-dichloro-phenyl)-piperazin-1-yl]-2-(thiophen-2-ylmethoxy)-ethanone,
1[4-(2-chloro-4-fluoro-phenyl)-piperazin-1-yl]-2-(thiophen-2-ylmethoxy)-ethanone,
1-[4-(5-chloro-pyridin-2-yl)-piperazin-1-yl]-2-(thiophen-2-ylmethoxy)-ethanone,
1-[4-(2,4-dichloro-phenyl)-piperazin-1-yl]-2-(thiophen-3-ylmethoxy)-ethanone,
1-[4-(2-chloro-4-fluoro-phenyl)-piperazin-1-yl]-2-(thiophen-3-ylmethoxy)-ethanone,
1-[4-(5-chloro-pyridin-2-yl)-piperazin-1-yl]-2-(thiophen-3-ylmethoxy)-ethanone, and
1-[4-(2,4-dichloro-phenyl)-piperazin-1-yl]-2-(thiazo-4-ylmethoxy)-ethanone.

2. A pharmaceutical composition comprising a compound according to claim 1 and a pharmaceutically acceptable carrier or excipient.

* * * * *